US011932847B2

(12) United States Patent
Ranik et al.

(10) Patent No.: US 11,932,847 B2
(45) Date of Patent: *Mar. 19, 2024

(54) TRANSPOSASE COMPETITOR CONTROL SYSTEM

(71) Applicant: Kapa Biosystems, Inc., Wilmington, MA (US)

(72) Inventors: Martin Ranik, Cape Town (ZA); Eric Van der Walt, Western Cape (ZA); William Bourn, Western Cape (ZA); Jennifer Hsieh, Cape Town (ZA); Abre De Beer, Zevenwacht Country Estate (ZA); Gerrida Uys, Cape Town (ZA); Paul McEwan, Camps Bay (ZA)

(73) Assignee: KAPA BIOSYSTEMS, INC., Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/491,148

(22) Filed: Apr. 19, 2017

(65) Prior Publication Data

US 2018/0195059 A1  Jul. 12, 2018

Related U.S. Application Data

(60) Provisional application No. 62/324,683, filed on Apr. 19, 2016.

(51) Int. Cl.
*C12N 9/12* (2006.01)
*C12N 15/10* (2006.01)
*C12Q 1/6806* (2018.01)

(52) U.S. Cl.
CPC ....... *C12N 15/1065* (2013.01); *C12N 9/1241* (2013.01); *C12Q 1/6806* (2013.01)

(58) Field of Classification Search
CPC .................................................... C12N 15/10
See application file for complete search history.

(56) References Cited

U.S. PATENT DOCUMENTS

| | | | |
|---|---|---|---|
| 4,554,101 A | 11/1985 | Hopp | |
| 5,965,443 A | 10/1999 | Reznikov et al. | |
| 10,337,038 B2* | 7/2019 | Lynch | C12N 9/1029 |
| 2014/0031261 A1* | 1/2014 | Goryshin | C12Q 1/6855 |
| | | | 506/16 |
| 2014/0093916 A1* | 4/2014 | Belyaev | C12N 9/22 |
| | | | 435/91.2 |
| 2015/0291942 A1* | 10/2015 | Gloeckner | C12Q 1/6869 |
| | | | 506/2 |
| 2018/0195059 A1* | 7/2018 | Ranik | C12N 9/1241 |
| 2018/0201925 A1* | 7/2018 | Steemers | C12N 9/22 |

FOREIGN PATENT DOCUMENTS

| | | |
|---|---|---|
| EP | 2 712 931 | 4/2014 |
| WO | WO 2014/189957 | 11/2014 |
| WO | WO 2016/003814 | 1/2016 |

OTHER PUBLICATIONS

Leschziner et al., Tn552 Transposase Catalyzes Concerted Strand Transfer In Vitro, Proceedings of the National Academy of Sciences, 1998, 95, 7345-7350. (Year: 1998).*
Trubitsyna et al., Structural Basis for the Inverted Repeat Preferences of Mariner Transposases, Journal of Biological Chemistry, 2015, 290(21), 13531-13540. (Year: 2015).*
STIC Search Results; Search Result 1, STIC Search Result 20190610_123429_us-15491148a-15.rag, 2019, 1-25. (Year: 2019).*
Jung et al., Comparative Genomic Transcriptomic Analyses Reveal Habitat Differentiation and Different Transcriptional Responses During Pectin Metabolism in Alishewanella Species, Applied and Environmental Microbiology, 2013, 79(20), 6351-6361. (Year: 2013).*
Vaezeslami et al., Site-Directed Mutagenesis Studies of Tn5 Transposase Residues Involved in Synaptic Complex Formation, Journal of Bacteriology, 2007, 189(20), 7436-7441. (Year: 2007).*
Mahillon et al., Insertion Sequences, Microbiology and Molecular Biology Reviews, 1998, 62(3), 725-774. (Year: 1998).*
Munoz-Lopez et al., DNA Transposons: Nature and Applications in Genomics, Current Genomics, 2010, 11(2), 115-128. (Year: 2010).*
Ohtsubo et al., Bacterial Insertion Sequences, Transposable Elements, Springer-Verlag Berlin Heidelberg, (Saedler ed.)1996, 1-26. (Year: 1996).*
Jason D. Buenrostro et al., "Transposition of native chromatin for fast and sensitive epigenomic profiling of open chromatin, DNA-binding proteins and nucleosome position", Nature Methods, Nature Publishing Group, GB, vol. 10, No. 12, Dec. 1, 2013, pp. 1213-1218.
Davies et al. "Three-Dimensional Structure of the Tn5 Synaptic Complex Transposition Intermediate", *Science* (2000), 289, p. 77-85.
Kyte et al., "A Simple Method for Displaying the Hydropathic Character of a Protein", *J. Mol. Biol.* (1982), 157, p. 105-132.
Lehninger, "The Amine Acid Building Blocks of Framing", *Biochemistry*, Second Edition, Chapter 4, (1975), p. 71-77.
Picelli et al. "Tn5 transposase and tagmentation procedures for massively scaled sequencing projects", *Genome Research*, (2014), 24, p. 2033-2040.
Reznikoff W.S. "Tn5 transposition: a molecular tool for studying protein structure-function", *Biochem. Soc. Trans.* (2006), 34, p. 320-323.
Reznikoff W.S. "Transposon Tn5", *Annu. Rev. Genet.* (2008), 42:269-286.
Tatusova et al., "BLAST 2 SEQUENCES, a new tool for comparing protein and nucleotide sequences", *FEMS Microbiol Lett.*, (1999), 174, 247-250.
Database NCBI (online), Accession No. WP_008608766, URL: https://www.ncbi.nlm.nih.gov/protein/495884187?sat=46&satkey=146477005 (Jul. 21, 2013).

(Continued)

*Primary Examiner* — Amy M Bunker
(74) *Attorney, Agent, or Firm* — Eric Grant Lee

(57) ABSTRACT

Disclosed is a method of fragmenting DNA comprising contacting a sample of target DNA with (a) a composition comprising an active transpososome, and (b) a composition comprising an inactive transpososome, under conditions suitable for transpososome activity, wherein a ratio of an amount of the inactive transpososome in the composition of (b) to an amount of the active transpososome in the composition of (a) determines the mean fragment size and a level of insertion bias.

2 Claims, 14 Drawing Sheets
(12 of 14 Drawing Sheet(s) Filed in Color)
Specification includes a Sequence Listing.

(56) References Cited

OTHER PUBLICATIONS

Naumann & Reznikoff, "Tn5 Transposase Active Site Mutants," The Journal of Biological Chemistry 277(20):17623-17629 (2002).
Jaejoon Jung, et al., "Genome Sequence of Pectin-Degrading Alishewanella aestuarii Strain B11T, Isolated from Tidal Flat Sediment," Journal of Bacteriology 194(19):5476 (2012).
William S. Reznikoff, "Tn5 as a model for understanding DNA transposition," Molecular Microbiology 47(5):1199-1206 (2003).
International Searching Authority, International Search Report for International Patent Application No. PCT/US2017/028293 (dated Oct. 26, 2017).
International Searching Authority, Written Opinion of the International Searching Authority for International Patent Application No. PCT/US2017/028293 (dated Oct. 26, 2017).
International Searching Authority, International Preliminary Report on Patentability for International Patent Application No. PCT/US2017/028293 (dated Nov. 1, 2018).
Munoz-Lopez, et al., "DNA Transposons: Nature and Applications in Genomics," Current Genomics 11:115-128 (2010).
Ohtsubo, et al., "Bacterial Insertion Sequences," Springer-Verlag Berlin Heidelberg 1-26 (1996).

\* cited by examiner

Comparison of expression and purification of different transposases.

Test of the tagmentation capabilities of TnAa-Tnp and TnVc-Tnp.

The effect of glycerol concentration on tagmentation efficiency.

- : 40% glycerol
- : 20% glycerol
- : 10% glycerol
- : 5% glycerol
- : 0% glycerol

The effect of the P47K mutation on tagmentation efficiency.

● : P47K mutant transpososome
● : Wild type transpososome

The effect of manganese concentration on tagmentation efficiency.

- : 1mM manganese
- : 0.25mM manganese
- : 0.065mM manganese
- : 0.025mM manganese
- : 0.0125mM manganese The effect of transpososome concentration on tagmentation efficiency.

Fragment size (base pairs)

✳ : 80ng transpososome
✳ : 40ng transpososome
✳ : 20ng transpososome
✳ : 10ng transpososome
✳ : 5ng transpososome

Schematic of tagmentation under different conditions.

A

B

C

Tagmentation by transpososomes containing modified DNA adapters/arms.

Effect on fragment size due to addition of inactive transpososomes.

A

Fragment size (base pairs)

✻ : 160ng active : 0ng inactive (1:0)
✻ : 160ng active : 80ng inactive (2:1)
✻ : 160ng active : 160ng inactive (1:1)

B

Fragment size (base pairs)

✻ : 80ng active : 0ng inactive (1:0)
✻ : 80ng active : 40ng inactive (2:1)
✻ : 80ng active : 80ng inactive (1:1)

Effect on sequencing library fragment size due to addition of inactive transpososome complexes.

Fragment size (base pairs)

✳ : 160ng active : 0ng inactive (1:0)
✳ : 160ng active : 80ng inactive (2:1)
✳ : 160ng active : 160ng inactive (1:1)
✳ : 160ng active : 360ng inactive (1:2.5)

Library insert sizes based on read mapping locations.

* : 160ng active : 0ng inactive (1:0)
* : 160ng active : 80ng inactive (2:1)
* : 160ng active : 160ng inactive (1:1)
* : 160ng active : 360ng inactive (1:2.5)

Tagmentation insertion site biases.

SEQUENCE LISTING

<160> NUMBER OF SEQ ID NOS: 58

<210> SEQ ID NO 1
<211> LENGTH: 476
<212> TYPE: PRT
<213> ORGANISM: Artificial Sequence
<220> FEATURE:
<223> OTHER INFORMATION: Synthetic Polypeptide

<400> SEQUENCE: 1

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
                100                 105                 110

Lys Leu Gly Ser Ile Gln Asp Lys Ser Arg Gly Trp Trp Val His Ser
            115                 120                 125

Val Leu Leu Leu Glu Ala Thr Thr Phe Arg Thr Val Gly Leu Leu His
            130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
                180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
                260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
            290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
                340                 345                 350

Val Ser Ile Leu Ser Phe Val Ala Val Arg Leu Leu Gln Leu Arg Glu
            355                 360                 365

Ser Phe Thr Pro Pro Gln Ala Leu Arg Ala Gln Gly Leu Leu Lys Glu
            370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 2
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 2

Met Asn Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
            20                  25                  30

Ala Asn Asp Pro Gly Lys Pro Phe Val Ser Ile Thr Gln Ser Pro Ala
        35                  40                  45

Asp Met Glu Gly Ala Tyr Arg Phe Ile Arg Asn Glu His Val Asn Ala
    50                  55                  60

Asp Ala Ile Ala Lys Ala Gly Tyr Leu Val Thr Ala Ala Gln Ala Ala
65                  70                  75                  80

Lys His Asn Leu Leu Ala Leu Glu Asp Thr Thr Ala Ile Thr Tyr
                85                  90                  95

Ser His Arg Ser Val Arg Asp Glu Leu Gly His Val Asn Gln Gly Asn
            100                 105                 110

Asn Tyr Arg Gly Ile Leu Ala His Ser Val Leu Leu Phe Ala Pro Glu
        115                 120                 125

Gln Gln Glu Leu Val Gly Leu Ile Glu Gln Ser Arg Trp Thr Arg Asp
    130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
                165                 170                 175

Arg Leu Gly Thr Lys Met Ala Asp Val Ile Ser Val Cys Asp Arg Glu
            180                 185                 190

Ala Asp Ile Tyr Glu Tyr Leu Gln Tyr Lys Leu Ser Lys Gln His Arg
        195                 200                 205

Phe Val Val Arg Ser Met Gln Ser Arg His Ile Glu Gln Ser Glu Gln
    210                 215                 220

Lys Leu Tyr Asp Tyr Ala Ala Gly Leu Glu Ser Ala Gly Gln Lys Gln
225                 230                 235                 240

Ile His Ile Ala Gln Lys Gly Gly Arg Lys Ala Arg Thr Ala Thr Val
                245                 250                 255

Asp Ile Val Phe Ala Pro Val Thr Leu Gln Val Pro Ala Asn Lys Arg
            260                 265                 270

Gly Glu Ser Leu Ser Leu Tyr Tyr Val Gly Cys Glu Glu Arg Ala Asp
        275                 280                 285

Asp Lys Asn Ala Leu Asn Trp His Leu Leu Thr Thr Glu Pro Val Gln
    290                 295                 300

Ser Lys Ala Asp Ala Leu Asn Ile Ile Arg Tyr Tyr Glu His Arg Trp
305                 310                 315                 320

Leu Val Glu Glu Tyr His Lys Ala Trp Lys Thr Asp Gly Thr Asp Ile
                325                 330                 335

Glu Asn Ala Arg Leu Gln Ser Lys Asp Asn Ile Glu Arg Leu Val Thr
            340                 345                 350

```
Ile Ser Ala Phe Ile Ala Val Arg Ile Val Gln Leu Lys Phe Ala Arg
            355                 360                 365

Glu Gln Pro Asp Glu Ile Ser Cys Gln Val Leu Ser Pro Lys Ala
    370                 375                 380

Trp Lys Leu Leu Trp Ile Lys Arg Val Ser Arg Thr Leu Pro Asp Thr
385                 390                 395                 400

Val Pro Ser Met Lys Trp Ala Tyr Thr Glu Leu Ala Lys Leu Gly Gly
                405                 410                 415

Trp Lys Asp Thr Lys Gln Thr Gly Lys Ala Ser Val Lys Val Leu Trp
            420                 425                 430

Gln Gly Trp Phe Lys Leu Gln Thr Ile Leu Glu Gly Tyr Asp Leu Ala
            435                 440                 445

Lys Ser Leu Glu Ala Asp Leu
    450                 455

<210> SEQ ID NO 3
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 3

Met Asn Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
                20                  25                  30

Ala Asn Asp Pro Gly Lys Pro Phe Val Ser Ile Thr Gln Ser Pro Ala
            35                  40                  45

Asp Met Glu Gly Ala Tyr Arg Phe Ile Arg Asn Glu His Val Asn Ala
        50                  55                  60

Asp Ala Ile Ala Lys Ala Gly Tyr Leu Val Thr Ala Ala Gln Ala Ala
65                  70                  75                  80

Lys His Asn Leu Leu Leu Ala Leu Glu Asp Thr Thr Ala Ile Thr Tyr
                85                  90                  95

Ser His Arg Ser Val Arg Asp Glu Leu Gly His Val Asn Gln Gly Asn
            100                 105                 110

Asn Tyr Arg Gly Ile Leu Ala His Ser Val Leu Leu Phe Ala Pro Glu
        115                 120                 125

Gln Gln Glu Leu Val Gly Leu Ile Glu Gln Ser Arg Trp Thr Arg Asp
130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
                165                 170                 175

Arg Leu Gly Thr Lys Met Ala Asp Val Ile Ser Val Cys Asp Arg Glu
            180                 185                 190

Ala Asp Ile Tyr Glu Tyr Leu Gln Tyr Lys Leu Ser Lys Gln His Arg
        195                 200                 205

Phe Val Val Arg Ser Met Gln Ser Arg His Ile Glu Gln Ser Glu Gln
    210                 215                 220

Lys Leu Tyr Asp Tyr Ala Ala Gly Leu Glu Ser Ala Gly Gln Lys Gln
225                 230                 235                 240

Ile His Ile Ala Gln Lys Gly Gly Arg Lys Ala Arg Thr Ala Thr Val
                245                 250                 255
```

```
Asp Ile Val Phe Ala Pro Val Thr Leu Gln Val Pro Ala Asn Lys Arg
            260                 265                 270

Gly Glu Ser Leu Ser Leu Tyr Tyr Val Gly Cys Glu Glu Arg Ala Asp
        275                 280                 285

Asp Lys Asn Ala Leu Asn Trp His Leu Leu Thr Thr Glu Pro Val Gln
    290                 295                 300

Ser Lys Ala Asp Ala Leu Asn Ile Ile Arg Tyr Tyr Glu His Arg Trp
305                 310                 315                 320

Leu Val Glu Glu Tyr His Lys Ala Trp Lys Thr Asp Gly Thr Asp Ile
                325                 330                 335

Glu Asn Ala Arg Leu Gln Ser Lys Asp Asn Ile Glu Arg Leu Val Thr
            340                 345                 350

Ile Ser Ala Phe Ile Ala Val Arg Ile Val Gln Leu Lys Phe Ala Arg
        355                 360                 365

Glu Gln Pro Asp Glu Ile Ser Cys Glu Gln Val Leu Ser Pro Lys Ala
    370                 375                 380

Trp Lys Leu Leu Trp Ile Lys Arg Val Ser Arg Thr Leu Pro Asp Thr
385                 390                 395                 400

Val Pro Ser Met Lys Trp Ala Tyr Thr Glu Leu Ala Lys Leu Gly Gly
                405                 410                 415

Trp Lys Asp Thr Lys Gln Thr Gly Lys Ala Ser Val Lys Val Leu Trp
            420                 425                 430

Gln Gly Trp Phe Lys Leu Gln Thr Ile Leu Glu Gly Tyr Asp Leu Ala
        435                 440                 445

Lys Ser Leu Glu Ala Asp Leu
    450                 455

<210> SEQ ID NO 4
<211> LENGTH: 476
<212> TYPE: PRT
<213> ORGANISM: Artificial Sequence
<220> FEATURE:
<223> OTHER INFORMATION: Synthetic Polypeptide

<400> SEQUENCE: 4

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160
```

Glu Ser Gly Met Trp Leu Ala Ala Ala Thr Ser Arg Leu Arg Met
            165                 170                 175

Gly Ser Met Met Ser Asn Val Ile Ala Val Cys Asp Arg Glu Ala Asp
        180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
        210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
            245                 250                 255

Pro Ala Arg Lys Ala Ser Leu Ser Leu Arg Ser Gly Arg Ile Thr Leu
        260                 265                 270

Lys Gln Gly Asn Ile Thr Leu Asn Ala Val Leu Ala Glu Glu Ile Asn
    275                 280                 285

Pro Pro Lys Gly Glu Thr Pro Leu Lys Trp Leu Leu Thr Ser Glu
        290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
            325                 330                 335

Gly Ala Glu Arg Gln Arg Met Glu Glu Pro Asp Asn Leu Glu Arg Met
        340                 345                 350

Val Ser Ile Leu Ser Phe Val Ala Val Arg Leu Leu Gln Leu Arg Glu
    355                 360                 365

Ser Phe Thr Pro Pro Gln Ala Leu Arg Ala Gln Gly Leu Leu Lys Glu
370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
            405                 410                 415

Glu Lys Ala Gly Ser Leu Gln Trp Ala Tyr Met Ala Ile Ala Arg Leu
        420                 425                 430

Gly Gly Phe Met Asp Ser Lys Arg Thr Gly Ile Ala Ser Trp Gly Ala
    435                 440                 445

Leu Trp Glu Gly Trp Glu Ala Leu Gln Ser Lys Leu Asp Gly Phe Leu
450                 455                 460

Ala Ala Lys Asp Leu Met Ala Gln Gly Ile Lys Ile
465                 470                 475

<210> SEQ ID NO 5
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 5
agatgtgtat aagagacag                                                19

<210> SEQ ID NO 6
<211> LENGTH: 19
<212> TYPE: DNA
<213> ORGANISM: Artificial Sequence
<220> FEATURE:
<223> OTHER INFORMATION: Synthetic Polynucleotide -continued

```
<400> SEQUENCE: 6
tctacacata ttctctgtc                                                19

<210> SEQ ID NO 7
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (19)..(19)
<223> OTHER INFORMATION: modification may include 3'-H, 3'-phosphate,
      3'-bulky group selected from the group consisting of a hexanediol,
      a 3-carbon spacer, a triethylene glycol, a hexa-ethyleneglycol,
      and any combination thereof.

<400> SEQUENCE: 7
agatgtgtat aagagacag                                                19

<210> SEQ ID NO 8
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 8
tctacacata ttctctgtc                                                19

<210> SEQ ID NO 9
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (19)..(19)
<223> OTHER INFORMATION: modification is a 3'-H

<400> SEQUENCE: 9
agatgtgtat aagagacag                                                19

<210> SEQ ID NO 10
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 10
tctacacata ttctctgtc                                                19

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: modification is a 3'-phosphate

<400> SEQUENCE: 11
agatgtgtat aagagacag                                                19
```

```
<210> SEQ ID NO 12
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 12
tctacacata ttctctgtc                                              19

<210> SEQ ID NO 13
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: N may include a synthetic base, a nucleotide
      analog (e.g. a locked nucleic acid, a bridged nucleic acid, or a
      xeno nucleic acid), an inverted base, or an abasic site.

<400> SEQUENCE: 13
agatgtgtat aagagacan                                              19

<210> SEQ ID NO 14
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 14
tctacacata ttctctgtc                                              19

<210> SEQ ID NO 15
<211> LENGTH: 476
<212> TYPE: PRT
<213> ORGANISM: Artificial Sequence
<220> FEATURE:
<223> OTHER INFORMATION: Synthetic Polypeptide

<400> SEQUENCE: 15
```

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
            165                 170                 175

Gly Ser Met Met Ser Asn Val Ile Ala Val Cys Asp Arg Glu Ala Asp
        180                 185                 190

Ile His Ala Tyr Leu Gln Asp Lys Leu Ala His Asn Glu Arg Phe Val
    195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 16
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 16

Met Asn Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
            20                  25                  30

```
Ala Asn Asp Pro Gly Lys Pro Phe Val Ser Ile Thr Gln Ser Pro Ala
         35                  40                  45

Asp Met Glu Gly Ala Tyr Arg Phe Ile Arg Asn Glu His Val Asn Ala
     50                  55                  60

Asp Ala Ile Ala Lys Ala Gly Tyr Leu Val Thr Ala Ala Gln Ala Ala
 65                  70                  75                  80

Lys His Asn Leu Leu Leu Ala Leu Glu Asp Thr Thr Ala Ile Thr Tyr
                 85                  90                  95

Ser His Arg Ser Val Arg Asp Glu Leu Gly His Val Asn Gln Gly Asn
                100                 105                 110

Asn Tyr Arg Gly Ile Leu Ala His Ser Val Leu Leu Phe Ala Pro Glu
            115                 120                 125

Gln Gln Glu Leu Val Gly Leu Ile Glu Gln Ser Arg Trp Thr Arg Asp
        130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
                    165                 170                 175

Arg Leu Gly Thr Lys Met Ala Asp Val Ile Ser Val Cys Asp Arg Glu
                180                 185                 190

Ala Asp Ile Tyr Glu Tyr Leu Gln Tyr Lys Leu Ser Lys Gln His Arg
            195                 200                 205

Phe Val Val Arg Ser Met Gln Ser Arg His Ile Glu Gln Ser Glu Gln
        210                 215                 220

Lys Leu Tyr Asp Tyr Ala Ala Gly Leu Glu Ser Ala Gly Gln Lys Gln
225                 230                 235                 240

Ile His Ile Ala Gln Lys Gly Gly Arg Lys Ala Arg Thr Ala Thr Val
                245                 250                 255

Asp Ile Val Phe Ala Pro Val Thr Leu Gln Val Pro Ala Asn Lys Arg
            260                 265                 270

Gly Glu Ser Leu Ser Leu Tyr Tyr Val Gly Cys Glu Arg Ala Asp
        275                 280                 285

Asp Lys Asn Ala Leu Asn Trp His Leu Leu Thr Thr Glu Pro Val Gln
    290                 295                 300

Ser Lys Ala Asp Ala Leu Asn Ile Ile Arg Tyr Tyr Glu His Arg Trp
305                 310                 315                 320

Leu Val Glu Glu Tyr His Lys Ala Trp Lys Thr Asp Gly Thr Asp Ile
                325                 330                 335

Glu Asn Ala Arg Leu Gln Ser Lys Asp Asn Ile Glu Arg Leu Val Thr
            340                 345                 350

Ile Ser Ala Phe Ile Ala Val Arg Ile Val Gln Leu Lys Phe Ala Arg
        355                 360                 365

Glu Gln Pro Asp Glu Ile Ser Cys Glu Gln Val Leu Ser Pro Lys Ala
    370                 375                 380

Trp Lys Leu Leu Trp Ile Lys Arg Val Ser Arg Thr Leu Pro Asp Thr
385                 390                 395                 400

Val Pro Ser Met Lys Trp Ala Tyr Thr Glu Leu Ala Lys Leu Gly Gly
                    405                 410                 415

Trp Lys Asp Thr Lys Gln Thr Gly Lys Ala Ser Val Lys Val Leu Trp
                420                 425                 430

Gln Gly Trp Phe Lys Leu Gln Thr Ile Leu Glu Gly Tyr Asp Leu Ala
            435                 440                 445
```

```
Lys Ser Leu Glu Ala Asp Leu
    450                 455

<210> SEQ ID NO 17
<211> LENGTH: 461
<212> TYPE: PRT
<213> ORGANISM: Artificial Sequence
<220> FEATURE:
<223> OTHER INFORMATION: Synthetic Polypeptide

<400> SEQUENCE: 17

Met Thr Tyr Ile Glu Pro Thr Leu Trp Ala Gln Lys Gln Phe Gly Gln
1               5                   10                  15

Ala His Leu Asn Asp Pro Arg Arg Thr Gln Arg Leu Val Ala Leu Ala
            20                  25                  30

Ala Ser Leu Ala Glu Gln Pro Gly Val Pro Val Ser Lys Leu Ile Ile
        35                  40                  45

Ser Pro Ala Asp Met Glu Gly Ala Tyr Arg Phe Ile Arg Asn Glu Gln
    50                  55                  60

Ile Lys Ala Glu Asp Ile Ala Glu Ala Gly Phe His Val Thr Ala Gln
65                  70                  75                  80

Glu Ala Leu Glu Gln Gln Thr Leu Leu Ala Leu Glu Asp Thr Thr Ser
                85                  90                  95

Leu Ser Tyr Ser His Arg Ser Ile Gln Asp Glu Leu Gly His Ser Asn
            100                 105                 110

Gln Gly Asn Arg Asn Arg Ala Met Phe Ile His Ser Thr Leu Leu Phe
        115                 120                 125

Ala Pro Glu Thr Gln Val Val Gly Leu Ile Glu Gln Gln Arg Trp
    130                 135                 140

Thr Arg Asp Ile Glu Lys Arg Gly Gln Gly His Gln Tyr Ala Thr Arg
145                 150                 155                 160

Pro Tyr Lys Glu Lys Glu Ser Tyr Lys Trp Glu Gln Ala Ser Arg His
                165                 170                 175

Val Ala Glu Arg Leu Gly Asp Lys Ile Ser Asp Val Ile Ser Val Cys
            180                 185                 190

Asp Arg Glu Ala Asp Leu Phe Glu Tyr Leu Thr Tyr Lys Gln Glu Gln
        195                 200                 205

Gln Gln Arg Phe Leu Val Arg Ser Met Gln Ser Arg Cys Ile Glu Glu
    210                 215                 220

His Asp Asn Arg Leu Tyr Asp Tyr Ala Ser Lys Leu Gln Ser Ala Gly
225                 230                 235                 240

Glu Arg Val Leu Asp Ile Pro Gln Lys Gly Arg Lys Ala Arg Thr
                245                 250                 255

Val His Leu Asp Ile Lys Tyr Ala Pro Val Thr Leu Lys Ser Pro Ala
            260                 265                 270

Asn Lys Lys Glu Phe Asn Asn Ile Pro Leu Tyr Tyr Val Gly Cys Ile
        275                 280                 285

Glu Gln Gly Glu Ser Asn Asp Lys Leu Ala Trp His Leu Leu Thr Ser
    290                 295                 300

Glu Pro Ile Thr Ser Lys Glu Glu Ala Leu Lys Ile Val Ser Tyr Tyr
305                 310                 315                 320

Glu Leu Arg Trp Leu Ile Glu Asp Phe His Lys Val Trp Lys Ser Glu
                325                 330                 335

Gly Thr Gln Val Glu Gln Leu Arg Met Gln Ser Lys Asp Asn Leu Glu
            340                 345                 350
```

```
Arg Leu Ser Val Ile Leu Ala Phe Ile Ala Thr Arg Leu Gln Leu
            355                 360                 365

Arg Phe Met Asn Glu Ser Asp Glu Leu Ser Lys Ser Ser Cys Glu Pro
370                 375                 380

Ile Leu Lys Gly Lys Ala Trp Lys Leu Met Trp Leu Lys Leu Glu Arg
385                 390                 395                 400

Lys Gly Leu Pro Lys Glu Ala Pro Asp Ile Ser Trp Ala Tyr Lys Gly
                405                 410                 415

Ile Ala Arg Leu Gly Gly Trp Lys Asn Thr Lys Arg Thr Gly Arg Ala
            420                 425                 430

Ser Ile Lys Thr Leu Trp Gln Gly Trp Phe Arg Leu Gln Thr Ile Leu
            435                 440                 445

Glu Gly Tyr Glu Leu Ala Lys Ser Leu Asp Ser Pro Asp
    450                 455                 460

<210> SEQ ID NO 18
<211> LENGTH: 459
<212> TYPE: PRT
<213> ORGANISM: Artificial Sequence
<220> FEATURE:
<223> OTHER INFORMATION: Synthetic Polypeptide

<400> SEQUENCE: 18

Met Thr His Ser Asp Ala Lys Leu Trp Ala Gln Glu Gln Phe Gly Gln
1               5                   10                  15

Ala Gln Leu Lys Asp Pro Arg Arg Thr Gln Arg Leu Ile Ser Leu Ala
            20                  25                  30

Thr Ser Ile Ala Asn Gln Pro Gly Val Ser Val Ala Lys Leu Pro Phe
        35                  40                  45

Ser Pro Ala Asp Met Glu Gly Ala Tyr Arg Phe Ile Arg Asn Glu Asn
50                  55                  60

Ile Asn Ala Glu Asp Ile Ala Glu Ala Gly Phe Gln Ser Thr Val Ser
65                  70                  75                  80

Arg Ala Asn Glu His Lys Glu Leu Leu Ala Leu Glu Asp Thr Thr Thr
                85                  90                  95

Leu Ser Phe Pro His Arg Ser Ile Lys Glu Glu Leu Gly His Thr Asn
            100                 105                 110

Gln Gly Asp Arg Thr Arg Ala Leu His Val His Ser Thr Leu Leu Phe
        115                 120                 125

Ala Pro Gln Ser Gln Thr Ile Val Gly Leu Ile Glu Gln Gln Arg Trp
130                 135                 140

Ser Arg Asp Ile Thr Lys Arg Gly Gln Lys His Gln His Ala Thr Arg
145                 150                 155                 160

Pro Tyr Lys Glu Lys Glu Ser Tyr Lys Trp Glu Gln Ala Ser Arg Arg
                165                 170                 175

Val Val Glu Arg Leu Gly Asp Lys Met Leu Asp Val Ile Ser Val Cys
            180                 185                 190

Asp Arg Glu Ala Asp Leu Phe Glu Tyr Leu Thr Tyr Lys Arg Gln His
        195                 200                 205

Gln Gln Arg Phe Val Val Arg Ser Met Gln Ser Arg Cys Leu Glu Glu
    210                 215                 220

His Ala Gln Lys Leu Tyr Asp Tyr Ala Gln Ala Leu Pro Ser Val Glu
225                 230                 235                 240

Thr Lys Ala Leu Thr Ile Pro Gln Lys Gly Gly Arg Lys Ala Arg Asn
                245                 250                 255
```

```
Val Lys Leu Asp Val Lys Tyr Gly Gln Val Thr Leu Lys Ala Pro Ala
            260                 265                 270

Asn Lys Lys Glu His Ala Gly Ile Pro Val Tyr Tyr Val Gly Cys Leu
        275                 280                 285

Glu Gln Gly Thr Ser Lys Asp Lys Leu Ala Trp His Leu Leu Thr Ser
    290                 295                 300

Glu Pro Ile Asn Asn Val Asp Asp Ala Met Arg Ile Ile Gly Tyr Tyr
305                 310                 315                 320

Glu Arg Arg Trp Leu Ile Glu Asp Phe His Lys Val Trp Lys Ser Glu
                325                 330                 335

Gly Thr Asp Val Glu Ser Leu Arg Leu Gln Ser Lys Asp Asn Leu Glu
            340                 345                 350

Arg Leu Ser Val Ile Tyr Ala Phe Val Ala Thr Arg Leu Leu Ala Leu
        355                 360                 365

Arg Phe Met Lys Glu Val Asp Glu Leu Thr Lys Glu Ser Cys Glu Lys
    370                 375                 380

Val Leu Gly Gln Lys Ala Trp Lys Leu Leu Trp Leu Lys Leu Glu Ser
385                 390                 395                 400

Lys Thr Leu Pro Lys Glu Val Pro Asp Met Gly Trp Ala Tyr Lys Asn
                405                 410                 415

Leu Ala Lys Leu Gly Gly Trp Lys Asp Thr Lys Arg Thr Gly Arg Ala
            420                 425                 430

Ser Ile Lys Val Leu Trp Glu Gly Trp Phe Lys Leu Gln Thr Ile Leu
        435                 440                 445

Glu Gly Tyr Glu Leu Ala Met Ser Leu Asp His
    450                 455

<210> SEQ ID NO 19
<211> LENGTH: 457
<212> TYPE: PRT
<213> ORGANISM: Artificial Sequence
<220> FEATURE:
<223> OTHER INFORMATION: Synthetic Polypeptide

<400> SEQUENCE: 19

Met Ile Lys Ser Asn Asn Asp Trp Ala Glu Glu Gln Phe Gly His Ala
1               5                   10                  15

Lys Leu Gly Asp Pro Arg Arg Thr Ala Arg Leu Val Lys Met Ala Ser
            20                  25                  30

Asp Leu Ala Gln His Pro Gly Lys Ser Val Val Lys Ser Ser Pro Ser
        35                  40                  45

Pro Ala Ser Met Glu Gly Ala Tyr Arg Phe Ile Arg Asn Asp Asn Val
    50                  55                  60

Ser Ala Asp Asp Ile Ala Glu Ala Gly Phe Arg Ala Thr Val Asn Gln
65                  70                  75                  80

Ala His Arg Tyr Pro Leu Leu Leu Ala Ile Glu Asp Thr Thr Thr Leu
                85                  90                  95

Ser Tyr Lys His Arg Ser Ile Arg Ala Asp Leu Gly His Val Asn Gln
            100                 105                 110

Gly Asn Arg Tyr Arg Gly Leu Leu Ala His Ser Ile Leu Leu Phe Ala
        115                 120                 125

Pro Glu Thr Leu Asp Val Val Gly Leu Ile Glu Gln His Arg Trp Thr
    130                 135                 140

Arg Asp Ile Lys Thr Arg Gly Ile Arg Arg Glu Asn Leu Lys Arg Pro
145                 150                 155                 160
```

-continued

Tyr Glu Glu Lys Glu Gly Tyr Lys Trp Glu Ser Ala Ser Arg Asn Met
            165                 170                 175

Ala Ala Arg Leu Gly Thr Ala Met Ala Asn Val Ile Ser Val Cys Asp
        180                 185                 190

Arg Glu Ala Asp Ile Tyr Asp Tyr Leu Leu Tyr Lys Ile Ala Asn Gln
    195                 200                 205

Gln Arg Phe Val Val Arg Ser Met Met Ser Arg His Ile Glu Glu Gly
210                 215                 220

Ser Asp Lys Leu Tyr His Phe Ala Ser Glu Leu Asn Ser Val Lys Gln
225                 230                 235                 240

Arg Gln Ile Gln Ile Ala Gln Arg Gly Gly Arg Lys Ala Arg Glu Val
            245                 250                 255

Thr Leu Asp Val Lys Tyr Ala Ala Val Thr Leu Lys Thr Pro Ala Asn
        260                 265                 270

Lys Lys Gly Ser Pro Ile Ser Leu Asn Tyr Val Gly Cys Ser Glu Val
    275                 280                 285

Gly Asp Glu Glu Lys Thr Leu Asn Trp His Ile Leu Thr Asn Glu Pro
290                 295                 300

Val Asn Ser Ala Glu Asp Ala Leu Lys Ile Ile Gly Tyr Tyr Glu Lys
305                 310                 315                 320

Arg Trp Leu Ile Glu Glu Tyr His Lys Val Trp Lys Ser Glu Gly Thr
            325                 330                 335

Gly Val Glu Asp Leu Arg Val Gln Ser Lys Asp Asn Leu Asp Arg Leu
        340                 345                 350

Ala Thr Ile Tyr Ala Phe Leu Ala Val Arg Ile Phe Gln Leu Lys Phe
    355                 360                 365

Ala Asn Glu Gln Ile Glu Asp Ile Ser Ser Glu Lys Ile Leu Ser Pro
370                 375                 380

Arg Ala Trp Lys Leu Leu Trp Leu Lys Arg Ile Lys Thr Pro Pro Pro
385                 390                 395                 400

Glu Glu Val Pro Thr Ala Lys Trp Ala Tyr Glu His Leu Ala Arg Leu
            405                 410                 415

Gly Gly Trp Lys Asp Ser Lys Arg Asn Gly Arg Ala Ser Val Lys Thr
        420                 425                 430

Leu Trp Glu Gly Trp Leu Lys Leu Gln Ala Ile Leu Glu Gly Tyr Glu
    435                 440                 445

Leu Ala Leu Ser Leu Glu Gln Asp Leu
    450                 455

<210> SEQ ID NO 20
<211> LENGTH: 342
<212> TYPE: PRT
<213> ORGANISM: Artificial Sequence
<220> FEATURE:
<223> OTHER INFORMATION: Synthetic Polypeptide

<400> SEQUENCE: 20

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Ile
    50                  55                  60

```
Arg Asn Pro Asn Val Ser Ala Glu Ala Ile Arg Lys Ala Gly Ala Met
 65                  70                  75                  80

Gln Thr Val Lys Leu Ala Gln Glu Phe Pro Glu Leu Leu Ala Ile Glu
             85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
            115                 120                 125

Val Leu Leu Leu Glu Ala Thr Thr Phe Arg Thr Val Gly Leu Leu His
            130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
                180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Ile Thr Leu
                260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg
            340

<210> SEQ ID NO 21
<211> LENGTH: 342
<212> TYPE: PRT
<213> ORGANISM: Artificial Sequence
<220> FEATURE:
<223> OTHER INFORMATION: Synthetic Polypeptide

<400> SEQUENCE: 21

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
        50                  55                  60

Arg Asn Pro Asn Val Ser Ala Glu Ala Ile Arg Lys Ala Gly Ala Met
 65                 70                  75                  80
```

```
Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
                180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
        210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
                260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg
            340

<210> SEQ ID NO 22
<211> LENGTH: 340
<212> TYPE: PRT
<213> ORGANISM: Alishewanella aestruarii

<400> SEQUENCE: 22

Met Asn Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
            20                  25                  30

Ala Asn Asp Pro Gly Lys Pro Phe Val Ser Ile Thr Gln Ser Pro Ala
        35                  40                  45

Asp Met Glu Gly Ala Tyr Arg Phe Ile Arg Asn Glu His Val Asn Ala
    50                  55                  60

Asp Ala Ile Ala Lys Ala Gly Tyr Leu Val Thr Ala Ala Gln Ala Ala
65                  70                  75                  80

Lys His Asn Leu Leu Leu Ala Leu Glu Asp Thr Thr Ala Ile Thr Tyr
                85                  90                  95

Ser His Arg Ser Val Arg Asp Glu Leu Gly His Val Asn Gln Gly Asn
            100                 105                 110
```

```
Asn Tyr Arg Gly Ile Leu Ala His Ser Val Leu Leu Phe Ala Pro Glu
        115                 120                 125

Gln Gln Glu Leu Val Gly Leu Ile Glu Gln Ser Arg Trp Thr Arg Asp
    130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
                165                 170                 175

Arg Leu Gly Thr Lys Met Ala Asp Val Ile Ser Val Cys Asp Arg Glu
            180                 185                 190

Ala Asp Ile Tyr Glu Tyr Leu Gln Tyr Lys Leu Ser Lys Gln His Arg
        195                 200                 205

Phe Val Val Arg Ser Met Gln Ser Arg His Ile Glu Gln Ser Glu Gln
    210                 215                 220

Lys Leu Tyr Asp Tyr Ala Ala Gly Leu Glu Ser Ala Gly Gln Lys Gln
225                 230                 235                 240

Ile His Ile Ala Gln Lys Gly Gly Arg Lys Ala Arg Thr Ala Thr Val
                245                 250                 255

Asp Ile Val Phe Ala Pro Val Thr Leu Gln Val Pro Ala Asn Lys Arg
            260                 265                 270

Gly Glu Ser Leu Ser Leu Tyr Tyr Val Gly Cys Glu Glu Arg Ala Asp
        275                 280                 285

Asp Lys Asn Ala Leu Asn Trp His Leu Leu Thr Thr Glu Pro Val Gln
    290                 295                 300

Ser Lys Ala Asp Ala Leu Asn Ile Ile Arg Tyr Tyr Glu His Arg Trp
305                 310                 315                 320

Leu Val Glu Glu Tyr His Lys Ala Trp Lys Thr Asp Gly Thr Asp Ile
                325                 330                 335

Glu Asn Ala Arg
            340

<210> SEQ ID NO 23
<211> LENGTH: 342
<212> TYPE: PRT
<213> ORGANISM: Artificial Sequence
<220> FEATURE:
<223> OTHER INFORMATION: Synthetic Polypeptide

<400> SEQUENCE: 23

Met Ile Lys Ser Asn Asn Asp Trp Ala Glu Glu Gln Phe Gly His Ala
1               5                   10                  15

Lys Leu Gly Asp Pro Arg Arg Thr Ala Arg Leu Val Lys Met Ala Ser
            20                  25                  30

Asp Leu Ala Gln His Pro Gly Lys Ser Val Val Lys Ser Ser Pro Ser
        35                  40                  45

Pro Ala Ser Met Glu Gly Ala Tyr Arg Phe Ile Arg Asn Asp Asn Val
    50                  55                  60

Ser Ala Asp Asp Ile Ala Glu Ala Gly Phe Arg Ala Thr Val Asn Gln
65                  70                  75                  80

Ala His Arg Tyr Pro Leu Leu Leu Ala Ile Glu Asp Thr Thr Thr Leu
                85                  90                  95

Ser Tyr Lys His Arg Ser Ile Arg Ala Asp Leu Gly His Val Asn Gln
            100                 105                 110

Gly Asn Arg Tyr Arg Gly Leu Leu Ala His Ser Ile Leu Leu Phe Ala
        115                 120                 125
```

Pro Glu Thr Leu Asp Val Val Gly Leu Ile Glu Gln His Arg Trp Thr
    130                 135                 140

Arg Asp Ile Lys Thr Arg Gly Ile Arg Arg Glu Asn Leu Lys Arg Pro
145                 150                 155                 160

Tyr Glu Glu Lys Glu Gly Tyr Lys Trp Glu Ser Ala Ser Arg Asn Met
                165                 170                 175

Ala Ala Arg Leu Gly Thr Ala Met Ala Asn Val Ile Ser Val Cys Asp
            180                 185                 190

Arg Glu Ala Asp Ile Tyr Asp Tyr Leu Leu Tyr Lys Ile Ala Asn Gln
        195                 200                 205

Gln Arg Phe Val Val Arg Ser Met Met Ser Arg His Ile Glu Glu Gly
    210                 215                 220

Ser Asp Lys Leu Tyr His Phe Ala Ser Glu Leu Asn Ser Val Lys Gln
225                 230                 235                 240

Arg Gln Ile Gln Ile Ala Gln Arg Gly Gly Arg Lys Ala Arg Glu Val
                245                 250                 255

Thr Leu Asp Val Lys Tyr Ala Ala Val Thr Leu Lys Thr Pro Ala Asn
            260                 265                 270

Lys Lys Gly Ser Pro Ile Ser Leu Asn Tyr Val Gly Cys Ser Glu Val
        275                 280                 285

Gly Asp Glu Glu Lys Thr Leu Asn Trp His Ile Leu Thr Asn Glu Pro
    290                 295                 300

Val Asn Ser Ala Glu Asp Ala Leu Lys Ile Ile Gly Tyr Tyr Glu Lys
305                 310                 315                 320

Arg Trp Leu Ile Glu Glu Tyr His Lys Val Trp Lys Ser Glu Gly Thr
                325                 330                 335

Gly Val Glu Asp Leu Arg
            340

<210> SEQ ID NO 24
<211> LENGTH: 344
<212> TYPE: PRT
<213> ORGANISM: Artificial Sequence
<220> FEATURE:
<223> OTHER INFORMATION: Synthetic Polypeptide

<400> SEQUENCE: 24

Met Thr Tyr Ile Glu Pro Thr Leu Trp Ala Gln Lys Gln Phe Gly Gln
1               5                   10                  15

Ala His Leu Asn Asp Pro Arg Arg Thr Gln Arg Leu Val Ala Leu Ala
            20                  25                  30

Ala Ser Leu Ala Glu Gln Pro Gly Val Pro Val Ser Lys Leu Ile Ile
        35                  40                  45

Ser Pro Ala Asp Met Glu Gly Ala Tyr Arg Phe Ile Arg Asn Glu Gln
    50                  55                  60

Ile Lys Ala Glu Asp Ile Ala Glu Ala Gly Phe His Val Thr Ala Gln
65                  70                  75                  80

Glu Ala Leu Glu Gln Gln Thr Leu Leu Ala Leu Glu Asp Thr Thr Ser
                85                  90                  95

Leu Ser Tyr Ser His Arg Ser Ile Gln Asp Glu Leu Gly His Ser Asn
            100                 105                 110

Gln Gly Asn Arg Asn Arg Ala Met Phe Ile His Ser Thr Leu Leu Phe
        115                 120                 125

Ala Pro Glu Thr Gln Val Val Gly Leu Ile Glu Gln Gln Arg Trp
    130                 135                 140

```
Thr Arg Asp Ile Glu Lys Arg Gly Gln Gly His Gln Tyr Ala Thr Arg
145                 150                 155                 160

Pro Tyr Lys Glu Lys Glu Ser Tyr Lys Trp Glu Gln Ala Ser Arg His
                165                 170                 175

Val Ala Glu Arg Leu Gly Asp Lys Ile Ser Asp Val Ile Ser Val Cys
            180                 185                 190

Asp Arg Glu Ala Asp Leu Phe Glu Tyr Leu Thr Tyr Lys Gln Glu Gln
        195                 200                 205

Gln Gln Arg Phe Leu Val Arg Ser Met Gln Ser Arg Cys Ile Glu Glu
    210                 215                 220

His Asp Asn Arg Leu Tyr Asp Tyr Ala Ser Lys Leu Gln Ser Ala Gly
225                 230                 235                 240

Glu Arg Val Leu Asp Ile Pro Gln Lys Gly Arg Lys Ala Arg Thr
                245                 250                 255

Val His Leu Asp Ile Lys Tyr Ala Pro Val Thr Leu Lys Ser Pro Ala
            260                 265                 270

Asn Lys Lys Glu Phe Asn Asn Ile Pro Leu Tyr Tyr Val Gly Cys Ile
        275                 280                 285

Glu Gln Gly Glu Ser Asn Asp Lys Leu Ala Trp His Leu Leu Thr Ser
    290                 295                 300

Glu Pro Ile Thr Ser Lys Glu Glu Ala Leu Lys Ile Val Ser Tyr Tyr
305                 310                 315                 320

Glu Leu Arg Trp Leu Ile Glu Asp Phe His Lys Val Trp Lys Ser Glu
                325                 330                 335

Gly Thr Gln Val Glu Gln Leu Arg
            340

<210> SEQ ID NO 25
<211> LENGTH: 344
<212> TYPE: PRT
<213> ORGANISM: Artificial Sequence
<220> FEATURE:
<223> OTHER INFORMATION: Synthetic Polypeptide

<400> SEQUENCE: 25

Met Thr His Ser Asp Ala Lys Leu Trp Ala Gln Glu Gln Phe Gly Gln
1               5                   10                  15

Ala Gln Leu Lys Asp Pro Arg Arg Thr Gln Arg Leu Ile Ser Leu Ala
            20                  25                  30

Thr Ser Ile Ala Asn Gln Pro Gly Val Ser Val Ala Lys Leu Pro Phe
        35                  40                  45

Ser Pro Ala Asp Met Glu Gly Ala Tyr Arg Phe Ile Arg Asn Glu Asn
    50                  55                  60

Ile Asn Ala Glu Asp Ile Ala Glu Ala Gly Phe Gln Ser Thr Val Ser
65                  70                  75                  80

Arg Ala Asn Glu His Lys Glu Leu Leu Ala Leu Glu Asp Thr Thr Thr
                85                  90                  95

Leu Ser Phe Pro His Arg Ser Ile Lys Glu Glu Leu Gly His Thr Asn
            100                 105                 110

Gln Gly Asp Arg Thr Arg Ala Leu His Val His Ser Thr Leu Leu Phe
        115                 120                 125

Ala Pro Gln Ser Gln Thr Ile Val Gly Leu Ile Glu Gln Gln Arg Trp
    130                 135                 140

Ser Arg Asp Ile Thr Lys Arg Gly Gln Lys His Gln His Ala Thr Arg
145                 150                 155                 160
```

```
Pro Tyr Lys Glu Lys Glu Ser Tyr Lys Trp Glu Gln Ala Ser Arg Arg
                165                 170                 175

Val Val Glu Arg Leu Gly Asp Lys Met Leu Asp Val Ile Ser Val Cys
            180                 185                 190

Asp Arg Glu Ala Asp Leu Phe Glu Tyr Leu Thr Tyr Lys Arg Gln His
        195                 200                 205

Gln Gln Arg Phe Val Val Arg Ser Met Gln Ser Arg Cys Leu Glu Glu
    210                 215                 220

His Ala Gln Lys Leu Tyr Asp Tyr Ala Gln Ala Leu Pro Ser Val Glu
225                 230                 235                 240

Thr Lys Ala Leu Thr Ile Pro Gln Lys Gly Gly Arg Lys Ala Arg Asn
                245                 250                 255

Val Lys Leu Asp Val Lys Tyr Gly Gln Val Thr Leu Lys Ala Pro Ala
            260                 265                 270

Asn Lys Lys Glu His Ala Gly Ile Pro Val Tyr Tyr Val Gly Cys Leu
        275                 280                 285

Glu Gln Gly Thr Ser Lys Asp Lys Leu Ala Trp His Leu Leu Thr Ser
    290                 295                 300

Glu Pro Ile Asn Asn Val Asp Asp Ala Met Arg Ile Ile Gly Tyr Tyr
305                 310                 315                 320

Glu Arg Arg Trp Leu Ile Glu Asp Phe His Lys Val Trp Lys Ser Glu
                325                 330                 335

Gly Thr Asp Val Glu Ser Leu Arg
                340

<210> SEQ ID NO 26
<211> LENGTH: 134
<212> TYPE: PRT
<213> ORGANISM: Artificial Sequence
<220> FEATURE:
<223> OTHER INFORMATION: Synthetic Polypeptide

<400> SEQUENCE: 26

Met Glu Glu Pro Asp Asn Leu Glu Arg Met Val Ser Ile Leu Ser Phe
1               5                   10                  15

Val Ala Val Arg Leu Leu Gln Leu Arg Glu Ser Phe Thr Leu Pro Gln
            20                  25                  30

Ala Leu Arg Ala Gln Gly Leu Leu Lys Glu Ala Glu His Val Glu Ser
        35                  40                  45

Gln Ser Ala Glu Thr Val Leu Thr Pro Asp Glu Cys Gln Leu Leu Gly
    50                  55                  60

Tyr Leu Asp Lys Gly Lys Arg Lys Arg Lys Glu Lys Ala Gly Ser Leu
65                  70                  75                  80

Gln Trp Ala Tyr Met Ala Ile Ala Arg Leu Gly Gly Phe Met Asp Ser
                85                  90                  95

Lys Arg Thr Gly Ile Ala Ser Trp Gly Ala Leu Trp Glu Gly Trp Glu
            100                 105                 110

Ala Leu Gln Ser Lys Leu Asp Gly Phe Leu Ala Ala Lys Asp Leu Met
        115                 120                 125

Ala Gln Gly Ile Lys Ile
    130

<210> SEQ ID NO 27
<211> LENGTH: 134
<212> TYPE: PRT
<213> ORGANISM: Artificial Sequence
```

<220> FEATURE:
<223> OTHER INFORMATION: Synthetic Polypeptide

<400> SEQUENCE: 27

Met Glu Glu Pro Asp Asn Leu Glu Arg Met Val Ser Ile Leu Ser Phe
1               5                   10                  15

Val Ala Val Arg Leu Leu Gln Leu Arg Glu Ser Phe Thr Pro Pro Gln
            20                  25                  30

Ala Leu Arg Ala Gln Gly Leu Leu Lys Glu Ala Glu His Val Glu Ser
        35                  40                  45

Gln Ser Ala Glu Thr Val Leu Thr Pro Asp Glu Cys Gln Leu Leu Gly
    50                  55                  60

Tyr Leu Asp Lys Gly Lys Arg Lys Glu Lys Ala Gly Ser Leu
65                  70                  75                  80

Gln Trp Ala Tyr Met Ala Ile Ala Arg Leu Gly Gly Phe Met Asp Ser
                85                  90                  95

Lys Arg Thr Gly Ile Ala Ser Trp Gly Ala Leu Trp Glu Gly Trp Glu
            100                 105                 110

Ala Leu Gln Ser Lys Leu Asp Gly Phe Leu Ala Ala Lys Asp Leu Met
        115                 120                 125

Ala Gln Gly Ile Lys Ile
    130

<210> SEQ ID NO 28
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 28

Leu Gln Ser Lys Asp Asn Ile Glu Arg Leu Val Thr Ile Ser Ala Phe
1               5                   10                  15

Ile Ala Val Arg Ile Val Gln Leu Lys Phe Ala Arg Glu Gln Pro Asp
            20                  25                  30

Glu Ile Ser Cys Glu Gln Val Leu Ser Pro Lys Ala Trp Lys Leu Leu
        35                  40                  45

Trp Ile Lys Arg Val Ser Arg Thr Leu Pro Asp Thr Val Pro Ser Met
    50                  55                  60

Lys Trp Ala Tyr Thr Glu Leu Ala Lys Leu Gly Trp Lys Asp Thr
65                  70                  75                  80

Lys Gln Thr Gly Lys Ala Ser Val Lys Val Leu Trp Gln Gly Trp Phe
                85                  90                  95

Lys Leu Gln Thr Ile Leu Glu Gly Tyr Asp Leu Ala Lys Ser Leu Glu
            100                 105                 110

Ala Asp Leu
        115

<210> SEQ ID NO 29
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 29

Val Gln Ser Lys Asp Asn Leu Asp Arg Leu Ala Thr Ile Tyr Ala Phe
1               5                   10                  15

Leu Ala Val Arg Ile Phe Gln Leu Lys Phe Ala Asn Glu Gln Ile Glu
            20                  25                  30

Asp Ile Ser Ser Glu Lys Ile Leu Ser Pro Arg Ala Trp Lys Leu Leu
        35                  40                  45

Trp Leu Lys Arg Ile Lys Thr Pro Pro Glu Glu Val Pro Thr Ala
 50                  55                  60

Lys Trp Ala Tyr Glu His Leu Ala Arg Leu Gly Gly Trp Lys Asp Ser
 65                  70                  75                  80

Lys Arg Asn Gly Arg Ala Ser Val Lys Thr Leu Trp Glu Gly Trp Leu
                85                  90                  95

Lys Leu Gln Ala Ile Leu Glu Gly Tyr Glu Leu Ala Leu Ser Leu Glu
            100                 105                 110

Gln Asp Leu
        115

<210> SEQ ID NO 30
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 30

Met Gln Ser Lys Asp Asn Leu Glu Arg Leu Ser Val Ile Leu Ala Phe
 1               5                  10                  15

Ile Ala Thr Arg Leu Leu Gln Leu Arg Phe Met Asn Glu Ser Asp Glu
            20                  25                  30

Leu Ser Lys Ser Ser Cys Glu Pro Ile Leu Lys Gly Lys Ala Trp Lys
        35                  40                  45

Leu Met Trp Leu Lys Leu Glu Arg Lys Gly Leu Pro Lys Glu Ala Pro
 50                  55                  60

Asp Ile Ser Trp Ala Tyr Lys Gly Ile Ala Arg Leu Gly Gly Trp Lys
 65                  70                  75                  80

Asn Thr Lys Arg Thr Gly Arg Ala Ser Ile Lys Thr Leu Trp Gln Gly
                85                  90                  95

Trp Phe Arg Leu Gln Thr Ile Leu Glu Gly Tyr Glu Leu Ala Lys Ser
            100                 105                 110

Leu Asp Ser Pro Asp
        115

<210> SEQ ID NO 31
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 31

Leu Gln Ser Lys Asp Asn Leu Glu Arg Leu Ser Val Ile Tyr Ala Phe
 1               5                  10                  15

Val Ala Thr Arg Leu Leu Ala Leu Arg Phe Met Lys Glu Val Asp Glu
            20                  25                  30

Leu Thr Lys Glu Ser Cys Glu Lys Val Leu Gly Gln Lys Ala Trp Lys
        35                  40                  45

Leu Leu Trp Leu Lys Leu Glu Ser Lys Thr Leu Pro Lys Glu Val Pro
 50                  55                  60

Asp Met Gly Trp Ala Tyr Lys Asn Leu Ala Lys Leu Gly Gly Trp Lys
 65                  70                  75                  80

Asp Thr Lys Arg Thr Gly Arg Ala Ser Ile Lys Val Leu Trp Glu Gly
            85                  90                  95

Trp Phe Lys Leu Gln Thr Ile Leu Glu Gly Tyr Glu Leu Ala Met Ser
        100                 105                 110

Leu Asp His
        115

<210> SEQ ID NO 32
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 32

Met Asn Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
            20                  25                  30

Ala Asn Asp Pro Gly Lys Pro Phe Val Ser Ile Thr Gln Ser Lys Ala
        35                  40                  45

Asp Met Glu Gly Ala Tyr Arg Phe Ile Arg Asn Glu His Val Asn Ala
    50                  55                  60

Asp Ala Ile Ala Lys Ala Gly Tyr Leu Val Thr Ala Ala Gln Ala Ala
65                  70                  75                  80

Lys His Asn Leu Leu Leu Ala Leu Glu Asp Thr Thr Ala Ile Thr Tyr
                85                  90                  95

Ser His Arg Ser Val Arg Asp Glu Leu Gly His Val Asn Gln Gly Asn
            100                 105                 110

Asn Tyr Arg Gly Ile Leu Ala His Ser Val Leu Leu Phe Ala Pro Glu
        115                 120                 125

Gln Gln Glu Leu Val Gly Leu Ile Glu Gln Ser Arg Trp Thr Arg Asp
    130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
                165                 170                 175

Arg Leu Gly Thr Lys Met Ala Asp Val Ile Ser Val Cys Asp Arg Glu
            180                 185                 190

Ala Asp Ile Tyr Glu Tyr Leu Gln Tyr Lys Leu Ser Lys Gln His Arg
        195                 200                 205

Phe Val Val Arg Ser Met Gln Ser Arg His Ile Glu Gln Ser Glu Gln
    210                 215                 220

Lys Leu Tyr Asp Tyr Ala Ala Gly Leu Glu Ser Ala Gly Gln Lys Gln
225                 230                 235                 240

Ile His Ile Ala Gln Lys Gly Gly Arg Lys Ala Arg Thr Ala Thr Val
                245                 250                 255

Asp Ile Val Phe Ala Pro Val Thr Leu Gln Val Pro Ala Asn Lys Arg
            260                 265                 270

Gly Glu Ser Leu Ser Leu Tyr Tyr Val Gly Cys Glu Glu Arg Ala Asp
        275                 280                 285

Asp Lys Asn Ala Leu Asn Trp His Leu Leu Thr Thr Glu Pro Val Gln
    290                 295                 300

Ser Lys Ala Asp Ala Leu Asn Ile Ile Arg Tyr Tyr Glu His Arg Trp
305                 310                 315                 320

```
Leu Val Glu Glu Tyr His Lys Ala Trp Lys Thr Asp Gly Thr Asp Ile
            325                 330                 335

Glu Asn Ala Arg Leu Gln Ser Lys Asp Asn Ile Glu Arg Leu Val Thr
            340                 345                 350

Ile Ser Ala Phe Ile Ala Val Arg Ile Val Gln Leu Lys Phe Ala Arg
            355                 360                 365

Glu Gln Pro Asp Glu Ile Ser Cys Glu Gln Val Leu Ser Pro Lys Ala
            370                 375                 380

Trp Lys Leu Leu Trp Ile Lys Arg Val Ser Arg Thr Leu Pro Asp Thr
385                 390                 395                 400

Val Pro Ser Met Lys Trp Ala Tyr Thr Glu Leu Ala Lys Leu Gly Gly
            405                 410                 415

Trp Lys Asp Thr Lys Gln Thr Gly Lys Ala Ser Val Lys Val Leu Trp
            420                 425                 430

Gln Gly Trp Phe Lys Leu Gln Thr Ile Leu Glu Gly Tyr Asp Leu Ala
            435                 440                 445

Lys Ser Leu Glu Ala Asp Leu
            450                 455

<210> SEQ ID NO 33
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 33

Met Asn Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
            20                  25                  30

Ala Asn Asp Pro Gly Lys Pro Phe Val Ser Ile Thr Gln Ser Pro Ala
            35                  40                  45

Asp Ala Glu Gly Ala Tyr Arg Phe Ile Arg Asn Glu His Val Asn Ala
        50                  55                  60

Asp Ala Ile Ala Lys Ala Gly Tyr Leu Val Thr Ala Ala Gln Ala Ala
65              70                  75                  80

Lys His Asn Leu Leu Ala Leu Glu Asp Thr Thr Ala Ile Thr Tyr
            85                  90                  95

Ser His Arg Ser Val Arg Asp Glu Leu Gly His Val Asn Gln Gly Asn
            100                 105                 110

Asn Tyr Arg Gly Ile Leu Ala His Ser Val Leu Leu Phe Ala Pro Glu
            115                 120                 125

Gln Gln Glu Leu Val Gly Leu Ile Glu Gln Ser Arg Trp Thr Arg Asp
            130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
            165                 170                 175

Arg Leu Gly Thr Lys Met Ala Asp Val Ile Ser Val Cys Asp Arg Glu
            180                 185                 190

Ala Asp Ile Tyr Glu Tyr Leu Gln Tyr Lys Leu Ser Lys Gln His Arg
            195                 200                 205

Phe Val Val Arg Ser Met Gln Ser Arg His Ile Glu Gln Ser Glu Gln
            210                 215                 220
```

Lys Leu Tyr Asp Tyr Ala Ala Gly Leu Glu Ser Ala Gly Gln Lys Gln
225                 230                 235                 240

Ile His Ile Ala Gln Lys Gly Gly Arg Lys Ala Arg Thr Ala Thr Val
            245                 250                 255

Asp Ile Val Phe Ala Pro Val Thr Leu Gln Val Pro Ala Asn Lys Arg
        260                 265                 270

Gly Glu Ser Leu Ser Leu Tyr Tyr Val Gly Cys Glu Glu Arg Ala Asp
    275                 280                 285

Asp Lys Asn Ala Leu Asn Trp His Leu Leu Thr Thr Glu Pro Val Gln
    290                 295                 300

Ser Lys Ala Asp Ala Leu Asn Ile Ile Arg Tyr Tyr Glu His Arg Trp
305                 310                 315                 320

Leu Val Glu Glu Tyr His Lys Ala Trp Lys Thr Asp Gly Thr Asp Ile
                325                 330                 335

Glu Asn Ala Arg Leu Gln Ser Lys Asp Asn Ile Glu Arg Leu Val Thr
            340                 345                 350

Ile Ser Ala Phe Ile Ala Val Arg Ile Val Gln Leu Lys Phe Ala Arg
        355                 360                 365

Glu Gln Pro Asp Glu Ile Ser Cys Glu Gln Val Leu Ser Pro Lys Ala
    370                 375                 380

Trp Lys Leu Leu Trp Ile Lys Arg Val Ser Arg Thr Leu Pro Asp Thr
385                 390                 395                 400

Val Pro Ser Met Lys Trp Ala Tyr Thr Glu Leu Ala Lys Leu Gly Gly
                405                 410                 415

Trp Lys Asp Thr Lys Gln Thr Gly Lys Ala Ser Val Lys Val Leu Trp
            420                 425                 430

Gln Gly Trp Phe Lys Leu Gln Thr Ile Leu Glu Gly Tyr Asp Leu Ala
        435                 440                 445

Lys Ser Leu Glu Ala Asp Leu
    450                 455

<210> SEQ ID NO 34
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 34

Met Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
            20                  25                  30

Ala Asn Asp Pro Gly Lys Pro Phe Val Ser Ile Thr Gln Ser Lys Ala
        35                  40                  45

Asp Ala Glu Gly Ala Tyr Arg Phe Ile Arg Asn Glu His Val Asn Ala
    50                  55                  60

Asp Ala Ile Ala Lys Ala Gly Tyr Leu Val Thr Ala Ala Gln Ala Ala
65                  70                  75                  80

Lys His Asn Leu Leu Ala Leu Glu Asp Thr Thr Ala Ile Thr Tyr
                85                  90                  95

Ser His Arg Ser Val Arg Asp Glu Leu Gly His Val Asn Gln Gly Asn
            100                 105                 110

Asn Tyr Arg Gly Ile Leu Ala His Ser Val Leu Leu Phe Ala Pro Glu
        115                 120                 125

Gln Gln Glu Leu Val Gly Leu Ile Glu Gln Ser Arg Trp Thr Arg Asp
            130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
                165                 170                 175

Arg Leu Gly Thr Lys Met Ala Asp Val Ile Ser Val Cys Asp Arg Glu
            180                 185                 190

Ala Asp Ile Tyr Glu Tyr Leu Gln Tyr Lys Leu Ser Lys Gln His Arg
        195                 200                 205

Phe Val Val Arg Ser Met Gln Ser Arg His Ile Glu Gln Ser Glu Gln
    210                 215                 220

Lys Leu Tyr Asp Tyr Ala Ala Gly Leu Glu Ser Ala Gly Gln Lys Gln
225                 230                 235                 240

Ile His Ile Ala Gln Lys Gly Arg Lys Ala Arg Thr Ala Thr Val
                245                 250                 255

Asp Ile Val Phe Ala Pro Val Thr Leu Gln Val Pro Ala Asn Lys Arg
                260                 265                 270

Gly Glu Ser Leu Ser Leu Tyr Tyr Val Gly Cys Glu Glu Arg Ala Asp
            275                 280                 285

Asp Lys Asn Ala Leu Asn Trp His Leu Leu Thr Thr Glu Pro Val Gln
        290                 295                 300

Ser Lys Ala Asp Ala Leu Asn Ile Ile Arg Tyr Tyr Glu His Arg Trp
305                 310                 315                 320

Leu Val Glu Glu Tyr His Lys Ala Trp Lys Thr Asp Gly Thr Asp Ile
                325                 330                 335

Glu Asn Ala Arg Leu Gln Ser Lys Asp Asn Ile Glu Arg Leu Val Thr
            340                 345                 350

Ile Ser Ala Phe Ile Ala Val Arg Ile Val Gln Leu Lys Phe Ala Arg
        355                 360                 365

Glu Gln Pro Asp Glu Ile Ser Cys Glu Gln Val Leu Ser Pro Lys Ala
    370                 375                 380

Trp Lys Leu Leu Trp Ile Lys Arg Val Ser Arg Thr Leu Pro Asp Thr
385                 390                 395                 400

Val Pro Ser Met Lys Trp Ala Tyr Thr Glu Leu Ala Lys Leu Gly Gly
                405                 410                 415

Trp Lys Asp Thr Lys Gln Thr Gly Lys Ala Ser Val Lys Val Leu Trp
            420                 425                 430

Gln Gly Trp Phe Lys Leu Gln Thr Ile Leu Glu Gly Tyr Asp Leu Ala
        435                 440                 445

Lys Ser Leu Glu Ala Asp Leu
450                 455

<210> SEQ ID NO 35
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 35
tcgtcggcag cgtcagatgt gtataagaga cag                                      33

<210> SEQ ID NO 36
<211> LENGTH: 19

```
<212> TYPE: DNA
<213> ORGANISM: Artificial Sequence
<220> FEATURE:
<223> OTHER INFORMATION: Synthetic Polynucleotide

<400> SEQUENCE: 36
tctacacata ttctctgtc                                                  19

<210> SEQ ID NO 37
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 37
gtctcgtggg ctcggagatg tgtataagag acag                                 34

<210> SEQ ID NO 38
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 38
tctacacata ttctctgtc                                                  19

<210> SEQ ID NO 39
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 39
tcgtcggcag cgtcagatgt gtataagaga cag                                  33

<210> SEQ ID NO 40
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 40
tctacacata ttctctgtc                                                  19

<210> SEQ ID NO 41
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 41
gtctcgtggg ctcggagatg tgtataagag acag                                 34

<210> SEQ ID NO 42
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 42
```

-continued

```
tctacacata ttctctgtc                                          19

<210> SEQ ID NO 43
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 43
tcgtcggcag cgtcagatgt gtataagaga cag                          33

<210> SEQ ID NO 44
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 44
tctacacata ttctctgtc                                          19

<210> SEQ ID NO 45
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 45
gtctcgtggg ctcggagatg tgtataagag acag                         34

<210> SEQ ID NO 46
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 46
tctacacata ttctctgtc                                          19

<210> SEQ ID NO 47
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 47
agatgtgtat aagagacag                                          19

<210> SEQ ID NO 48
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 48
tctacacata ttctctgtc                                          19

<210> SEQ ID NO 49
<211> LENGTH: 33
<212> TYPE: DNA
<213> ORGANISM: Artificial Sequence
```

```
<220> FEATURE:
<223> OTHER INFORMATION: Synthetic Polynucleotide

<400> SEQUENCE: 49
tcgtcggcag cgtcagatgt gtataagaga cag                                    33

<210> SEQ ID NO 50
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 50
tctacacata ttctctgtc                                                    19

<210> SEQ ID NO 51
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 51
gtctcgtggg ctcggagatg tgtataagag acag                                   34

<210> SEQ ID NO 52
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 52
tctacacata ttctctgtc                                                    19

<210> SEQ ID NO 53
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (19)..(19)
<223> OTHER INFORMATION: modification is a 3'-phosphate.

<400> SEQUENCE: 53
agatgtgtat aagagacag                                                    19

<210> SEQ ID NO 54
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 54
tctacacata ttctctgtc                                                    19

<210> SEQ ID NO 55
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (19)..(19)
<223> OTHER INFORMATION: 3'-spacer referred to as /"3SpC3"/

<400> SEQUENCE: 55
agatgtgtat aagagacag                                                19

<210> SEQ ID NO 56
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 56
tctacacata ttctctgtc                                                19

<210> SEQ ID NO 57
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (50)..(51)
<223> OTHER INFORMATION: wherein the (*) represents a phosphorothioate
      bond

<400> SEQUENCE: 57
aatgatacgg cgaccaccga gatctacact agatcgctcg tcggcagcgt c             51

<210> SEQ ID NO 58
<211> LENGTH: 47
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (46)..(47)
<223> OTHER INFORMATION: wherein the (*) represents a phosphorothioate
      bond

<400> SEQUENCE: 58
caagcagaag acggcatacg agattcgcct tagtctcgtg ggctcgg                 47
```

TRANSPOSASE COMPETITOR CONTROL SYSTEM

RELATED APPLICATIONS

This application claims priority to, and the benefit of U.S. Provisional Application No. 62/324,683 filed on Apr. 19, 2016, the contents of which are incorporated herein by reference in their entirety.

FIELD OF THE DISCLOSURE

The disclosure is directed towards the field of molecular biology; and, more specifically the use of transposases as molecular tools to fragment DNA.

INCORPORATION BY REFERENCE OF SEQUENCE LISTING

The contents of the text file name "RMSI-007-001US ST25" which was created on Dec. 14, 2017 and is 80 KB in size, are hereby incorporated by reference in their entirety.

BACKGROUND

The transposase-based generation of DNA sequencing libraries faces a number of challenges that, prior to the instant disclosure, had not been solved. Technical challenges involve overcoming the fact that a single transpososome is capable of only a single insertion-cut event, and the complex is not subsequently released to insert and cut elsewhere. Consequently, existing technologies have difficulty controlling the insert size. The method is sensitive to DNA input amounts and significant insertion site bias exists. This bias is caused by the fact that while the transpososome can insert at diverse sites, it displays a variety of preferences for a variety DNA sequences, to the degree that a consensus preferred-sequence can be determined. The insertion pattern is thus semi-random, and the transpososome can be regarded a sequence-specific DNA-binding complex, albeit one with highly imperfect sequence discrimination.

SUMMARY

The disclosure provides a transpososome-based library preparation system that overcomes the long-felt but unmet need in the art for a method of DNA fragmentation that maintains a desired average fragment size while decreasing the insertion bias compared to existing methods. Moreover, the methods of the disclosure are equally effective regardless of the amount of DNA used.

The methods of the disclosure involve expressing a transposase (Tnp), and activating (also referred to as "loading") it with transposase-binding end sequence (ES) DNA (also referred to as "arms") to create a transpososome. The ES sequence is typically, but not necessarily, a "mosaic" sequence, in that it is not a natural ES, but rather a combination of the two natural ES (inner and outer) that occur for each insertion sequence (IS). The arms can carry sequencer-specific sequences, or adapters. Contacting the transpososome and target DNA results in "tagmentation", a term meant to describe a simultaneous DNA fragmentation and sequencing adapter insertion. Methods of the disclosure include contacting a mixture of "active" and "inactive" transpososomes to a target DNA. Inactive transpososomes are capable of binding to DNA but are incapable of cutting either DNA strand.

Specifically, the disclosure provides a method of fragmenting DNA comprising contacting a sample of target DNA with (a) a composition comprising an active transpososome, and (b) a composition comprising an inactive transpososome, under conditions suitable for transpososome activity, wherein a ratio of an amount of the inactive transpososome in the composition of (b) to an amount of the active transpososome in the composition of (a) determines a mean fragment size and a level of insertion bias.

In certain embodiments of the methods of the disclosure, the combination of the active transpososome in the composition of (a) and the inactive transpososome in the composition of (b) occupies greater than 50%, 55%, 60%, 65%, 70%, 75%, 80%, 85%, 90%, 95% or 99% of the transpososome binding sites of the input DNA. In certain embodiments of the methods of the disclosure, the combination of the active transpososome in the composition of (a) and the inactive transpososome in the composition of (b) occupies 100% of the transpososome binding sites of the input DNA.

In certain embodiments of the methods of the disclosure, the inactive transpososome and the active transpososome preferentially bind to a consensus sequence within the target DNA. In certain embodiments, the inactive transpososome and the active transpososome bind to the consensus sequence with perfect complementarity. In certain embodiments, the inactive transpososome and the active transpososome bind to the consensus sequence with imperfect complementarity. Exemplary consensus sequences within a target DNA of the disclosure may comprise an A/T rich and/or a C/G rich sequence. In certain embodiments, consensus sequences within a target DNA of the disclosure may comprise an A/T rich sequence flanked on each end by a G/C pair. Exemplary consensus sequences within a target DNA of the disclosure may comprise a sequence of at least 2, 3, 4, 5, 6, 7, 8, 9 or 10 consecutive identical nucleotides. Exemplary consensus sequences within a target DNA of the disclosure may comprise a sequence at least 2, 3, 4, 5, 6, 7, 8, 9 or 10 non-consecutive identical nucleotides.

In certain embodiments of the methods of the disclosure, inactive transpososomes and/or active transpososomes may bind to a non-preferred, a semi-random or a random sequence within the target DNA, when, for example, all or most of the preferred binding sites are occupied. When inactive transpososomes and/or active transpososomes of the disclosure bind to a non-preferred, a semi-random or a random sequence within the target DNA, the non-preferred, the semi-random or the random sequence within the target DNA may not share any sequence similarity or identity.

In certain embodiments of the methods of the disclosure, an amount of the input or target DNA is unknown. The amount of the target DNA may be irrelevant as the methods will be efficacious even if the combination of the active transpososome in the composition of (a) and the inactive transpososome in the composition of (b) occupies less than 100% of the transpososome binding sites of the input or target DNA.

In certain embodiments of the methods of the disclosure, the inactive transpososome is a modified form of the active transpososome. The modification may inhibit the ability of the inactive transpososome to cut the target DNA and preserve the ability of the inactive transpososome to bind the target DNA. In certain embodiments of the methods of the disclosure, the inactive transpososome may comprise a mutation in an amino acid sequence encoding a transposase of the inactive transpososome. Exemplary mutations may occur at a position within a catalytic domain of the transposase of the inactive transpososome. For example, the inactive transposase may be a wild type or hyperactive Tn5-derived transposase and the mutation may occur at a position within a catalytic triad selected from the group consisting of D97, D188, and E326 (see Davies et al. (2000) Science 289:77-85). Alternatively, the inactive transposase may be related to a wild type or a hyperactive Tn5-derived transposase (e.g. a sequence or splice variant of Tn5-transposase or a transposase having conserved sequences but originating from another species or type of transposon or insertion element, or a transposase derived from any member of the IS4 family of insertion sequences) and the mutation may occur at a position within a catalytic triad that is a functional equivalent to the triad selected from the group consisting of D97, D188, and E326. In certain embodiments, the hyperactive Tn5 transposase may be encoded by an amino acid sequence comprising (catalytic triad bold and underlined):

```
                                                           (SEQ ID NO: 1)
  1  mitsalhraa dwaksvfssa algdprrtar lvnvaaqlak ysgksitiss egskaagega 61  yrfirnpnvs aeairkagam qtvklagefp ellaiedtts lsyrhqvaee lgklgsiqdk 121  srgwwvhsvl lleattfrtv gllhgewwmr pddpadadek esgkwlaaaa tsrlrmgsmm 181  snviavcdre adihaylqdk lahnerfvvr skhprkdves glylydhlkn qpelggyqis 241  ipqkgvvdkr gkrknrpark aslslrsgri tlkqgnitln avlaeeinpp kgetplkwll 301  ltsepvesla qalrvidiyt hrwrieefhk awktgagaer qrmeepdnle rmvsilsfva 361  vrllqlresf tppqalraqg llkeaehves qsaetvltpd ecqllgyldk gkrkrkekag 421  slqwaymaia rlggfmdskr tgiaswgalw egwealqskl dgflaakdlm aqgiki.
```

In certain embodiments of the methods of the disclosure, the inactive transpososome is a modified form of the active transpososome. The modification may inhibit the ability of the inactive transpososome to cut the target DNA and preserve the ability of the inactive transpososome to bind the target DNA. In certain embodiments of the methods of the disclosure, the inactive transposase may comprise a mutation in an amino acid sequence encoding a transposase of the inactive transpososome. Exemplary mutations may occur at a position within a catalytic domain of the transposase of the inactive transpososome. For example, the inactive transposase may be a different enzyme to Tn5-Tnp, such as the transposase derived from *Alishewanella aestuarii* (TnAa-Tnp) and the mutation may occur at a position within a catalytic triad selected from the group consisting of D90, D190, and E323. In certain embodiments, the TnAa transposase may be encoded by an amino acid sequence comprising (catalytic triad bold and underlined):

```
                                                           (SEQ ID NO: 2)
  1  mnnaqwakst fgqadlgdpr rttrlvklae tlandpgkpf vsitqspadm egayrfirne 61  hvnadaiaka gylvtaaqaa khnlllaled ttaityshrs vrdelghvnq gnnyrgilah 121  svllfapeqq elvglieqsr wtrdistrgk khvrtqtpye ekesfkwqsa svnlsarlgt 181  kmadvisvcd readiyeylq yklskqhrfv vrsmqsrhie qseqklydya aglesagqkq 241  ihiaqkggrk artatvdivf apvtlqvpan krgeslslyy vgceeraddk nalnwhlltt 301  epvqskadal niiryyehrw lveeyhkawk tdgtdienar lqskdnierl vtisafiavr 361  ivqlkfareq pdeisceqvl spkawkllwi krvsrtlpdt vpsmkwayte laklggwkdt 421  kqtgkasvkv lwqgwfklqt ilegydlaks leadl.
```

An alignment of a hyperactive Tn5-derived and the TnAa-derived transposase reveals that the residues of the catalytic triad are highly conserved between transposases. A similar alignment may be used to identify a functionally equivalent catalytic triad in other transposases.

The alignment of TnAa-derived and Hyperactive Tn5-derived transposases (catalytic triad bold and underlined) is as follows:

The symbol below the aligned amino acid residues indicates the degree of conservation at that position. An asterisk, "*" indicates positions which have a single, fully conserved residue. A ":" (colon) indicates conservation between groups of strongly similar properties—scoring >0.5 in the Gonnet PAM 250 matrix. A "." (period) indicates conservation between groups of weakly similar properties—scoring=<0.5 in the Gonnet PAM 250 matrix. A dash "-" indicates spacing in alignment.

For alignment below of TnAa (SEQ ID NO: 3) and HyperTn (SEQ ID NO: 4).

```
TnAa     M------NNAQWAKSTFGQADLGDPRRTTRLVKLAETLANDPGKPF-VSITQSPADMEGA
HyperTn  MITSALHRAADWAKSVFSSAALGDPRRTAPLVNVAAQLAKYSGKSITISSEGSKAAQEGA
               *:****.*..* *******:***.::.**; .**.: :*  * *  ***

TnAa     YRFIRNEHVNADAIAKAGYLVTAAQAAKHNLLLALEDTTAITYSHRSVRDELGHVNQ-GN
HyperTn  YRFIRNPNVSAEAIRKAGAMQTVKLAQEFPELLAIEDTTSLSYRHQ-VAEELGKLGSIQD
         ****** :*.*:** *** : *. *  :. ***.****:::* *: * :***:::.. :

TnAa     NYRGILAHSVLLFAPEQQELVGLIEQSRWTRDISTRGKKHVRTQTP--YEEKESFKWQSA
HyperTn  KSRGWWVHSVLLLEATTFRTVGLLHQEWW----------MRPDDPADADEKESGKWLAA
         : ** .*****:.  . ***:.*. *              :*.: *  :**** ** :*

TnAa     SVNLSARLGTKMADVISVCDREADIYEYLQYKLSKQHRFVVRSMQSRHIEQSEQKLYDYA
HyperTn  AATSRLRMGSMMSNVIAVCDREADIHAYLQDKLAHNERFVVRSKHPRKDVESGLYLYDHL
         :**    *:*: *:;**:********: *** **::: :****** :.*:   :*   ***:

TnAa     AGLESAGQKQIHIAQKG---------GRKARTATVDIVFAPVTLQVPANKRGESLSLYYV
HyperTn  KNQPELGGYQISIPQKGVVDKRGKRKNRPARKASLSLRSGRITL-----KQG-NITLNAV
          .  .  * ** *.***        .* **.*::.: . .**      *:.   ::* *

TnAa     GCEERADDK--NALNWHLLTTEPVQSKADALNIIRYYEHRWLVEEYHKAWKTDGTDIENA
HyperTn  LAEEINPPKGETPLKWLLLTSEPVESLAQALRVIDIYTHRWRIEEFHKAWKT-GAGAERQ
          .**     *  ..*:* ***.****:*  *:* :*  * *** .**:****** *:. *.

TnAa     RLQSKDNIERLVTISAFIAVRIVQLKFAREQPDEI---------------SCEQVLSPKA
HyperTn  RMEEPDNLERMVSILSFVAVRLLQLRESFTPPQALRAQGLLKEAEHVESQSAETVLTPDE
         *::.. **:**:*:*  :*:***::**:.;**: :    *: :              *.* **:*.

TnAa     WKLL-WIKRVSRTLPDTVPSMKWAYTELAKLGGWKDTKQTGKASVKVLWQGWFKLQTILE
HyperTn  CQLLGYLDKGKRKRKEKAGSLQWAYMAIARLGGFMDSKRTGIASWGALWEGWEALQSKLD
          :** ::..: .*.    :.. .*:*** . :*:***: *:*:** **  .**:** **: *:

TnAa     GYDLAKSLEAD---L
HyperTn  GFLAAKDLMAQGIKI
         *:  **.* *:   :
```

Inactive transpososomes of the disclosure may be a modified form of the active transpososomes of the disclosure. The modification may inhibit the ability of an inactive transpososome to cut a target DNA and preserve the ability of the inactive transpososome to bind the target DNA.

Inactive transpososomes of the disclosure may comprise a modified DNA arm. In certain embodiments, the modified DNA arm may be a mosaic DNA arm. Exemplary modified DNA arms of the disclosure, include, but are not limited to, one or more of: a 3'-phosphate instead of a 3'-OH on the terminal nucleotide of a transferred strand of the arm, a dideoxy nucleotide at a terminal nucleotide of a transferred strand of the arm, a bulky group that sterically inhibits strand transfer, or any combination thereof.

In certain embodiments of the methods of the disclosure, modified arms of a transpososome include groups that are chemically different from a 3'-hydroxyl at the 3'-terminus of the transferred strand such that these chemical groups prevent strand transfer. Standard synthetic DNA oligonucleotides contain a 3'-OH group at the 3'-terminus. A preferred group which promotes strand transfer is 3'-OH as shown below:

```
ME_MR:   5'-AGATGTGTATAAGAGACAG-OH-3' (SEQ ID NO: 5)
            |||||||||||||||||||
ME_RC:   3'-TCTACACATATTCTCTGTC    -5' (SEQ ID NO: 6)
```

In certain embodiments of the methods of the disclosure, inactive transpososomes may comprise a 3'-terminal nucleotide base in a transferred strand with a different chemical moiety (i.e., different from the standard synthetic DNA oligonucleotides containing a 3'-OH group at the 3'-terminus) as marked with an "X" below:

```
ME_MR:   5'-AGATGTGTATAAGAGACAG-X-3'  (SEQ ID NO: 7)
            |||||||||||||||||||
ME_RC:   3'-TCTACACATATTCTCTGTC    -5' (SEQ ID NO: 8)
```

The "X" moiety attached to the 3'-carbon of the 3'-terminal base of the transferred strand, as shown below, may be any chemical moiety capable of preventing or inhibiting strand transfer, thereby producing an inactive transpososome of the disclosure.

"X" moieties of the disclosure are incompatible with one or more mechanism(s) of strand transfer enabling the inactive transpososome to recognize and load the arm DNA while preventing the inactive transpososome from nicking and/or transferring the modified DNA to the target DNA (e.g. genomic DNA).

Exemplary "X" moieties include, but are not limited to:

A. 3'-H. (see the ME_MR oligo.

```
ME_MR:   5'-AGATGTGTATAAGAGACAG-H-3'   (SEQ ID NO: 9)
            |||||||||||||||||||
ME_RC:   3'-TCTACACATATTCTCTGTC    -5' (SEQ ID NO: 10)
```

The image below depicts the 3'-terminal base (guanine) in the ME_MR oligo shown above. The ME_MR oligo comprises a 3' terminal base with a 3'-hydrogen rather than the conventional 3'-OH moiety.

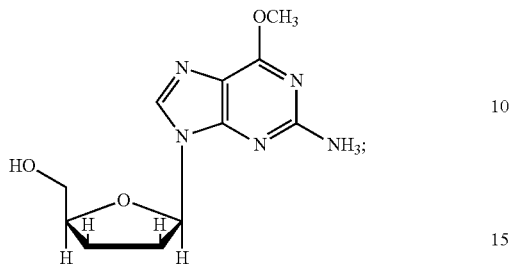

B. 3'-phosphate:

```
ME_MR:   5'-AGATGTGTATAAGAGACAG-Phoshate-3'   (SEQ ID NO: 11)
            ||||||||||||||||||| 
ME_RC:   3'-TCTACACATATTCTCTGTC        -5'    (SEQ ID NO: 12)
```

The image below depicts the 3'-terminal base (guanine) in the ME_MR oligo shown above. The ME_MR oligo comprises a 3' terminal base with a 3'-phosphate rather than the conventional 3'-OH moiety.

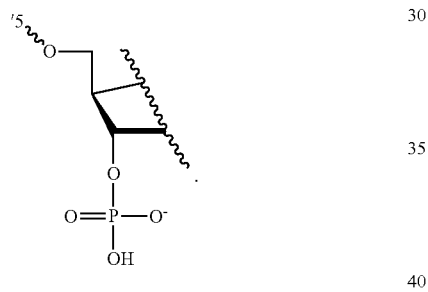

Similarly, "X" moieties of the disclosure may include one or more bulky groups that sterically inhibit strand transfer (the structures shown below are attached to the 3'-carbon of the 3'-terminal base of the transferred strand) and include, but are not limited to:

C. a hexanediol

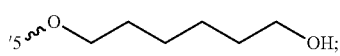

D. a 3-carbon spacer

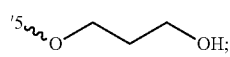

E. a triethylene glycol,

F. a hexa-ethyleneglycol, or any combination thereof.

Inactive transpososomes of the disclosure may comprise a modified base, a synthetic base or a nucleotide analog in place of a 3'-terminal nucleotide base in a transferred strand (marked as "Z" below). Exemplary modified bases, synthetic bases or nucleotide analogs enable the transposase to recognize and load arm DNA but prevent the inactive transpososome from nicking and/or transferring a modified DNA to a target DNA (e.g. genomic DNA).

```
ME_MR:   5'-AGATGTGTATAAGAGACAZ-3'   (SEQ ID NO: 13; "Z" referred to as "N" Sequence listing)
            |||||||||||||||||||
ME_RC:   3'-TCTACACATATTCTCTGTC-5'   (SEQ ID NO: 14)
```

Exemplary "Z" modified bases, synthetic bases or nucleotide analogs may comprise, but are not limited to:
A. An inverted base. The 3'-terminal base of the transferred strand (typically guanine) in the conformation shown below would prevent the transposase from inserting the transferred strand.

A.

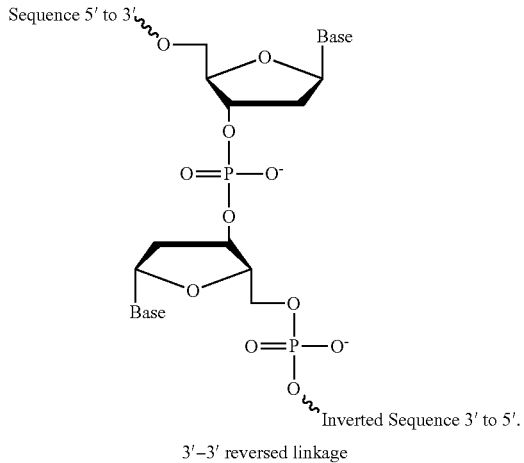

3'–3' reversed linkage

B.

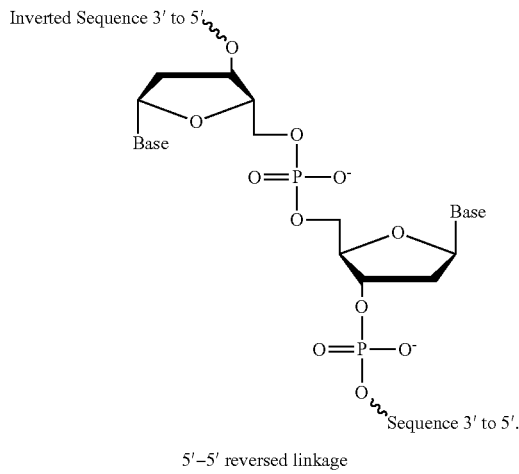

5'–5' reversed linkage

B. An abasic site.

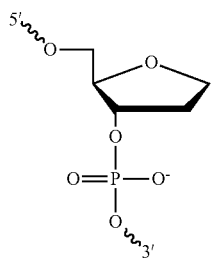

Exemplary "Z" nucleotide analogs may comprise, but are not limited to: locked nucleic acid (LNA), bridged nucleic acid (BNA) or xeno nucleic acid (XNA). Exemplary "Z" nucleotide analogs may further comprise an "X" moiety of the disclosure at the 3'-carbon of the 3'-terminal nucleotide or nucleotide analog to prevent the addition of the transferred strand to the target DNA, while permitting the transpososome to recognize and load the modified arms, resulting in the production of an inactive transpososome.

In certain embodiments of the methods of the disclosure, a change in the ratio of an amount of the inactive transpososome in the composition of (b) to an amount of the active transpososome in the composition of (a) results in a change in the average fragment size.

In certain embodiments of the methods of the disclosure, an increase in the ratio of an amount of the inactive transpososome in the composition of (b) to an amount of the active transpososome in the composition of (a) results in an increase in the average fragment size.

In certain embodiments of the methods of the disclosure, a decrease in the ratio of an amount of the inactive transpososome in the composition of (b) to an amount of the active transpososome in the composition of (a) results in a decrease in the average fragment size.

In certain embodiments of the methods of the disclosure, the level of insertion bias is decreased compared to a method that does not comprise contacting the target DNA with the inactive transpososome.

The disclosure further provides a method of fragmenting DNA comprising contacting a sample of target DNA with (a) a composition comprising an active transpososome, and (b) a composition comprising a DNA binding protein that is not a transposase or transpososome, under conditions suitable for transpososome activity, wherein a ratio of an amount of the DNA binding protein in the composition of (b) to an amount of the active transpososome in the composition of (a) determines a mean fragment size and a level of insertion bias.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12A shows start site bias was estimated as the cumulative nucleotide base variance at positions flanking the read start site.

FIG. 12B shows the base preference at each position.

DETAILED DESCRIPTION

Figure 1:
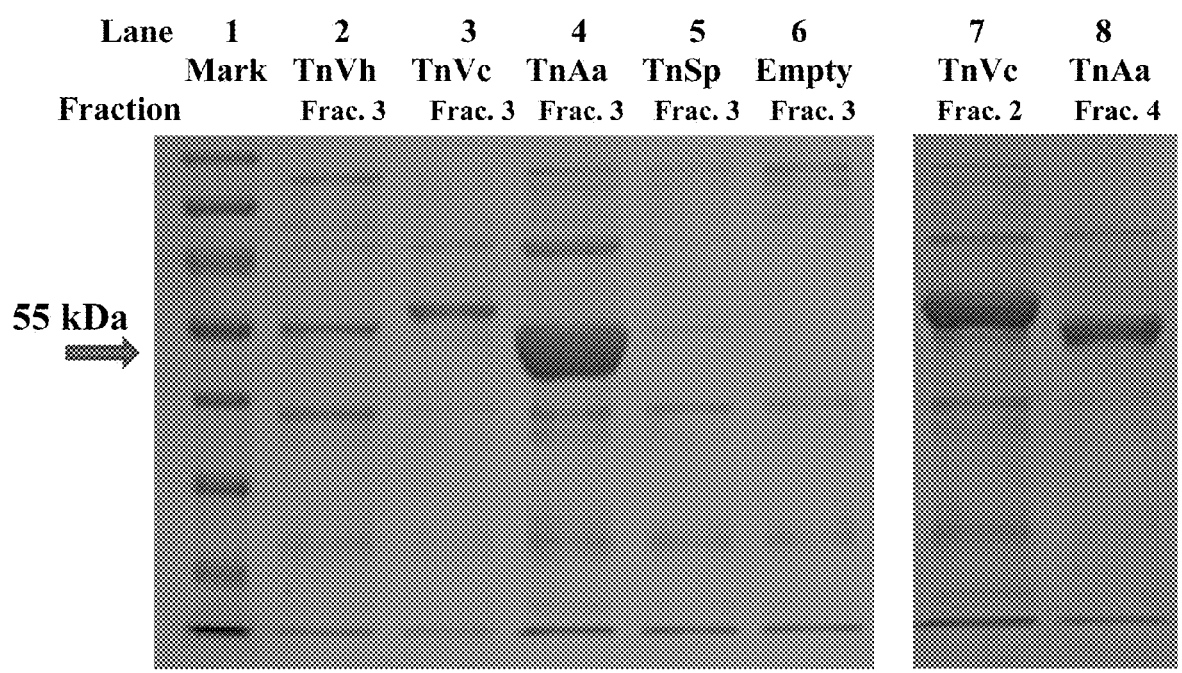
FIG. 1 is a photograph of a pair of gels showing the expression levels of the different cloned transposases; the wild-type transposase from *Alishewanella aestuarii* (TnAa-Tnp, Lanes 4 and 8) gave the highest yield among the different transposase candidates, while the wild-type transposase from *Vibrio cholerae* (TnVc-Tnp, Lanes 3 and 7) also gave a significant yield. Lane 1, marker; Lane 2, TnVh-Tnp fraction 3; Lane 3, TnVc-Tnp fraction 3; Lane 4, TnAa-Tnp fraction 3; Lane 5, TnSp fraction 3; Lane 6, pET29 empty vector; Lane7, TnVc-Tnp fraction 2; Lane 7, TnAa-Tnp fraction 4.

The disclosure provides a transpososome-based library preparation system. Existing methods of making the transpososome-based library preparation system may involve the steps of: (1) expressing a transposase, activating (also referred to herein as "loading") the transposase with DNA adapters (also referred to herein as "arms") that contain sequencer-specific sequences to form a transpososome and (2) contacting the transpososome and a target DNA to simultaneously fragment the target DNA and insert the adapter, a process referred to herein as "tagmentation." Because a single transpososome is capable of a single insertion only, existing methods present several problems. These problems include difficulty in controlling the insert size, sensitivity to DNA input and a significant insertion bias (caused by the preference of the transpososome for certain DNA sequences).

Disclosed are compositions and methods for reducing transpososome insertion bias by using competitive inhibition. Compositions and methods of the disclosure provide several superior properties compared to existing transposase-based library preparation systems, including, but not limited to, control of insert size, insensitivity to DNA target input amount, decreased insertion bias and increased library complexity, all of which significantly improve coverage and sequencing metrics of a resultant sequencing library.

The disclosure provides working examples to demonstrate how the compositions and methods provided herein overcome the problems plaguing existing technologies.

Transposon Technology

Insertion sequences (IS), and their related transposons (Tn), have been used as molecular tools since the advent of modern molecular genetics. There are different types of transposons, and these are generally grouped on the basis of the mechanism of transposition.

The IS4 group comprises insertion sequences and transposons that utilize a "cut and paste" mechanism for transposition. This involves the exact excision of the transposon from its original position, followed by insertion at a new location in the target DNA. The insertion can result in the creation of a short repeat region which brackets the insertion sequence at the insertion site. This process is driven by the action of the transposase (Tnp). The most well studied member of the IS4 family is the transposon Tn5 (and its associated insertion sequence IS50).

The molecular mechanism of Tn5-type transposition is well understood and has been described elsewhere (e.g. Reznikoff W. S. (2008) Ann. Rev. Genet. 42: 269-286). Briefly, two molecules of transposase form a binary complex which associates in a highly sequence-specific fashion with the 19 pb inverted repeats, or end sequences (ES) found at the end of the transposon. The transposase then cleaves the DNA at the limit of the ES to create a 3'-OH at each end, and release the transposon-DNA-transposase-dimer complex. This complex (and synthetic versions of it used as molecular tools) is variously termed the transpososome (Tsome), the transposome or the synaptic complex. Following release, the complex binds to target DNA and the insertion step occurs; here, interaction between the 3'-OH groups of the ES and the key acidic amino acids within the active site (known as the catalytic triad) is essential for the nicking and strand invasion.

Tn5 has been used extensively as a tool in molecular genetics, initially and primarily to create gene knock-outs, but in more recent times the uses have become more sophisticated (e.g. Reznikoff W. S. (2006) Biochem. Soc. Trans. 34: 320-323). The utility of the transposon and associated transposase has been augmented by the creation of mutant versions of the transposase to create a Tn5-transposase (Tn5-Tnp) that are more active. These are collectively and individually termed the hyperactive or hyper versions (hyper-Tn5 driven by hyper-Tn5-Tnp). The Tn5 transposase that caries the mutations E54K, M56A and L372P is a commonly utilized hyper version (see U.S. Pat. No. 5,965,443, the contents of which are incorporated herein by reference in their entirety).

Tn5 transposase has now been used to generate sequencing libraries for next generation sequencing (NGS) (Picelli et al. (2014) Genome Research. 2014. 24: 2033-2040). Briefly, purified transposase and synthetic ds-DNA ES are assembled in-vitro to form transpososomes. When these hyper-Tn5-Tsomes are contacted with a DNA target they insert in diverse, but not entirely random positions. Because the end sequences are separate, and not joined as they would be in a natural synaptic complex, the result is a cleavage of the DNA, with the ES installed at the cleaved end. From these cleaved fragments a sequencing library can be made, once adapters are added, by various methods. Such adapter sequences can be added to the ends of the ES prior to the assembly of the transpososome.

The transposase-based generation of DNA sequencing libraries faces a number of challenges that, prior to the instant disclosure, had not been solved. Technical challenges involve overcoming the fact that a single transpososome is capable of only a single insertion-cut event, and the complex is not subsequently released to insert and cut elsewhere. Consequently, existing technologies have difficulty controlling the insert size. The method is sensitive to DNA input amounts and significant insertion site bias exists. This bias is caused by the fact that while the transpososome can insert at diverse sites, it displays a variety of preferences for a variety DNA sequences, to the degree that a consensus preferred-sequence can be determined. The insertion pattern is thus semi-random, and the transpososome can be regarded a sequence-specific DNA-binding complex, albeit one with highly imperfect sequence discrimination.

Definitions

As used throughout the disclosure, the singular forms "a," "and," and "the" include plural referents unless the context clearly dictates otherwise. Thus, for example, reference to "a method" includes a plurality of such methods and reference to "a transposase" includes reference to one or more transposases and equivalents thereof known to those skilled in the art, and so forth.

The disclosure provides isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the disclosure or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments, variants, mutants (mutations) of the disclosed DNA sequences and proteins encoded by these DNA sequences. As used throughout the disclosure, the term "fragment" refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the disclosure.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

"Binding" refers to a specific, non-covalent interaction between macromolecules (e.g., between a protein and a nucleic acid, or between two proteins). Such specific binding is usually based on specific interactions between specific structural motifs that usually but not always, reflect those that occur in a natural biological setting.

"Sequence-specific binding" refers to a sequence specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. The term "sequence-specific binding" is not limited to strong, narrow sequence preferences but also includes the weak preferences displayed by molecules that can bind at a large variety of polynucleotide targets but with a preference for some over others. Such binding might also be termed "semi-random sequence-binding" or "biased sequence-binding".

The term "preferentially bind" refers to a hierarchical order of binding of a transposase or transpososome (active or inactive) to a sequence within a target DNA (e.g. genomic DNA). A transposase or transpososome (active or inactive) of the disclosure will preferentially bind to a certain site, and so these preferred sequences are more readily occupied than alternative sequences. As these preferred sequences become occupied the transposase or transpososome (active or inactive) has more freedom to bind to an alternative, and less preferred sequence. At a saturating concentration, the transposase or transpososome (active or inactive) will bind all available sequences; however, the preferred sites will tend to be occupied first. Thus, at low concentrations of the transposase or transpososome (active or inactive) of the disclosure, the sequences first occupied are "preferentially bound".

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this disclosure.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

Non-covalently linked components and methods of making and using non-covalently linked components, are disclosed. The various components may take a variety of different forms as described herein. For example, non-covalently linked (i.e., operatively linked) proteins may be used to allow temporary interactions that avoid one or more problems in the art. The ability of non-covalently linked components, such as proteins, to associate and dissociate enables a functional association only or primarily under circumstances where such association is needed for the desired activity. The linkage may be of duration sufficient to allow the desired effect.

A "binding site" or "binding sequence" is a target nucleic acid sequence that defines a portion of a nucleic acid to which a transposase, DNA adaptor, and/or transpososome will bind, provided sufficient conditions for binding exist.

A "consensus sequence" is a target nucleic acid sequence that defines a portion of a nucleic acid to which a transposase, DNA adaptor, and/or transpososome will bind, provided sufficient conditions for binding exist, that is present in more than one variation of a binding sequence or binding site. Although a transposase, DNA adaptor, and/or transpososome of the disclosure may prefer to bind to a first sequence, should all sites comprising that sequence be occupied the transposase, DNA adaptor, and/or transpososome of the disclosure may bind to a second sequence, the first and second sequence comprising a consensus sequence. For example, upon alignment of the first and the second sequences, although one or more bases may vary, the remaining bases that are invariant may comprise the consensus sequence.

The terms "target" and "input" DNA may be used interchangeably throughout the disclosure.

The terms "nucleic acid" or "oligonucleotide" or "polynucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Nucleic acids of the disclosure may be single-stranded or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence that are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "perfect complementarity" refers to a first and a second sequence that hybridize to one another without a gap or a mismatch of bases along the length of the nucleic acid duplex. For example, a first and a second sequence may hybridize to one another with perfect complementarity according to Watson-Crick base-pairing rules.

As used throughout the disclosure, the term "imperfect complementarity" refers to a first and a second sequence that hybridize to one another without one or more gaps or one or more mismatches of one or more bases along the length of the nucleic acid duplex. For example, a first and a second sequence may hybridize to one another with 70%, 75%, 80%, 85%, 90%, 95%, 99%, or any percentage in between of bases hybridized to one another along the length of the nucleic acid duplex.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some embodiments, fusion polypeptides and/or nucleic acids encoding such fusion polypeptides include conservative substitutions have been introduced by modification of polynucleotides encoding polypeptides of the disclosure. Amino acids can be classified according to physical properties and contribution to secondary and tertiary protein structure. A conservative substitution is a substitution of one amino acid for another amino acid that has similar properties. Exemplary conservative substitutions are set out in Table A.

TABLE A

Conservative Substitutions I

| Side chain characteristics | | Amino Acid |
|---|---|---|
| Aliphatic | Non-polar | G A P I L V F |
| | Polar - uncharged | C S T M N Q |
| | Polar - charged | D E K R |
| | Aromatic | H F W Y |
| | Other | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | | Amino Acid |
|---|---|---|
| Non-polar (hydrophobic) | Aliphatic: | A L I V P |
| | Aromatic: | F W Y |
| | Sulfur-containing: | M |
| | Borderline: | G Y |
| Uncharged-polar | Hydroxyl: | S T Y |
| | Amides: | N Q |
| | Sulfhydryl: | C |
| | Borderline: | G Y |
| Positively Charged (Basic): | | K R H |
| Negatively Charged (Acidic): | | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |

TABLE C-continued

Conservative Substitutions III

| Original Residue | Exemplary Substitution |
|---|---|
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used throughout the disclosure, the term "endogenous" refers to nucleic acid or protein sequence naturally associated with a target gene or a host cell into which it is introduced.

All percentages and ratios are calculated by weight unless otherwise indicated.

All percentages and ratios are calculated based on the total composition unless otherwise indicated.

Every maximum numerical limitation given throughout this disclosure includes every lower numerical limitation, as if such lower numerical limitations were expressly written herein. Every minimum numerical limitation given throughout this disclosure will include every higher numerical limitation, as if such higher numerical limitations were expressly written herein. Every numerical range given throughout this disclosure will include every narrower numerical range that falls within such broader numerical range, as if such narrower numerical ranges were all expressly written herein.

The values disclosed herein are not to be understood as being strictly limited to the exact numerical values recited. Instead, unless otherwise specified, each such value is intended to mean both the recited value and a functionally equivalent range surrounding that value. For example, a value disclosed as "20 μm" is intended to mean "about 20 μm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosure have been illustrated and described, various other changes and modifications can be made without departing from the spirit and scope of the disclosure. The scope of the appended claims includes all such changes and modifications that are within the scope of this disclosure.

EXAMPLES

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to: (1) methods described in *Maniatis* et al., Molecular Cloning—A Laboratory Manual, 2nd ed., Cold Spring Harbor Press (1989), using commercially available reagents (2) methods recommended by the suppliers of commercial kits and reagents, except where otherwise noted. Throughout these examples, protein expression, purification, assay and visualization and other standard protein production techniques, were carried out according to methods recommended by the suppliers of commercial kits and reagents, except where otherwise noted.

Example 1: Identification, Cloning and Expression of Transposases

Sequences representing 4 transposases have been identified that are found in different IS4-type insertion sequences. The insertion sequences were found in the genomes of the following bacteria: *Alishewanella aestuarii, Vibrio cholera, Vibrio harveyi, Shewanella putrefaciens*. The transposases are substantially different to the well understood Tn5 transposase, as shown below in Table 1.

TABLE 1

| Original source | Transposase candidates | Amino acid identity to Hyperactive Tn5-Tnp (blastp) |
| --- | --- | --- |
| *Alishewanella aestuarii* | TnAa-Tnp | 42% |
| *Vibrio cholera* | TnVc-Tnp | 39% |
| *Vibrio harveyi* | TnVh-Tnp | 40% |
| *Shewanella putrefaciens* | TnSp-Tnp | 41% |

The protein sequences of the relevant transposases are provided below:

Hyperactive Tn5-Tnp is a mutant version of the wild type transposase in which the mutations E54K, M56A and L327P are incorporated (mutations bold and underlined in sequence below).

(SEQ ID NO: 15)
MITSALHRAADWAKSVFSSAALGDPRRTARLVNVAAQLAKYSGKSITISS

EGSKAAQEGAYRFIRNPNVSAEAIRKAGAMQTVKLAQEFPELLAIEDTTS

LSYRHQVAEELGKLGSIQDKSRGWWVHSVLLLEATTFRTVGLLHQEWWMR

PDDPADADEKESGKWLAAAATSRLRMGSMMSNVIAVCDREADIHAYLQDK

LAHNERFVVRSKHPRKDVESGLYLYDHLKNQPELGGYQISIPQKGVVDKR

GKRKNRPARKASLSLRSGRITLKQGNITLNAVLAEEINPPKGETPLKWLL

LTSEPVESLAQALRVIDIYTHRWRIEEFHKAWKTGAGAERQRMEEPDNLE

RMVSILSFVAVRLLQLRESFTPPQALRAQGLLKEAEHVESQSAETVLTPD

ECQLLGYLDKGKRKRKEKAGSLQWAYMAIARLGGFMDSKRTGIASWGALW

EGWEALQSKLDGFLAAKDLMAQGIKI.

TnAa-Tnp is from *Alishewanella aestuarii* (wild type sequence below):

(SEQ ID NO: 16)
MNNAQWAKSTFGQADLGDPRRTTRLVKLAETLANDPGKPFVSITQSPADM

EGAYRFIRNEHVNADAIAKAGYLVTAAQAAKHNLLLALEDTTAITYSHRS

VRDELGHVNQGNNYRGILAHSVLLFAPEQQELVGLIEQSRWTRDISTRGK

KHVRTQTPYEEKESFKWQSASVNLSARLGTKMADVISVCDREADIYEYLQ

YKLSKQHRFVVRSMQSRHIEQSEQKLYDYAAGLESAGQKQIHIAQKGGRK

-continued

ARTATVDIVFAPVTLQVPANKRGESLSLYYVGCEERADDKNALNWHLLTT

EPVQSKADALNIIRYYEHRWLVEEYHKAWKTDGTDIENARLQSKDNIERL

VTISAFIAVRIVQLKFAREQPDEISCEQVLSPKAWKLLWIKRVSRTLPDT

VPSMKWAYTELAKLGGWKDTKQTGKASVKVLWQGWFKLQTILEGYDLAKS

LEADL.

TnVc-Tnp is from *Vibrio cholerae* (wild type sequence below):

(SEQ ID NO: 17)
MTYIEPTLWAQKQFGQAHLNDPRRTQRLVALAASLAEQPGVPVSKLII

SPADMEGAYRFIRNEQIKAEDIAEAGFHVTAQEALEQQTLLALEDTTS

LSYSHRSIQDELGHSNQGNRNRAMFIHSTLLFAPETQVVVGLIEQQRW

TRDIEKRGQGHQYATRPYKEKESYKWEQASRHVAERLGDKISDVISVC

DREADLFEYLTYKQEQQQRFLVRSMQSRCIEEHDNRLYDYASKLQSAG

ERVLDIPQKGGRKARTVHLDIKYAPVTLKSPANKKEFNNIPLYYVGCI

EQGESNDKLAWHLLTSEPITSKEEALKIVSYYELRWLIEDFHKVWKSE

GTQVEQLRMQSKDNLERLSVILAFIATRLLQLRFMNESDELSKSSCEP

ILKGKAWKLMWLKLERKGLPKEAPDISWAYKGIARLGGWKNTKRTGRA

SIKTLWQGWFRLQTILEGYELAKSLDSPD.

TnVh-Tnp is from *Vibrio harveyi* (wild type sequence below):

(SEQ ID NO: 18)
MTHSDAKLWAQEQFGQAQLKDPRRTQRLISLATSIANQPGVSVAKLPF

SPADMEGAYRFIRNENINAEDIAEAGFQSTVSRANEHKELLALEDTTT

LSFPHRSIKEELGHTNQGDRTRALHVSTLLFAPQSQTIVGLIEQQRW

SRDITKRGQKHQHATRPYKEKESYKWEQASRRVVERLGDKMLDVISVC

DREADLFEYLTYKRQHQQRFVVRSMQSRCLEEHAQKLYDYAQALPSVE

TKALTIPQKGGRKARNVKLDVKYGQVTLKAPANKKEHAGIPVYYVGCL

EQGTSKDKLAWHLLTSEPINNVDDAMRIIGYYERRWLIEDFHKVWKSE

GTDVESLRLQSKDNLERLSVIYAFVATRLLALRFMKEVDELTKESCEK

VLGQKAWKLLWLKLESKTLPKEVPDMGWAYKNLAKLGGWKDTKRTGRA

SIKVLWEGWFKLQTILEGYELAMSLDH.

TnSp-Tnp is from *Shewanella putrefaciens* (wild type sequence below):

(SEQ ID NO: 19)
MIKSNNDWAEEQFGHAKLGDPRRTARLVKMASDLAQHPGKSVVKSSPS

PASMEGAYRFIRNDNVSADDIAEAGFRATVNQAHRYPLLLAIEDTTTL

SYKHRSIRADLGHVNQGNRYRGLLAHSILLFAPETLDVVGLIEQHRWT

RDIKTRGIRRENLKRPYEEKEGYKWESASRNMAARLGTAMANVISVCD

READIYDYLLYKIANQQRFVVRSMMSRHIEEGSDKLYHFASELNSVKQ

RQIQIAQRGGRKAREVTLDVKYAAVTLKTPANKKGSPISLNYVGCSEV

GDEEKTLNWHILTNEPVNSAEDALKIIGYYEKRWLIEEYHKVWKSEGT

GVEDLRVQSKDNLDRLATIYAFLAVRIFQLKFANEQIEDISSEKILSP

RAWKLLWLKRIKTPPPEEVPTAKWAYEHLARLGGWKDSKRNGRASVKT

LWEGWLKLQAILEGYELALSLEQDL.

The candidate transposase genes were cloned in a pET29 (Novagen) expression vector, fused to a C-terminal HIS tag, in an *E. coli* host. Expression of the cloned genes was induced by auto induction. The transposases were purified by standard methods. Briefly: pellets from 50 ml induced cultures were collected by centrifugation and resuspended in 4 ml 1× LEW buffer (50 mM NaH$_2$PO$_4$, 300 mM NaCl, pH 8.0) on ice. Cells were lysed by 2 cycles of freezing at −80° C. and thawing and were then treated with benzonase in the presence of 10 mM MgCl$_2$ for 30 min on ice. After centrifugation, the supernatant was loaded on pre-equilibrated Protino Ni-TED 2000 packed gravity flow columns at 4° C. Columns were washed twice with 4 ml 1× LEW buffer at 4° C., and eluted with 1× Elution buffer (50 mM NaH$_2$PO$_4$, 300 mM NaCl, 250 mM imidazole, pH 8.0) at 4° C. 500 µl elution fractions were collected and the protein concentration of each fraction measured by spectrophotometry to identify the fractions that carried the most His-tagged protein.

10 µl samples of the fractions were loaded and separated on a 10% SDS-PAGE gel. The results are shown in FIG. 1. Only those fractions that contained the highest levels of transposase for each sample are shown. The transposases are expected to be about 55 kDa. As seen from the SDS-PAGE analysis, the wild-type transposase from *Alishewanella aestuarii* (FIG. 1, TnAa-Tnp, Lanes 4 and 8) gave the highest yield among the different transposase candidates, while the wild-type transposase from *Vibrio cholerae* (FIG. 1, TnVc-Tnp, Lanes 3 and 7) also gave significant yield. Very little transposase was expressed by the other candidates.

Example 2: Testing the Transposases for Tagmentation Ability

The wild type transposases TnVc-Tnp and TnAa-Tnp were tested for their ability to tagment 800 ng of lambda DNA. This was done by loading the transposases with different types of DNA arms, tagmenting the lambda DNA and subjecting the purified tagmented DNA to PCR to amplify the tagmented DNA. Following this, the PCR product was visualized by gel electrophoresis. Briefly:

Types of arms: Four different types of arms were separately loaded in the case of each transposase, these were based on: (a) The mosaic ends of hyper Tn5, the arms are termed ME Hyp; (b) The mosaic ends of the transposon from *Vibrio harveyi*, the arms are termed ME Har; (c) The outer end of hyper Tn5, the arms are termed OE Hyp; (d) Inner end of the transposon from *Vibrio harveyi*, the arms are termed IE Har.

Expression and purification: 200 ml induced cultures were used to purify TnAa-Tnp and TnVc-Tnp essentially as described for Example 1. After purification transposase-containing fractions were pooled and concentrated using Microcon YM-10 centrifugal filters. Buffer exchange was performed using NICK size exclusion columns containing sephadex G-50 DNA. The purified samples were eluted in 50 mM Tris-Cl pH 7.4, 250 mM KCl, and collected in 50 µl fractions.

Preparing the arms: Oligonucleotides were obtained from IDT. The two oligonucleotides that comprise each arm were annealed by mixing equimolar amounts together with the addition of 20× K-glutamate salt (500 mM K-glutamate; 200 mM Tris-Acetate, pH7.5), and incubated in a thermocycler for 60s at 25° C., then 30s at 90° C., followed by a 2% slow ramp to 20° C., after which it was held for 5 min at 20° C., and finally held at 4° C.

Loading the arms to make the transpososome: 6.7 µl of TnAa-Tnp (1.79 mg/ml) was mixed with 6.7 µl of each set of arms; 4 µl of TnVc-Tnp (4.96 mg/ml) was mixed with 4 µl of each set of arms, and the mixture was incubated at ambient temperature for 70 min.

Tagmentation reaction: 20 µl of 4× Transposition buffer (25 mM Tris-Acetate pH 7.5, 25 mM potassium glutamate, 10 mM $MnCl_2$) was mixed with 20 µl lambda DNA (40 µg/ml), 10 µl of annealed arms and 30 µl $H_2O$. 70 µl of this mixture was added to 8 µl loaded transposase, and incubated at 47° C. for 25 min. Controls reactions were the same except that unloaded transposase (unloaded Aa, unloaded Vc) or no transposase (no enzyme) was used.

Amplification: The reactions were purified with a Qiagen enzymatic purification kit, and PCR was performed using arm-specific primers, 5 µl of purified tagmentation reaction/20 µl PCR, and Kapa Biosystems 2G Robust polymerase, according to the manufacturer's instructions. The sample was cycled as follows: 72° C. for 4 min, (94° C. for 40 sec, 56° C. for 45 sec, 72° C. for 2 min)×20, 72° C. for 10 min.

Figure 2:
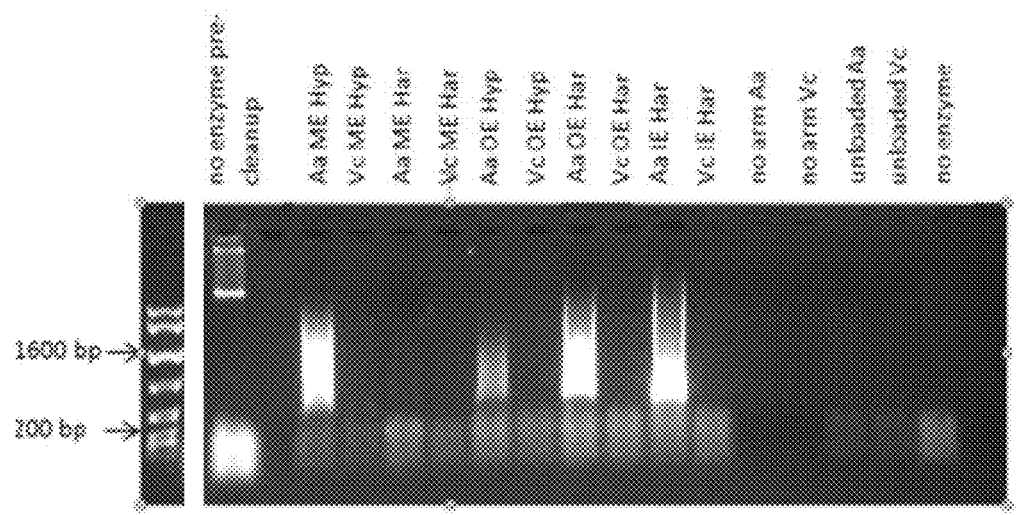
FIG. 2 is a photograph of a gel on which the PCR products of a tagmentation reaction are separated. Two transposase types (TnAa-Tnp and TnVc-Tnp) are shown as Aa and Vc. Four different arm types were used (ME Hyp, ME Har, OE Hyp and IE Har). Mixed long fragments, manifesting as a "smear", denote successful tagmentation and amplification. The results show that only TnAa-Tnp produced long fragments with any of the tested arm combinations. The arms ME Hyp, OE Har and IE Har appeared to be particularly suited for the method.

Visualization: Following amplification the PCR products were separated on a 0.8% agarose gel. The results are shown in FIG. 2.

Functional transposases are expected to produce large amounts different sized PCR products and these would appear as a "smear" on the gel. This can be seen in FIG. 2, where the fragment sizes can be larger than 2 kb. Where tagmentation has failed only short products are seen. Tagmentation was successful only with the wild type TnAa-Tnp. The arms ME Hyp, OE Har and IE Har appeared to be particularly suited for the method

Example 3: Buffer Modification and Inclusion of Glycerol

Different buffer additives were tested to determine if tagmentation efficiency with the wild type TnAa transpososome could be further improved. A standard tagmentation reaction was conducted, but different additives were included in the buffer. Preliminary results showed that glycerol improved the tagmentation greatly. Further tests were therefore conducted. Briefly, the tagmentation was conducted essentially as described for Example 2, with the following differences:

Arms: ME-Hyp arms were used.

Loading the arms to make the transpososome: 1.44 mg/ml TnAa-Tnp (27 µM, in 20 mM PIPES pH 7.5, 250 mM KCl, 50% glycerol) was combined with an equal volume of ME Hyp arms (50 µM), and incubated at ambient temperature for 80 min.

Tagmentation reaction: 1 µl E. coli DNA (50 ng) was mixed with 4 µl loaded TnAa-Tnp and 1.2 µl ME Hyp arms (50 µM). This was ultimately made up to a final volume of 20 µl and a final composition of 25 mM Tris-Acetate pH 7.5, 10 mM $MnCl_2$, 10 mM NaCl, 15% DMSO and 0.05% NP40/Igepal CA 630, with various glycerol concentrations. Five different mixes were made with glycerol concentrations of 0%, 5%, 10%, 20% and 40%. The mixes were incubated at 47° C. for 50 min.

Amplification and visualization: This was essentially as for Example 2, except that the sample was separated on an Agilent Bioanalyzer 2100 using a High Sensitivity DNA Chip, or a Perkin Elmer Labchip GXII Touch HT using a DNA HiSens Chip.

Figure 3:
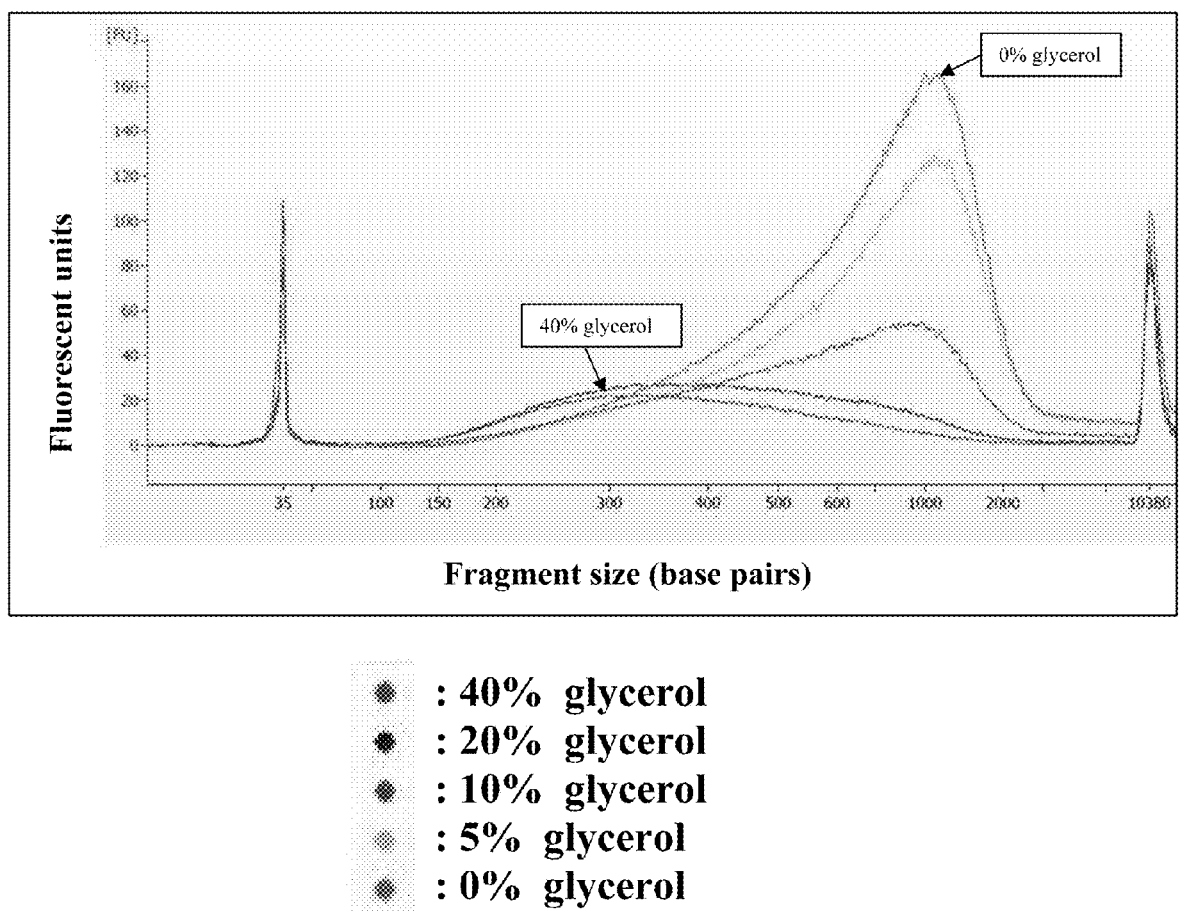
FIG. 3 is graph depicting an Agilent Bioanalyzer trace of fluorescence units plotted against DNA fragment size. The trace shows the effect of glycerol concentration on the efficiency of tagmentation by TnAa transpososome. The addition of glycerol in the buffer increased tagmentation efficiency, which manifested as a size shift of amplified library fragments from larger fragments (0% glycerol, cyan line, lower efficiency) to progressively smaller fragments (40% glycerol, red line, higher efficiency).

The results are shown in FIG. 3. It was found that addition of glycerol to buffer used during tagmentation increased tagmentation efficiency. In this experiment, increased efficiency would manifest as a decrease in library fragment size, due to more tagmentation and so greater levels of target shearing. The enhancing effect of glycerol can be seen in FIG. 3, where glycerol free buffer results in large fragments (cyan line, lower efficiency) whereas the inclusion of increasing amounts of glycerol results in ever shorter fragments, with 40% glycerol resulting in the shortest fragments (red line, higher efficiency).

Example 4: Mutation of the TnAa Transposase

In Tn5-Tnp, the E54K mutation increases the ability of the enzyme to load arms and thus increase the overall transposition efficiency; it is one of the mutations used to create hyperactive versions of Tn5-Tnp. In order to increase the activity and library preparation efficiency of the TnAa-Tsome, the equivalent mutation was inserted into TnAa-Tnp.

The equivalent position in TnAa-Tnp was identified by alignment as shown below. In TnAa-Tpn, the equivalent position (position 47) comprises a proline residue. We have changed this to lysine to create a P47K mutant of the TnAa transposase (TnAa-Tnp-P47K).

In another hyperactive Tn5-Tnp, two other mutations are included in addition to E54K. These are M56A and L372P. While there is no position corresponding to the L372 position in TnAa-Tnp (below, boxed), the corresponding position of M56 in Tn5-Tnp is M50 in TnAa-Tnp. This internal methionine may be an internal translation initiation site that results in the production of a truncated inhibitor protein (shown in bold italics, below). This position has been changed in both the wild type TnAa-Tnp and TnAa-Tnp-P47K mutant to create the mutant versions TnAa-Tnp-M50A and TnAa-Tnp-P47K/M50A.

For alignment below of Tn5-Tnp-E54K/M56A, Tn5 wt (SEQ ID NO: 20), Hperactive_Tn5 (SEQ ID NO: 21), TnAa_wt (SEQ ID NO: 22), Shew_putre (SEQ ID NO: 23), Vib_chol (SEQ ID NO: 24), Vib_harveyi (SEQ ID NO: 25).

| Tn5-Tnp-E54K/M56A |
|---|

```
Tn5_wt           MITSALHRAADWAKSVFSSAALGDPRRTARLVNVAAQLAKYSGKSITISSEGSEAMQEGA
Hyperactive_Tn5  MITSALHRAADWAKSVFSSAALGDPRRTARLVNVAAQLAKYSGKSITISSEGSKAAQEGA
TnAa_wt          ------MNNAQWAKSTFGQADLGDPRRTTRLVKLAETLANDPGKPF-VSITQSPADMEGA
Shew_putre       MI----KSNNDWAEEQFGHAKLGDPRRTARLVKMASDLAQHPGKSV-VKSSPSPASMEGA
Vib_chol         MTY---IEPTLWAQKQFGQAHLNDPRRTQRLVALAASLAEQPGVPV-SKIISPADMEGA
Vib_harveyi      MTH---SDAKLWAQEQFGQAQLKDPRRTQRLISLATSIANQPGVSV-AKLPFSPADMEGA
                  **:  *  * ***** **: :* .*: .* ..     * *.***

Tn5_wt           YRFIRNPNVSAEAIRKAGAMQTVKLAQEFPELLAIEDTTSLSYRHQ-VAEELGKLGSIQD
Hyperactive_Tn5  YRFIRNPNVSAEAIRKAGAMQTVKLAQEFPELLAIEDTTSLSYRHQ-VAEELGKLGSIQD
TnAa_wt          YRFIRNEHVNADAIAKAGYLVTAAQAAKHNLLLALEDTTAITYSHRSVRDELGHVNQ-GN
Shew_putre       YRFIRNDNVSADDIAEAGFRATVNQAHRYPLLLAIEDTTTLSYKHRSIRADLGHVNQ-GN
Vib_chol         YRFIRNEQIKAEDIAEAGFHVTAQEEALEQQTLLALEDTTSLSYSHRSIQDELGHSNQ-GN
Vib_harveyi      YRFIRNENINAEDIAEAGFQSTVSRANEHKELLALEDTTTLSFPHRSIKEELGHTNQ-GD
                 ******  ::.*: * :**     *.     ***:****:::: *:  : :**:  .. :

Tn5_wt           KSRGWWVHSVLLLEATTFRTVGLLHQEWWMRP---------DDPADADEKESGKWLAAAA
Hyperactive_Tn5  KSRGWWVHSVLLLEATTFRTVGLLHQEWWMRP---------DDPADADEKESGKWLAAAV
TnAa_wt          NYRGILAHSVLLFAPEQQELVGLIEQSRWTRDISTRGKKHVRTQTPYEEKESFKWQSASV
Shew_putre       RYRGLLAHSILLFAPETLDVVGLIEQHRWTRDIKTRGIRRENLKRPYEEKEGYKWESASR
Vib_chol         RNRAMFIHSTLLFAPETQVVVGLIEQQRWTRDIEKRGQHQYATRPYKEKESYKWEQASR
Vib_harveyi      RTRALHVHSTLLFAPQSQTIVGLIEQQRWSRDITKRGQKHQHATRPYKEKESYKWEQASR
                 . *.      ** **:  .    ***:.*   * *              .***. ** *:

Tn5_wt           TSRLRMGSMMSNVIAVCDREADIHAYLQDKLAHNERFVVRSKHPRKDVESGLYLYDHLKN
Hyperactive_Tn5  TSRLRMGSMMSNVIAVCDREADIHAYLQDKLAHNERFVVRSKHPRKDVESGLYLYDHLKN
TnAa_wt          NLSARLGTKMADVISVCDREADIYEYLQYKLSKQHRFVVRSMQSRHIEQSEQKLYDYAAG
Shew_putre       NMAARLGTAMANVISVCDREADIYDYLLYKIANQQRFVVRSMMSRHIEEGSDKLYHFASE
Vib_chol         HVAERLGDKISDVISVCDREADLFEYLTYKQEQQQRFLVRSMQSRCIEEHDNRLYDYASK
Vib_harveyi      RVVERLGDKMLDVISVCDREADLFEYLTYKRQHQQRFVVRSMQSRCLEEHAQKLYDYAQA
                  *:*   :*:**:*******:. **  *   :  :.**.***  .*    **..

Tn5_wt           QPELGGYQISIPQKGVVDKRGKRKNRPARKASLSLRSGRITLKQ-------GNITLNAVL
Hyperactive_Tn5  QPELGGYQISIPQKGVVDKRGKRKNRPARKASLSLRSGRITLKQ-------GNITLNAVL
TnAa_wt          LESAGQKQIHIAQKG---------GRKARTATVDIVFAPVTLQVPANKRG-ESLSLYYVG
Shew_putre       LNSVKQRQIQIAQRG---------GRKAREVILDVKYAAVTLKTPANKKG-SPISLNYVG
Vib_chol         LQSAGERVLDIPQKG---------GRKARTVHLDIKYAPVTLKSPANKKEFNNIPLYYVG
Vib_harveyi      LPSVETKALTIPQKG---------GRKARNVKLDVKYGQVTLKAPANKKEHAGIPVYYVG
                           : *.*:*         .*  ** .  :: .. :**:        :.:   *

Tn5_wt           AEEINPPKGETPLKWLLLTSEPVESLAQALRVIDIYTHRWRIEEFHKAWKT-GAGAERQR
Hyperactive_Tn5  AEEINPPKGETPLKWLLLTSEPVESLAQALRVIDIYTHRWRIEEFHKAWKT-GAGAERQR
TnAa_wt          CEERA--DDKNALNWHLLTTEPVQSKADALNIIRYYEHRWLVEEYHKAWKTDGTDIENAR
Shew_putre       CSEVG--DEEKTLNWHILTNEPVNSAEDALKIIGYYEKRWLIEEYHKVWKSEGTGVEDLR
Vib_chol         CIEQG--ESNDKLAWHLLTSEPITSKEEALKIVSYYELRWLIEDFHKVWKSEGTQVEQLR
Vib_harveyi      CLEQG--TSKDKLAWHLLTSEPINNVDDAMRIIGYYERRWLIEDFHKVWKSEGTDVESLR
                  . *     :  * * :*.**. .  :*: .: :   * **  :*:.**..*: :  *
```

For alignment below of Tn5-Tnp-L372, Tn5_wt (SEQ ID NO: 26), Hperactive_Tn5 (SEQ ID NO: 27), TnAa_wt (SEQ ID NO: 28), Shew_putre (SEQ ID NO: 29), Vib_chol (SEQ ID NO: 30), Vib_harveyi (SEQ ID NO: 31).

| Tn5-Tnp-L372 |
|---|

```
Tn5_wt           MEEPDNLERMVSILSFVAVRLLQLRESFTLPQALRAQGLLKEAEHVESQSAETVLTPDEC
Hyperactive_Tn5  MEEPDNLERMVSILSFVAVRLLQLRESFTPPQALRAQGLLKEAEHVESQSAETVLTPDEC
TnAa_wt          LQSKDNIERLVTISAFIAVRIVQLK------------HARE--QPDEISCEQVLSPKAW
Shew_putre       VQSKDNLDRLATIYAFLAVRIFQLK------------HANE--QIEDISSEKILSPRAW
Vib_chol         MQSKDNLERLSVILAFIATRLLQLR------------HMNESDELSKSSCEPILKGKAW
Vib_harveyi      LQSKDNLERLSVIYAFVATRLLALP------------HMKEVDELTKESCEKVLGQKAW
                 ::. **::*:  * :*:*.*:.*. *                 .*    *.* :*

Tn5_wt           QLLGYLDKGKRKRKEKAGSLQWAYMAIARLGGFMDSKRTGIASWGALWEGWEALQSKLDG
Hyperactive_Tn5  QLLGYLDKGKRKRKEKAGSLQWAYMAIARLGGFMDSKRTGIASWGALWEGWEALQSKLDG
TnAa_wt          KLL-WIKRVSRTLPDTVPSMKWAYTELAKLGGWKDTKQTGKASVKVLWQGWFKLQTILEG
Shew_putre       KLL-WLKRIKTPPPEEVPTAKWAYEHLARLGGWKDSKRNGRASVKTLWEGWLKLQAILEG
Vib_chol         KLM-WLKLERGLPKEAPDISWAYKGIARLGGWKNTKRTGRASIKTLWQGWFRLQTILEG
Vib_harveyi      KLL-WLKLESKTLPKEVPDMGWAYKNLAKLGGWKDTKRTGRASIKVLWEGWFKLQTILEG
                 :*: ::.           . ***   :*:*** :*:.:** **: *.* ***: :*
```

Tn5-Tnp-L372

```
Tn5_wt            FLAAKDLMAQGIKI
Hyperactive_Tn5   FLAAKDLMAQGIKI
TnAa_wt           YDLAKSLEAD---L
Shew_putre        YELALSLEQD---L
Vib_chol          YELAKSLDSP---D
Vib_harveyi       YELAMSLDH-----
                  :  *  .*
```

The sequences of the mutant transposases TnAa-Tnp-P47K, TnAa-Tnp-M50A, and TnAa-Tnp-P47K/M50A are provided below.

TnAa-Tnp-P47K
(SEQ ID NO: 32)
MNNAQWAKSTFGQADLGDPRRTTRLVKLAETLANDPGKPFVSI

TQSKADMEGAYRFIRNEHVNADAIAKAGYLVTAAQAAKHNLLL

ALEDTTAITYSHRSVRDELGHVNQGNNYRGILAHSVLLFAPEQ

QELVGLIEQSRWTRDISTRGKKHVRTQTPYEEKESFKWQSASV

NLSARLGTKMADVISVCDREADIYEYLQYKLSKQHRFVVRSMQ

SRHIEQSEQKLYDYAAGLESAGQKQIHIAQKGGRKARTATVDI

VFAPVTLQVPANKRGESLSLYYVGCEERADDKNALNWHLLTTE

PVQSKADALNIIRYYEHRWLVEEYHKAWKTDGTDIENARLQSK

DNIERLVTISAFIAVRIVQLKFAREQPDEISCEQVLSPKAWKL

LWIKRVSRTLPDTVPSMKWAYTELAKLGGWKDTKQTGKASVKV

LWQGWFKLQTILEGYDLAKSLEADL

TnAa-Tnp-M50A
(SEQ ID NO: 33)
MNNAQWAKSTFGQADLGDPRRTTRLVKLAETLANDPGKPFVSI

TQSPADAEGAYRFIRNEHVNADAIAKAGYLVTAAQAAKHNLLL

ALEDTTAITYSHRSVRDELGHVNQGNNYRGILAHSVLLFAPEQ

QELVGLIEQSRWTRDISTRGKKHVRTQTPYEEKESFKWQSASV

NLSARLGTKMADVISVCDREADIYEYLQYKLSKQHRFVVRSMQ

SRHIEQSEQKLYDYAAGLESAGQKQIHIAQKGGRKARTATVDI

VFAPVTLQVPANKRGESLSLYYVGCEERADDKNALNWHLLTTE

PVQSKADALNIIRYYEHRWLVEEYHKAWKTDGTDIENARLQSK

DNIERLVTISAFIAVRIVQLKFAREQPDEISCEQVLSPKAWKL

LWIKRVSRTLPDTVPSMKWAYTELAKLGGWKDTKQTGKASVKV

LWQGWFKLQTILEGYDLAKSLEADL

TnAa-Tnp-P47K/M50A
(SEQ ID NO: 34)
MNNAQWAKSTFGQADLGDPRRTTRLVKLAETLANDPGKPFVSI

TQSKADA**EGAYRFIRNEHVNADAIAKAGYLVTAAQAAKHNLLL

ALEDTTAITYSHRSVRDELGHVNQGNNYRGILAHSVLLFAPEQ

QELVGLIEQSRWTRDISTRGKKHVRTQTPYEEKESFKWQSASV

NLSARLGTKMADVISVCDREADIYEYLQYKLSKQHRFVVRSMQ

SRHIEQSEQKLYDYAAGLESAGQKQIHIAQKGGRKARTATVDI

VFAPVTLQVPANKRGESLSLYYVGCEERADDKNALNWHLLTTE

PVQSKADALNIIRYYEHRWLVEEYHKAWKTDGTDIENARLQSK

DNIERLVTISAFIAVRIVQLKFAREQPDEISCEQVLSPKAWKL

LWIKRVSRTLPDTVPSMKWAYTELAKLGGWKDTKQTGKASVKV

LWQGWFKLQTILEGYDLAKSLEADL

The mutant transposases were expressed and purified essentially as describe above. While the M50A mutants initially proved difficult to work with, the P47K mutant transposase could be purified to useful levels. TnAa-Tnp-P47K was used to conduct tagmentation experiments and compared with the wild type TnAa-Tnp in the same experiment, essentially as described previously. Briefly, the tagmentation was conducted essentially as described for Example 2 and 3, with the following differences:

Arms: ME/R1R2 arms were used. This comprises an equimolar mixture of two types of arms, each is a standard mosaic end (ME) in conjunction with a different sequencing adapter (R1 or R2), as shown below

```
R1:     5'-TCGTCGGCAGCGTCAGATGTGTATAAGAGACAG-OH-3'   (SEQ ID NO: 35)
                         |||||||||||||||||||
ME_RC:                 3'-TCTACACATATTCTCTGTC    -5'   (SEQ ID NO: 36)

R2:     5'-GTCTCGTGGGCTCGGAGATGTGTATAAGAGACAG-OH-3'  (SEQ ID NO: 37)
                          |||||||||||||||||||
ME_RC:                  3'-TCTACACATATTCTCTGTC   -5'   (SEQ ID NO: 38)
```

Loading the arms to make the transposome: Loading was at a 1:2 enzyme:arm ratio. 1.5 mg/ml TnAa-Tnp was combined with an equal volume of ME/R1R2 arms (50 µM), and 0.75 mg/ml TnAa-Tnp-P47K was combined with an equal volume of ME/R1R2 arms (25 µM).

Tagmentation reaction: 1 µl E. coli DNA (50 ng) was mixed with 2 µl loaded TnAa-Tnp, or 4 µl loaded TnAa-Tnp-P47K. This was ultimately made up to a final volume of 20 µl and a final composition of 25 mM Tris-Acetate pH 7.5, 10 mM $MnCl_2$, 20% glycerol, 15% DMSO and 0.05% NP40. The mixes were incubated at 47° C. for 5 min Amplification: The reactions were purified with a Qiagen enzymatic clean-up kit as described above, in Example 2, but eluted in 15 µl. PCR was performed using R1 and R2 arm-specific primers, using 13 µl of purified tagmentation reaction/50 µl PCR, and Kapa Biosystems HiFi PCR kit, according to the manufacturer's instructions. The sample was cycled as follows: 72° C. for 3 min, 98° C. for 30 sec, (98° C. for 15 sec, 56° C. for 30 sec, 72° C. for 3 min)×6, 72° C. for 10 min. Following amplification, DNA was purified using 2× volumes of AMPure XP Reagent (Beckman Coulter), and finally eluted in 10 µl of 10 mM Tris-HCl, pH8, according to the manufacturer's instructions.

Visualization: This was essentially as for Example 3; sample was separated on an Agilent Bioanalyzer 2100 or a Perkin Elmer Labchip GXII Touch HT.

Figure 4:
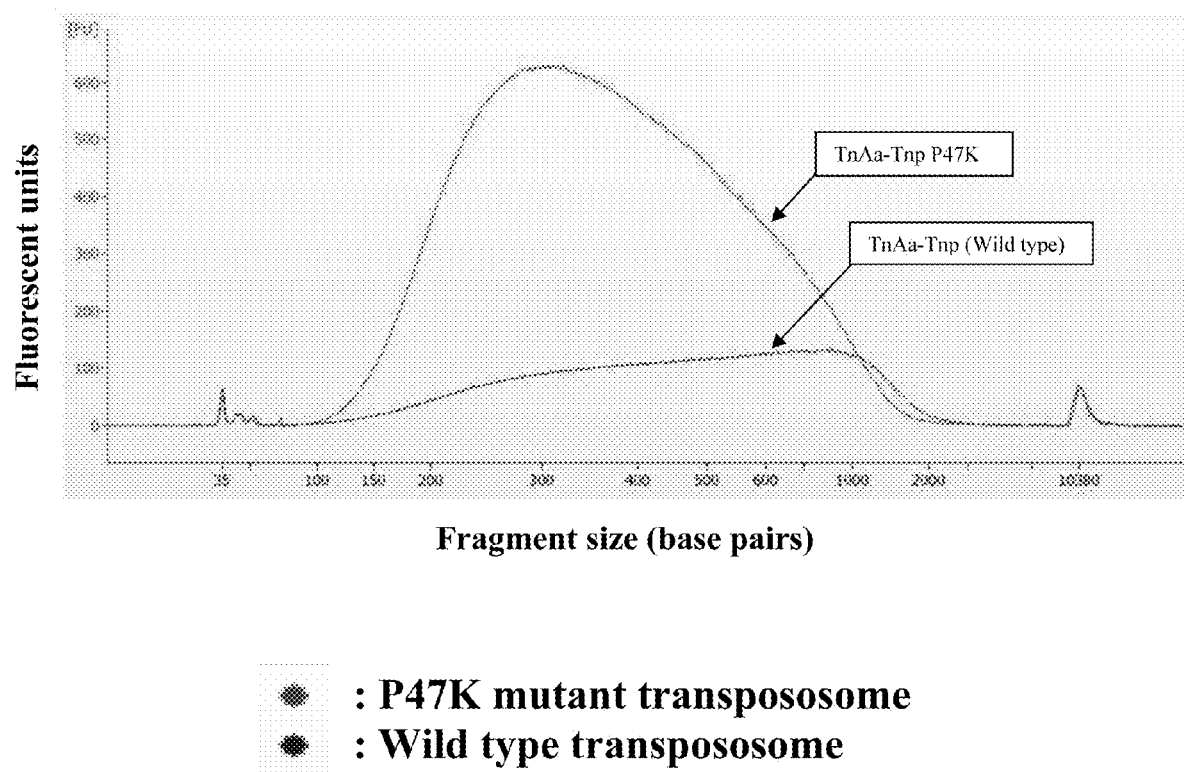
FIG. 4 is a graph depicting an Agilent Bioanalyzer trace of fluorescence units plotted against DNA fragment size. The trace shows the different efficiencies of tagmentation by TnAa transpososomes, depending upon whether a wild type or mutant (P47K) version of the TnAa transposase is utilized. The mutant version generates smaller fragments than the wild type (red line, higher efficiency) than the wild type (blue line, lower efficiency).

The results are shown in FIG. 4. The Bioanalyzer trace proves that the P47K mutant transposome exhibited better tagmentation efficiency, as shown by the production of shorter fragments (FIG. 4; red line=TnAa-Tnp-P47K mutant) than the wild type complex (FIG. 4; blue line=TnAa-Tnp wild type).

Example 5: Preferred Tagmentation Methodology

During the course of the development of the TnAa-Tnp and its use for tagmentation an optimized protocol was developed. This protocol was used as a basis for subsequent work (with modifications as required for particular experiments). The protocol has several steps, as follows:

Arm preparation: Oligonucleotides are obtained from commercial suppliers. Each oligonucleotide is resuspended in 20 mM PIPES pH7.5 to 100 µM. The oligonucleotides are then duplexed by mixing two complimentary oligonucleotides in equal volumes, with the addition of 20× K-glutamate salt (500 mM K-glutamate; 200 mM Tris-Acetate, pH7.5), and incubating the mixture in a thermocycler for 60s at 25° C., then 30s at 90° C., followed by a 2% slow ramp to 20° C., after which the mixture is held for 5 min at 20° C. The oligonucleotide duplex (now termed "arms") is diluted to 25 µM with 20 mM PIPES pH7.5, and stored at −20° C. Different oligonucleotides and arms can be used (specified below). Typically one of the oligonucleotides is the Mosaic End Reverse Compliment (ME-RC, as shown in Example 4); this is the non-transferred strand.

Loading the arms to make the transposome: Arms were loaded in a 1:1 arms:transposase molar ratio; typically 25 µM arms are combined with an equal volume of unloaded transposase (at 0.72 mg/ml, in 53.3% glycerol, 333 mM KCl and 20 mM PIPES, pH7.5). The mixture is incubated at 47° C. for 60 min, during which loading of the arms and assembly of the transposome occurs. After incubation, the transposomes (transposases loaded with respective arms) are at a concentration of 0.36 mg/ml (in 166.7 mM KCl, 26.7% glycerol and 20 mM PIPES, pH7.5). Transposome samples are then diluted with Storage buffer (166.7 mM KCl, 52.9% glycerol, 20 mM PIPES, pH7.5) to 0.18 mg/ml concentration, with final buffer formulation of 166.7 mM KCl, 39.8% glycerol and 20 mM PIPES, pH7.5.

Tagmentation reactions: For each tagmentation reaction, different amounts (specified below) of DNA are combined with 10 µl of 2× reaction buffer (40% glycerol, 30% DMSO, 50 mM Tris Acetate, pH 7.5), 2 µl of 10× manganese chloride (various concentrations) and 4 µl of transposome (various concentrations) to a final volume of 20 µl. Typically, for a large amount of target DNA (e.g. 50 ng) 2 µl of manganese chloride (100 mM) and 4 µl of transposome (0.18 mg/ml) would be used. Typically, for a small amount of target DNA (e.g. 1 ng) 2 µl of manganese chloride (10 mM) and 4 µl of transposome (0.0.2 mg/ml) would be used. The reaction is incubated in a thermocycler with a heated lid (105° C.) at 55° C. for 5 min. Reactions are stopped immediately with the addition of 20 µl stop solution (4.5 M GHCl, 25 mM Tris-HCl, pH8) and incubated for 5 min at room temperature. DNA is purified using different volumes (specified below) of AMPure XP Reagent (Beckman Coulter), and finally eluted in 10 mM Tris-HCl, pH8, according to the manufacturer's instructions. In some cases the tagmented DNA can be separated and visualized on an agarose gel.

Amplification: Different volumes (specified below) of the eluted tagmented DNA is used for amplification. Different PCR kits and conditions can be used (specified below). After amplification the products are purified using different volumes (specified below) of AMPure XP Reagent (Beckman Coulter), and a finally eluted in 10 mM Tris-HCl pH8.

Visualization: Sample can be separated either on and agarose gel, or on an Agilent Bioanalyzer 2100 using a High Sensitivity DNA Chip, or on a Perkin Elmer Labchip GXII Touch HT using a DNA HiSens Chip.

Example 6: The Effect of Manganese Concentration on Tagmentation

The effect of manganese concentration on tagmentation efficiency and fragment length was investigated. TnAa-Tnp-P47K was used to conduct tagmentation experiments using different concentrations of manganese in the reaction. The tagmentation was conducted essentially as described for Example 5, with the following specific conditions:

Arms: ME/R1R2 arms were used. This comprises an equimolar mixture of two types of arms, each is a standard mosaic end (ME) in conjunction with a different sequencing adapter (R1 or R2), as shown below

```
R1:     5'-TCGTCGGCAGCGTCAGATGTGTATAAGAGACAG-OH-3'    (SEQ ID NO: 39)
                         |||||||||||||||||||
ME_RC:                3'-TCTACACATATTCTCTGTC   -5'    (SEQ ID NO: 40)

R2:     5'-GTCTCGTGGGCTCGGAGATGTGTATAAGAGACAG-OH-3'   (SEQ ID NO: 41)
                          |||||||||||||||||||
ME_RC:                 3'-TCTACACATATTCTCTGTC   -5'   (SEQ ID NO: 42)
```

Tagmentation reaction: 1 ng *E. coli* DNA was used as the target. Manganese was varied from 1 mM to 0.0125 mM final concentration, while transpososome was held at 80 ng/reaction. After tagmentation the DNA was purified using 3× volumes of AMPure XP Reagent (Beckman Coulter), and finally eluted in 10 ul 10 mM Tris-HCl, pH8.

Amplification: PCR was performed using R1 and R2 arm-specific primers, 8 ul tagmented DNA and a Kapa Biosystems HiFi PCR kit, according to the manufacturer's instructions. The sample was amplified for 12 cycles. Following amplification, DNA was purified using 3× volumes of AMPure XP Reagent (Beckman Coulter), and finally eluted in 20 µl of 10 mM Tris-HCl, pH8.

Visualization: Undiluted sample was separated on an Agilent Bioanalyzer 2100.

Figure 5:
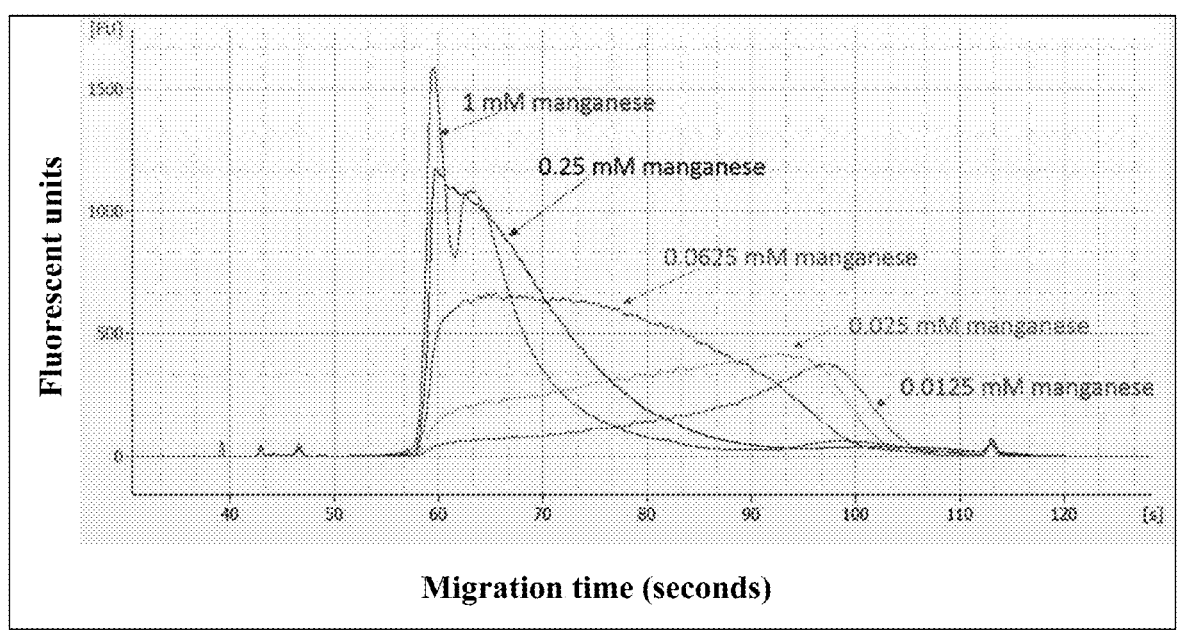
FIG. 5 is graph depicting an Agilent Bioanalyzer trace of fluorescence units plotted against migration time. The trace shows the effect of manganese on the tagmentation efficiency of the TnAa-Tpn-P47K derived transpososome. Increased manganese concentration results in shorter fragments as a consequence of increased tagmentation.

The results are shown in FIG. 5. The use of 3× volumes of AMPure XP Reagent ensures that even small fragments are retained to the end of the process, so the trace reflects the degree to which tagmentation works. Migration time is used as a surrogate for fragment size in this example. Shorter migration times indicate that the fragments are shorter, and that more tagmentation has taken place. The Bioanalyzer trace proves that the P47K mutant transpososome exhibited efficient tagmentation in the presence of 1 mM manganese (FIG. 5; red line), as shown by the production of short fragments. Progressively less manganese resulted in progressively less tagmentation, and larger fragments.

Example 7: The Effect of Transpososome Concentration on Tagmentation

The effect of transpososome concentration on tagmentation efficiency and fragment length was investigated. TnAa-Tnp-P47K was used to conduct tagmentation experiments using different amounts of transpososome in the reaction. The tagmentation was conducted essentially as described for Example 5 and Example 6, with the following specific conditions:

Arms: ME/R1R2 arms were used. This comprises an equimolar mixture of two types of arms, each is a standard mosaic end (ME) in conjunction with a different sequencing adapter (R1 or R2), as shown below.

```
R1:      5'-TCGTCGGCAGCGTCAGATGTGTATAAGAGACAG-OH-3'    (SEQ ID NO: 43)
                             ||||||||||||||||||||
ME_RC:                    3'-TCTACACATATTCTCTGTC    -5'  (SEQ ID NO: 44)

R2:      5'-GTCTCGTGGGCTCGGAGATGTGTATAAGAGACAG-OH-3'   (SEQ ID NO: 45)
                              ||||||||||||||||||||
ME_RC:                     3'-TCTACACATATTCTCTGTC   -5'  (SEQ ID NO: 46)
```

Tagmentation reaction: 1 ng *E. coli* DNA was used as the target. Transpososome was varied from 80 ng to 5 ng/reaction, while manganese was held at 1 mM. After tagmentation the DNA was purified using 3× volumes of AMPure XP Reagent (Beckman Coulter), and finally eluted in 22 ul 10 mM Tris-HCl, pH8.

Amplification: PCR was performed using R1 and R2 arm-specific primers, 20 ul tagmented DNA and a Kapa Biosystems HiFi PCR kit, according to the manufacturer's instructions. The sample was amplified for 12 cycles. Following amplification, DNA was purified using 3× volumes of AMPure XP Reagent (Beckman Coulter), and finally eluted in 30 µl of 10 mM Tris-HCl, pH8.

Visualization: Undiluted sample was separated on an Agilent Bioanalyzer 2100.

Figure 6:
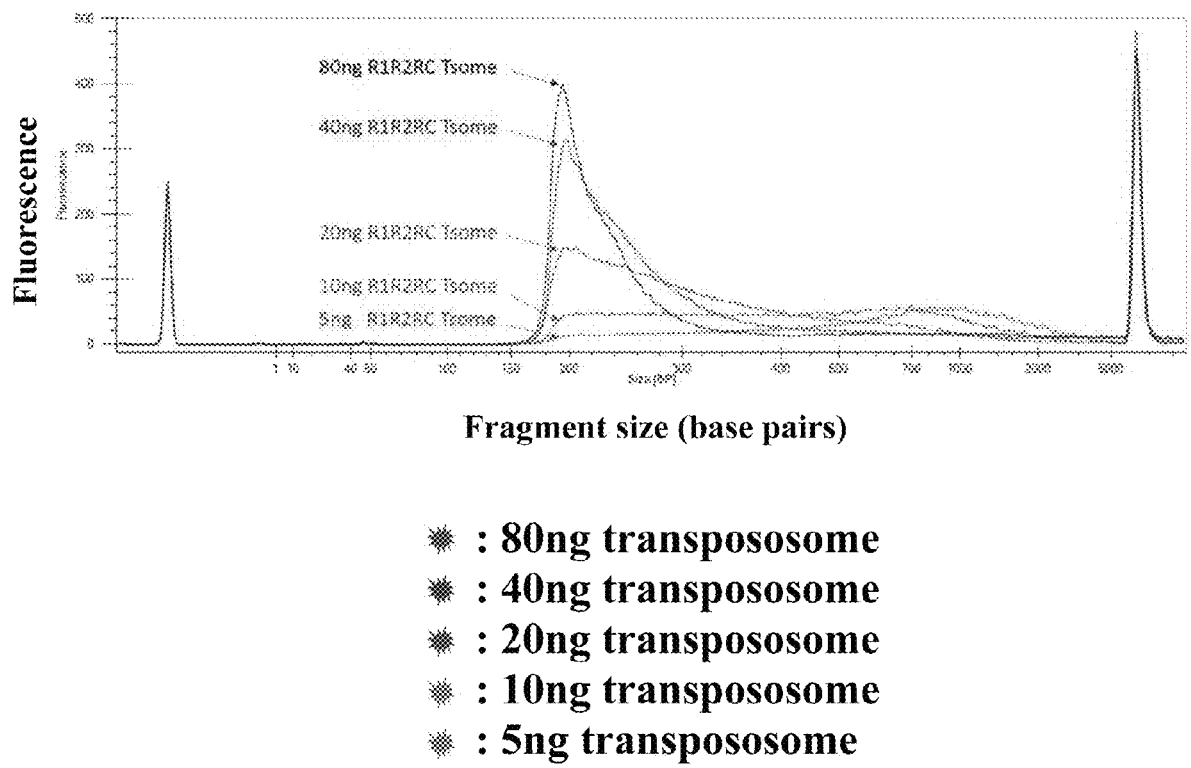
FIG. 6 is graph depicting an Agilent Bioanalyzer trace of fluorescence units plotted against fragment size. The trace shows the effect of transpososome concentration on the tagmentation efficiency of the TnAa-Tpn-P47K derived transpososome. Increased amount of complex results in shorter fragments as a consequence of increased tagmentation.

The results are shown in FIG. 6. The use of 3× volumes of AMPure XP Reagent ensures that even small fragments are retained to the end of the process so the trace reflects the degree to which tagmentation works. Shorter fragments indicate that more tagmentation is taking place. The Bioanalyzer trace proves that, in the presence of 1 mM manganese, the P47K mutant transpososome exhibited efficient tagmentation at high concentrations (such as 80 ng/reaction, FIG. 5; blue line), as shown by the production of short fragments. Progressively less transpososome resulted in progressively less tagmentation, and larger fragments.

Figure 7:
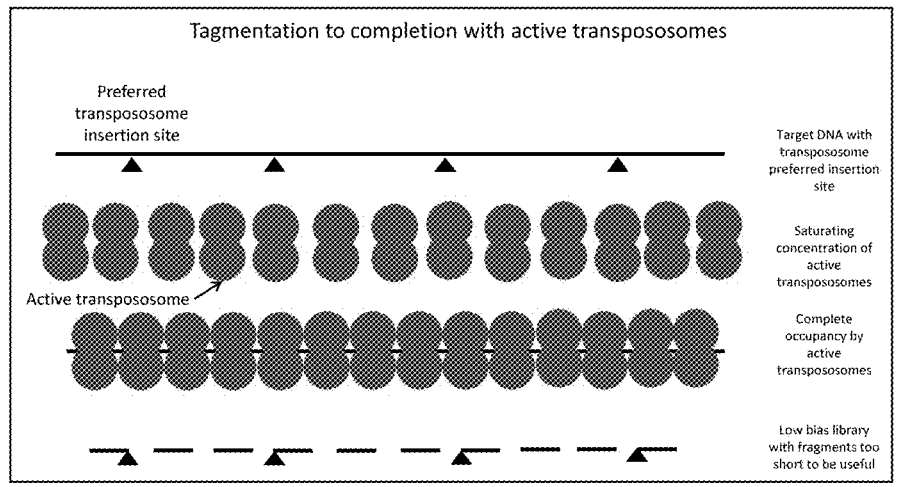
FIGS. 7A-C is a series of schematic diagrams depicting the tagmentation process under different conditions. Panel A depicts the process of tagmentation when it has been performed under conditions that promote transpososome insertion. This may occur with a saturating amount of an efficient (e.g. high manganese concentration) and active transpososome. The final result is a DNA library with low cut-position bias but an average fragment size that is too small to be useful. Panel B depicts the process of tagmentation when it has been performed under conditions that do not promote transpososome insertion. This may occur with a non-saturating amount of an efficient (e.g. high manganese concentration) and active transpososome. It may also occur with a potentially saturating amount of an inefficient (e.g. because of insufficient time or because it is starved of a co-factor such as $Mn^{2+}$) but still active transpososome. In either case, the final result is a DNA library with larger fragment sizes and which exhibits a high insertional bias. Panel C depicts the process of tagmentation when it has been performed under insertion-promoting conditions, with saturating amounts of a mixture of active and inactive (able to bind but not insert) transpososome. In this case the target DNA is fully occupied with transpososomes but is only cleaved (tagmented) at sites where an active transpososome encounters the target DNA. The active and inactive transpososomes compete for the preferred insertion sites.
Figure 7:
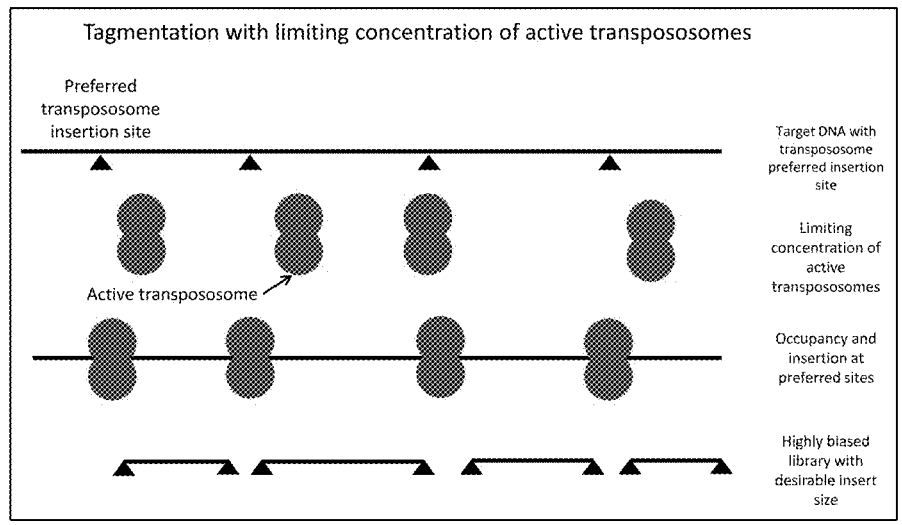
Figure 7:
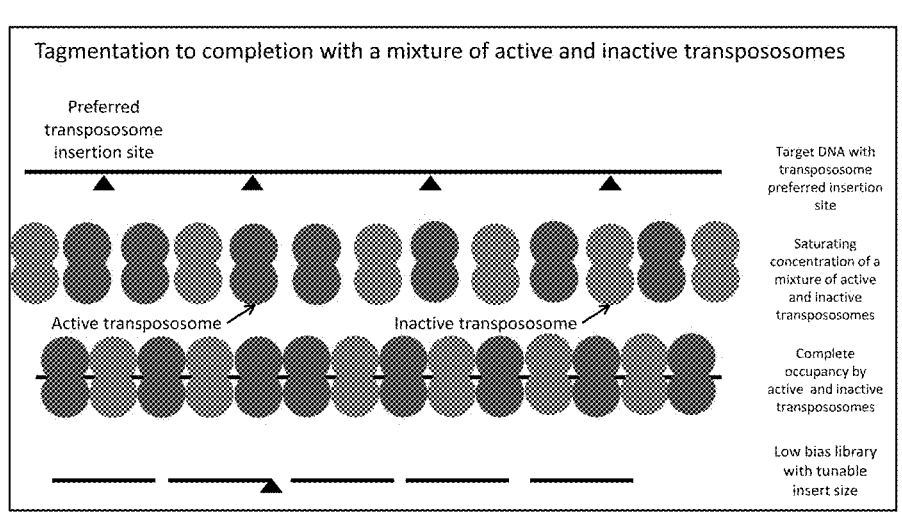

Example 8: Fragmentation Characteristics, Target Saturation, and the Concept of Transpososome Competitor Control The results of the manganese and transpososome assays can be interpreted as follows: It is clear that both transpososome levels and manganese levels affect the activity (defined as the number of cuts in a target DNA divided by the mass of the target DNA) of the transpososome. Reducing the transpososome to target DNA target ratio caused the size to increase. Similarly, starving the reaction of a co-factor (e.g., manganese) resulted in an increase in fragment size (FIG. 7A). If an excess of transpososome is present, and the reaction is not otherwise limited, short fragments with insertion sites separated by about 40 base pairs are created. It should be noted that the peak numbers at approximately 200 bp fragment size shown in FIG. 6 (and the equivalent peak at 60 sec migration time in FIG. 5) represent a 40 bp insertion site separation because the fragments include the ES and adaptor sequences.

There appeared to be an absolute limit beyond which smaller fragments could not be made. This implies that if excess manganese and transpososome is added, every area of the target DNA is bound and eventually cut, and the 40 bp minimum between insertion sites is due to steric limitations (FIG. 7A).

In contrast, if the transpososome or manganese (or possibly other essential factors) is limiting, then the complex will tend to bind and cut first at the transpososomes' preferred sites. The transpososome remains bound at the insertion site after cutting, so it is unable to escape and cut at other, less-preferred sites (FIG. 7B). Only further addition of transpososomes will result in those additional complexes binding and cutting at less preferred sites on the target DNA.

If this is the case then insertion bias should be lower when the DNA is saturated with transpososome, as eventually less-preferred sites are cut, not just the preferred ones. Preferred binding sites will be selected at the level of the preference within the remaining "parking space" left open for the transposase. In contrast, the insertion bias should be high when the transpososome is limited in some fashion, e.g. by co-factor starvation or low transpososome concentration, because the preferred sites are used first, and the less preferred escape cutting because there is insufficient transpososome.

It follows that if a mixture of an active transpososome (able to bind, cut and insert at the target site), and an inactive transpososome (able to bind, but not cut or insert at the target site) was contacted with target DNA then the active and inactive complexes would compete for each potential binding site, and the ratio of the active and inactive complexes would affect both the fragment size and the insertion bias (FIG. 7C).

Example 9: Compositions Comprising Active and Inactive Transpososomes

Inactive transpososomes of the disclosure bind the target DNA with the same efficiency and bias as an active transpososome, however, the inactive transpososome does not cut the target DNA to any extent or at any site (not even a nick of the DNA). In contrast, active transpososomes of the disclosure bind the target DNA and cut the target DNA at every site to which it binds.

Compositions of the disclosure may comprise both an inactive and an active transpososome. When these compositions are loaded onto the DNA target at, for example, a saturating concentration, the target DNA is cut only where the active transpososome binds the target DNA. By varying the ratio of the active to inactive transpososomes within the composition, the desired fragment size will be determined by the ratio and the amount of target DNA becomes irrelevant (FIG. 7C).

By varying the ratio of active to inactive transposase, the fragment size may be controlled without knowledge of the amount of target DNA used. Moreover, by using competitive inhibition, the cut-position bias (also referred to herein as the insertion bias) is low, because all sites have an equal chance of being cut, as all sites are loaded with a transpososome (either an active or inactive transpososome).

Example 10: Inactive Transpososomes Containing Modified DNA Adapters/Arms

When using modified arms to produce inactive transpososomes, it is possible to achieve the desired ratio of active to inactive transpososome using different methods. Nonlimiting examples are provided below.

Mixing loaded transpososomes: Methods employing this strategy include the following steps: loading a preparation of transposase with standard arms (transferred strand is 3'-OH) producing active transpososomes; loading a preparation of transposase with modified arms (transferred strand is not 3'-OH, with the 3'-group being one to inhibit strand transfer e.g. 3'-phosphate or 3'-H such as would be obtained if a 3'-dideoxy-nucleotide was used at the 3'-end, etc.) producing inactive transpososomes; and mixing the active and inactive transpososomes in a desired ratio (e.g. 1:3), resulting in a composition comprising active and inactive transpososomes. Use of this composition for fragmentation of target DNA results in improved library characteristics compared to use of a composition containing active transpososomes alone.

Mixing adapters and transposases: Methods employing this strategy include the following steps: prepare a mixture of standard arms (transferred strand is 3'-OH) and modified arms (transferred strand is not 3'-OH, with the 3'-group being one to inhibit strand transfer e.g. 3'-phosphate or 3'-H such as would be obtained if a 3'-dideoxy-nucleotide was used at the 3'-end, etc.) in a desired ratio such as 1:3 and load the transposase with the above mixture of arms resulting in the production of a composition comprising active and inactive transpososomes. Use of this composition for fragmentation of target DNA results in improved library characteristics compared to use of a composition containing active transposase alone.

Modified adapters: Modified arms of the inactive transpososomes of the disclosure may comprise a 3'-end that is blocked to prevent strand transfer, and, therefore, to prevent cutting of the target DNA. The 3'-OH supplies the electrons required for a nucleophilic attack during strand exchange. Preferably, modified arms of the disclosure contain a dideoxy-nucleotide at the 3'-end (3'-OH is replaced by 3'-H), or contain a 3'-phosphorylated-nucleotide at the 3'-end (3'-OH is replaced by 3'-phosphate).

To test the modification approach a transpososome with mosaic end arms that included either a 3'-3 carbon spacer (phosphoramidite) or a 3'-phosphate at the terminal nucleotide of the transferred strand of the arm was contacted with target DNA (an unmodified end arm would contain the natural 3' hydroxyl group).

Modified adapters are illustrated below:

Mosaic end arms (unmodified) "MERC", comprising oligonucleotides ME_MR and ME_RC:

```
ME_MR:  5'-AGATGTGTATAAGAGACAG-OH-3' (SEQ ID NO: 47)
           ||||||||||||||||||
ME_RC:  3'-TCTACACATATTCTCTGTC   -5' (SEQ ID NO: 48)
```

R1 arms "R1RC", comprising oligonucleotides R1 and ME_RC:

```
R1:     5'-TCGTCGGCAGCGTCAGATGTGTATAAGAGACAG-OH-3' (SEQ ID NO: 49)
                          ||||||||||||||||||
ME_RC:                 3'-TCTACACATATTCTCTGTC   -5' (SEQ ID NO: 50)
```

R2 arms "R2RC", comprising oligonucleotides R2 and ME_RC:

```
R2:     5'-GTCTCGTGGGCTCGGAGATGTGTATAAGAGACAG-OH-3' (SEQ ID NO: 51)
                          ||||||||||||||||||
ME_RC:                 3'-TCTACACATATTCTCTGTC   -5' (SEQ ID NO: 52)
```

3'-Phosphate Mosaic end arms "3PRC", comprising oligonucleotides 3P and ME_RC:

```
3P:     5'-AGATGTGTATAAGAGACAG-Phos-3' (SEQ ID NO: 53)
           ||||||||||||||||||
ME_RC:  3'-TCTACACATATTCTCTGTC   -5' (SEQ ID NO: 54)
```

3'-Spacer mosaic end arms "3CRC", comprising oligonucleotides 3C and ME_RC:

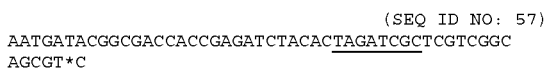

Amplification primers (Sample index included):
i501 (or generic i5xx—denoting different sample indexing primers)

(SEQ ID NO: 57)
AATGATACGGCGACCACCGAGATCTACAC<u>TAGATCGCT</u>CGTCGGC
AGCGT*C i701 (or generic i7xx—denoting different sample indexing primers)

(SEQ ID NO: 58)
CAAGCAGAAGACGGCATACGAGAT<u>TCGCCTTA</u>GTCTCGTGGGCTCG*G

For SEQ ID NOs: 57 and 58, the (*) represents a phosphorothioate bond.

The tagmentation was conducted essentially as described for Example 5, with the following specific conditions:

Arm preparation: Unmodified ME_RC, ME_MR, R1, R2, and modified 3P and 3C oligonucleotides were obtained from IDT. Each oligonucleotide was resuspended in 20 mM PIPES pH7.5 to 100 μM. ME_MR, R1, R2, 3P and 3C oligos were individually duplexed with the ME_RC oligo as described in Example 5. The duplexed products formed 50 μM of the MERC, R1RC, R2RC, 3PRC and 3CRC arms respectively, and were each diluted to 25 μM with 20 mM PIPES pH7.5.

Loading the arms to make the transpososome: MERC, 3PRC and 3CRC (25 μM) arms were individually combined with unloaded TnAa transposase-P47K in a 1:1 molar ratio. The R1RC and R2RC arms were combined with unloaded TnAa transposase-P47K in a 1:1:2 ratio. Assembly of the transpososome was completed as described in Example 5.

Tagmentation reactions: For each tagmentation reaction, 200 ng of Affymetrix E. coli genomic DNA (4 μl of 50 ng/μl DNA) was used. 2 μl of 10× manganese chloride (100 mM), with 4 μl of MERC-loaded transposase or R1R2RC-loaded transposase or 3PRC-loaded transposase or 3CRC-loaded transposase (0.18 mg/ml) respectively was used in each reaction. After tagmentation, DNA was purified using 3× volumes (120 μl) of AMPure XP Reagent (Beckman Coulter), and finally eluted in 12 μl of 10 mM Tris-HCl, pH8, according to the manufacturer's instructions.

Visualization: 10 μl of the eluate was combined with 6 μl of loading dye, and 1 μl of each mix was loaded into alternate lanes on a 1% agarose gel, for fragment separation. No amplification step was conducted.

Figure 8:
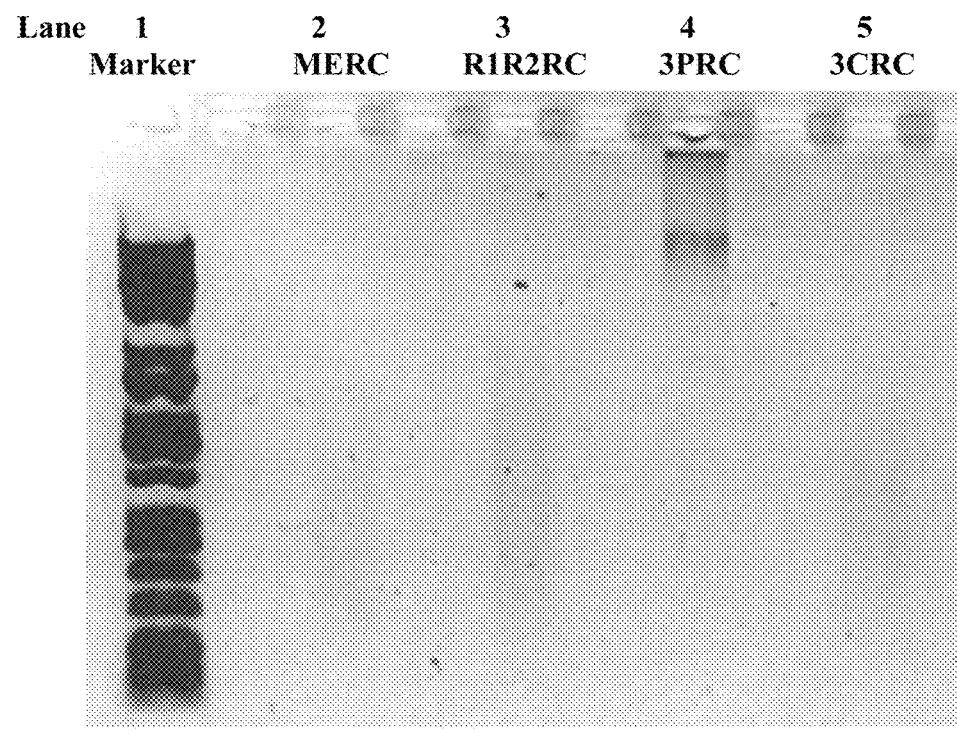
FIG. 8 is a photograph of a gel showing the result of an experiment involving tagmentation followed by gel electrophoresis, which demonstrates that 3'-phophorylated arms produce inactive transpososomes. Equal molar quantities of transposase (TnAa-Tnp-P47K) loaded with standard mosaic arms (MERC, lane 2), R1/R2 arms (R1R2RC, lane 3), 3'-phosphate modified mosaic arms (3PRC, lane 4) or 3'-spacer modified mosaic arms (3CRC, lane 5) were used to tagment 200 ng of E. coli genomic DNA. Following purification by GHCl treatment and AMPure XP Reagent (Beckman Coulter) purification, the DNA was resolved on a 1% agarose gel. Only the transposase loaded with 3'-phosphate-modified arms failed to tagment genomic DNA.

The results are shown in FIG. 8. Gel electrophoresis showed that only in the case of the transpososome loaded with the 3PRC (3'-phosphate) arms was the DNA largely intact (FIG. 8, lane 4). This demonstrates that while the MERC, R1R2RC and 3CRC loaded transpososomes successfully tagmented genomic DNA (FIG. 8, lanes 2, 3 and 5 respectively), the 3PRC loaded transpososome did not cause extensive shearing of the DNA. It is interesting to note that the 3'-spacer modified arms were active and resulted in tagmentation of DNA, possibly because a hydroxyl group is still present.

Example 11: Modulation of Fragment Size by the Addition of Transpososome Loaded with 3'-Phosphate Modified Mosaic End Arms to Reactions The in the following example the DNA purification steps allow short fragments to be isolated and amplified. This to investigate the insertion profile of the transpososome mixtures and is not typical of a method used to generate a useful sequencing library Transpososome preparation: Arms and transpososomes were prepared as described for Example 10. R1R2RC-loaded transpososome (active transpososome) and 3PRC-loaded transpososome (inactive transpososome) were each further diluted from 0.18 mg/ml to 0.08 mg/ml (or 80 ng/μl) and 0.04 mg/ml (40 ng/μl) with dilution buffer (166.7 mM KCl, 39.8% glycerol and 20 mM PIPES, pH7.5).

Tagmentation reactions: Tagmentation reactions were essentially as described in Example 5, with the following specific conditions: For each tagmentation reaction, 1 ng of E. coli genomic DNA (4 μl of 0.25 ng/μl DNA) was combined with 10 μl of 2× reaction buffer and 2 μl of 10× manganese chloride (10 mM). The transpososome included was either: a) 2 μl of R1R2RC-loaded transpososome (80 ng/μl) and 2 μl dilution buffer, for a total of 160 ng of active transpososome, with no inactive transpososome included; b) 2 μl of R1R2RC-loaded transpososome (80 ng/μl) and 2 μl of 3PRC-loaded transpososome (40 ng/μl), for a 2:1 active: inactive transpososome ratio, and; c) 2 μl of R1R2RC-loaded transpososome (80 ng/μl) and 2 μl of 3PRC-loaded transpososome (80 ng/μl), for a 1:1 active:inactive enzyme transpososome ratio.

A separate, additional set of tagmentation reactions were assembled, essentially as just described, except with half the amounts of transpososome used. After the reaction was stopped, DNA was purified using 3× volumes (120 μl) of AMPure XP Reagent (Beckman Coulter), and finally eluted in 22 μl of 10 mM Tris-HCl, pH 8.

Amplification: 20 μl of the eluted tagmented DNA was amplified using a Kapa Biosytems HiFi PCR kit, according to instructions. 5 μl of 2.5 μM i5xx index primer and 5 μl of 2.5 μM i7xx index primer was included in each 5 μl reaction. 12 cycles of PCR amplification (72° C. 3 min, 98° C. 30 s, 12× (98° C. 15 s, 62° C. 30 s, 72° C. 3 min), 4° C. hold) were conducted. Amplified products were was purified using 3× volumes (150 μl) of AMPure XP Reagent (Beckman Coulter), and a final elution in 30 μl of 10 mM Tris-HCl pH8. 15 μl of the eluted product was analyzed on a LabChip GXII (Perkin Elmer).

Figure 9:
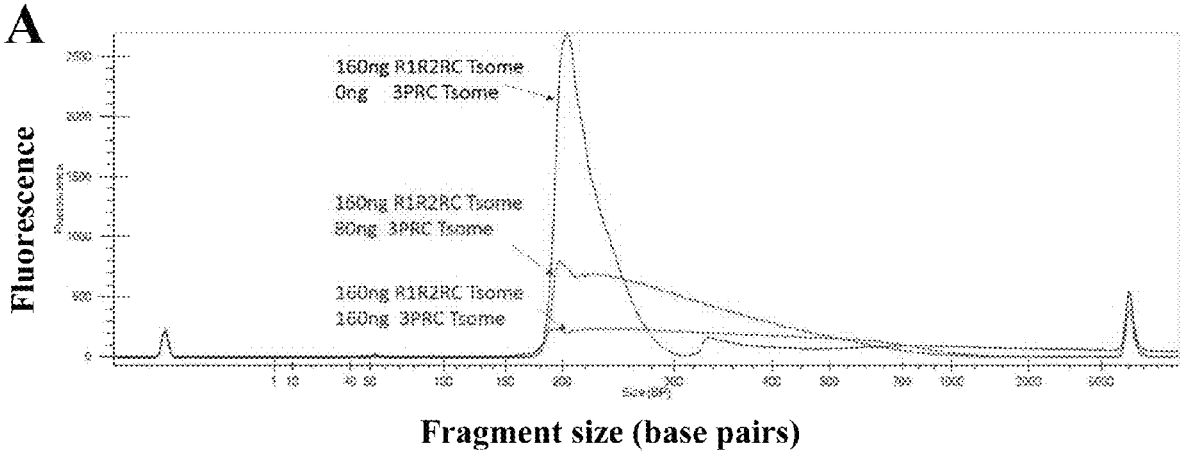
FIG. 9A-B is a pair of graphs showing the fragment size distribution from a tagmentation and amplification experiment, as a plot from a LabChip GXII (Perkin Elmer) using a DNA HiSensitivity chip. The plot demonstrates that the addition of inactive transpososomes to saturating quantities of active transpososomes decreases the proportion of completely tagmented fragments and increases library insert size. (A) Tagmentation with 160 ng of active transpososome, followed by purification post tagmentation, and post amplification with 3x volumes of AMPure XP Reagent (Beckman Coulter), yields a library with a narrow size distribution of completely tagmented fragments of between 180 to 300 bp (blue), the small peak between 300-400 bp is a LabChip artefact due to high concentration of the library. Adding 80 ng of inactive transpososomes (2:1 active:inactive) decreased the proportion of completely tagmented small fragments (red), and adding 160 ng of inactive transpososomes (1:1 active:inactive) further decreased the proportion of completely tagmented small fragments (brown). (B) Shows the same result as (A), except in this case half the amount of transpososome was used.
Figure 9:
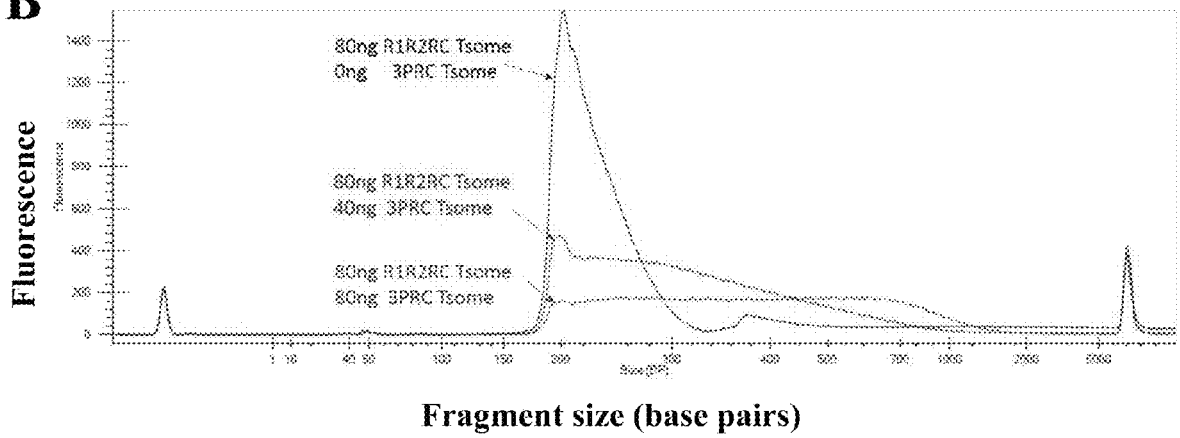

The results are shown in FIG. 9. In these examples it can be seen that addition of inactive transpososomes to saturating quantities of active transpososomes, decreases the proportion of completely tagmented library fragments. Addition of equal additional quantities of active but unloaded transposase did not produce this effect.

Example 12: Modulation of Sequencing Library Fragment Size by the Addition of Transpososome Loaded with 3'-Phosphate Modified Mosaic End Arms to Tagmentation Reactions In the following example the DNA purification steps removes short fragments after tagmentation and promotes isolation and amplification of useful longer fragments. This is typical of a method used to generate a useful sequencing library.

Transpososome preparation: Arms and transpososomes were prepared as described for Example 11.

Tagmentation reactions: Tagmentation reactions were essentially as described in Example 11, with the following specific conditions: 4 reactions were assembled, these all contained 160 ng of inactive transpososome complex and either 0 ng, 80 ng, 160 ng or 360 ng of inactive transpososome. After tagmentation, DNA was purified using 1× volume (40 µl) of AMPure XP Reagent (Beckman Coulter) and finally eluted in 22 µl of 10 mM Tris-HCl, pH8

Amplification: Amplification was as for Example 11, however in this case amplified products were purified using 0.8× volumes (40 µl) of AMPure XP Reagent (Beckman Coulter), and finally eluted in 12 µl of 10 mM Tris-HCl pH8.

2 µl of the reaction was diluted 5 times to 10 µl with 10 mM Tris-HCl pH8 for fragment analysis on a LabChip GXII (Perkin Elmer) using a DNA HiSensitivity chip.

Figure 10:
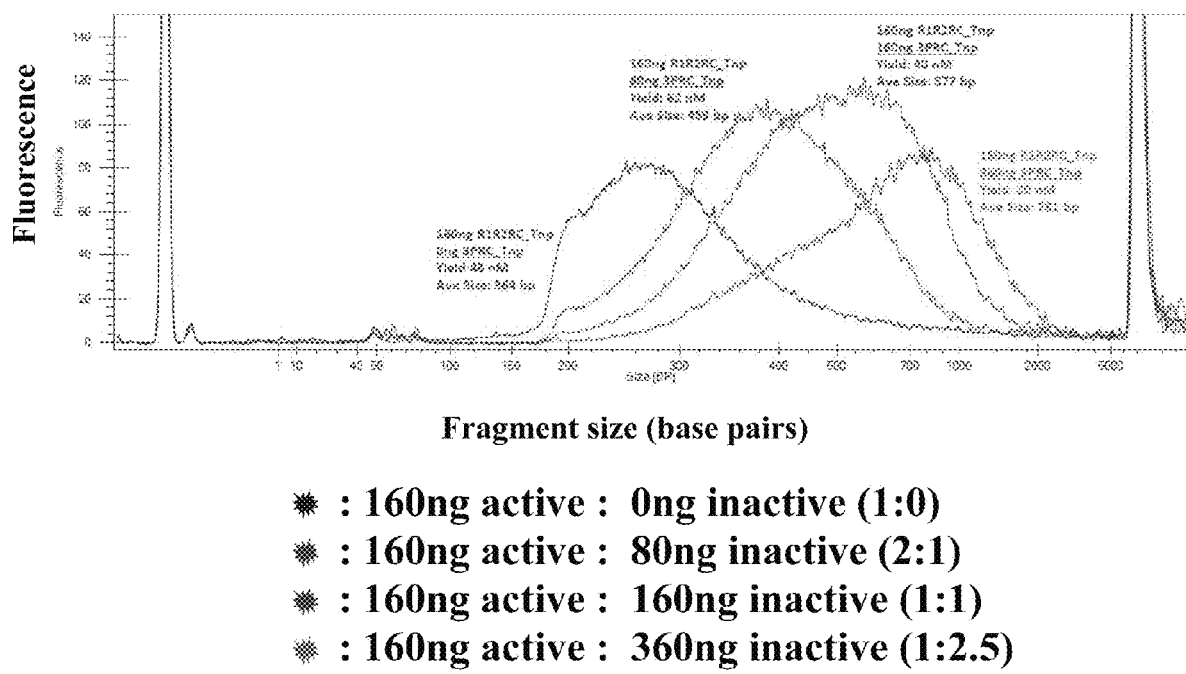
FIG. 10 is a graph showing the fragment size distribution from a tagmentation sequencing library preparation experiment, as a plot from a LabChip GXII (Perkin Elmer) using a DNA HiSensitivity chip. The plot demonstrates that the addition of inactive transpososome increased the average fragment size in a dose-response manner. 160 ng of active transpososome was combined with 0 ng, 80 ng, 160 ng or 360 ng of inactive transpososome, and used to tagment 1 ng of E. coli genomic DNA. Purification steps used 1x volume of AMPure XP Reagent (Beckman Coulter), which is typically used to generate useful sequencing libraries. Library yields shown have been adjusted for the 5 times dilution prior to loading the LabChip. Average fragment sizes were: 364 bp, 459 bp, 577 bp, and 761 bp for reactions that contained 0 ng, 80 ng, 160 ng or 360 ng of inactive transpososome, respectively.

The results are shown in FIG. 10. It can be seen that, while holding the amount of active transpososome constant at 160 ng, the addition of inactive transpososome from 0 ng, 80 ng, 160 ng and 360 ng, increased the average fragment size in a dose-response manner. Average fragment sizes were: 364 bp, 459 bp, 577 bp, and 761 bp, respectively. Library yields were: 48 nM, 62 nM, 40 nM, and 20 nM respectively.

Example 13: Sequencing of Libraries Created with a Mixture of Active and Inactive Transpososomes While addition of inactive transpososomes to saturating quantities of active transpososomes resulted in increased library insert sizes and reduced the degree of tagmentation, it was necessary to determine the effect of these perturbations on the characteristics of the resulting sequencing libraries.

Whole genome sequencing libraries were constructed from 1 ng E. coli genomic DNA (ATCC, MG1655) and sequenced on an Illumina MiSeq instrument using v3 2×150 chemistry. Enzyme preparation and amplification procedures were performed essentially as described above, in Example 12, with specific conditions described below. Each library was tagmented in duplicate, and amplified with unique index pairs. For example, with 2 replicate tagmentation reactions, one is indexed with i501 and i701, while the other is indexed with i502 and i701 during PCR amplification.

Part 1: Tagmentation reactions with 3 concentrations of manganese chloride (10 mM, 1 mM and 0.025 mM final reaction concentration), and 80 ng of active transpososomes were used to demonstrate the effect of manganese on sequencing metrics, without inactive transpososomes present in the reaction.

Part 2: Tagmentation reactions with 1 mM manganese final reaction concentration and different ratios of active: inactive transpososomes were used to demonstrate the effect of the inactive transpososomes on sequencing metrics. Active:inactive transpososome ratios were as follows: (a) 2:1, 160 ng active: 80 ng inactive; (b) 1:1 160 ng active: 160 ng inactive; (c) 1:2.25, 160 ng active: 360 ng inactive, and; (d) 160 ng active: 0 ng inactive competitor-free control.

Part 3: Comparative libraries were constructed with the Illumina Nextera XT kit, and also the KAPA HyperPlus kit using the standard protocols (according to the manufacturer's instructions) for 1 ng DNA input and duplexed TruSeq adapters.

Following alignment to the reference genome, sequencing data was analyzed. Library insert sizes were calculated based on read mapping locations (shown in FIG. 11). Start site bias was estimated by calculating the cumulative nucleotide base variance at positions flanking the read start site (shown in FIG. 12A). Start site bias is also shown in terms of nucleotide base frequency at each position (FIG. 12B). Increased start site preference (bias) manifests as increased nucleotide base variance around the insertion site and the increased frequency of certain nucleotides above the baseline nucleotide frequency of the genome.

The results of these experiments are as follows: The decrease in manganese again resulted in larger fragments and increased insertional bias.

Figure 11:
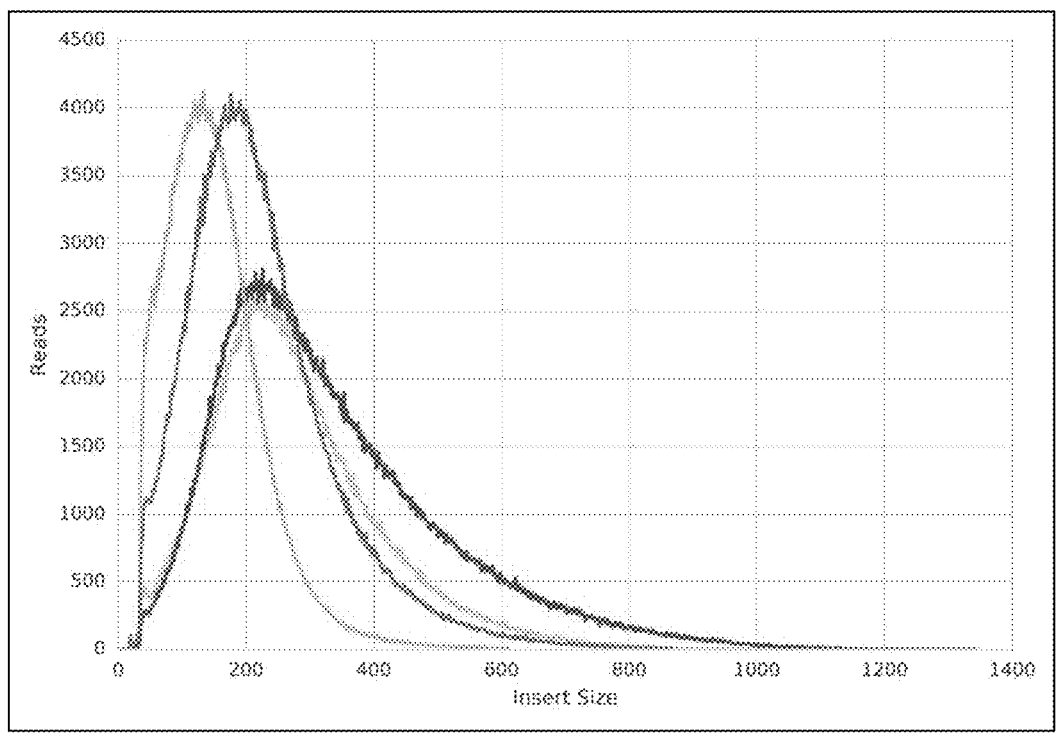
FIG. 11 is a graph demonstrating increasing insert size by tagmenting in the presence of inactive transpososomes. Libraries were constructed from 1 ng of E. coli genomic DNA by tagmentation with TnAa transposase P47K loaded with unmodified arms (to create active transpososomes) only (purple) or by tagmentation with a mixture of TnAa transposase loaded with active arms and increasing amounts of TnAa transposase loaded with 3'-phosphorylated arms (to create inactive transpososomes), resulting in ratios of active to inactive transpososomes of 2:1 (Lilac), 1:1 (green) and 1:2.25 (red). Following alignment to the reference genome, library insert sizes were calculated based on read mapping locations. Increasing the amount of inactive transpososomes in the presence of saturating amounts of active transpososomes increases the library insert size.
Figure 12A:
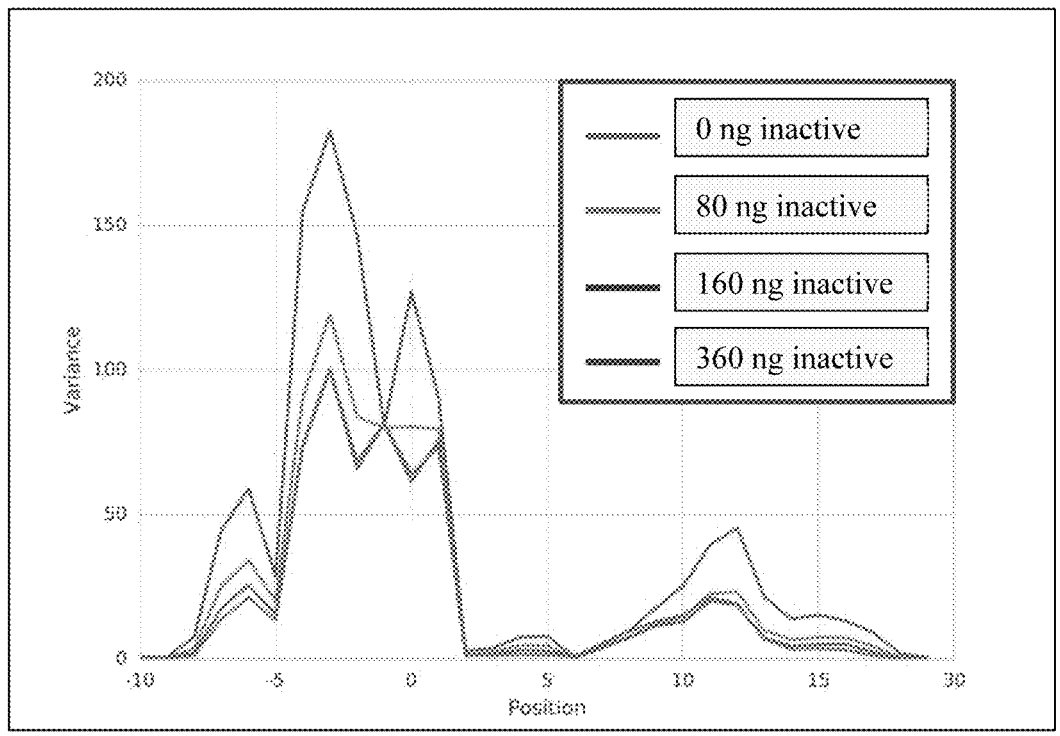
FIG. 12A is a graph demonstrating decreasing insertion bias by tagmenting in the presence of inactive transpososomes. Libraries were constructed from 1 nanogram of E. coli genomic DNA by tagmentation with TnAa transposase P47K loaded with unmodified arms (to create active transpososomes) arms or by tagmentation with a mixture of TnAa transposase P47K loaded with active arms and increasing amounts of TnAa transposase P47K loaded with 3'-phosphorylated arms (inactive transpososomes). Position 0 depicts the insertion site in the genome while negative and positive positions represent genomic areas 5' and 3' relative to the insertion site.
Figure 12B:
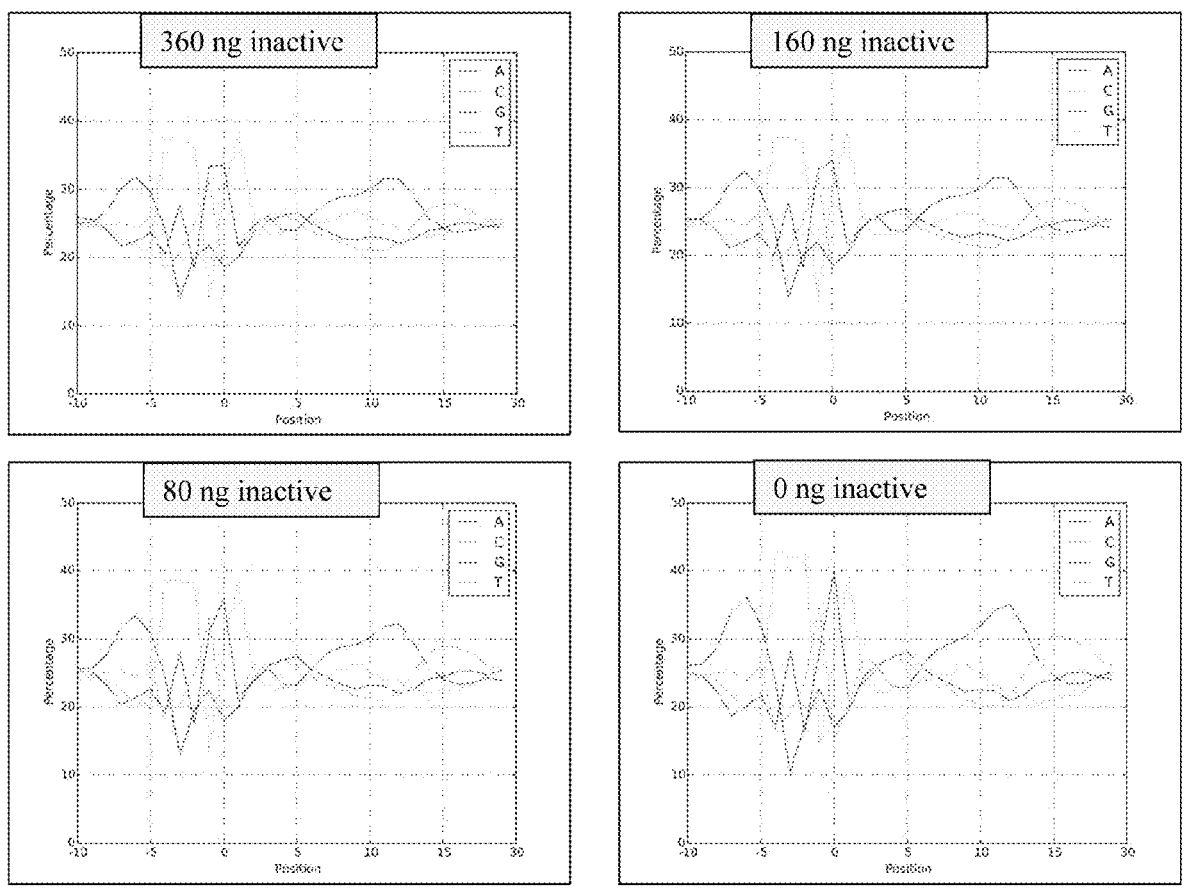
FIG. 12B is a series of four graphs demonstrating decreasing insertion bias by tagmenting in the presence of inactive transpososomes. Libraries were constructed from 1 nanogram of E. coli genomic DNA by tagmentation with TnAa transposase P47K loaded with unmodified arms (to create active transpososomes) arms or by tagmentation with a mixture of TnAa transposase P47K loaded with active arms and increasing amounts of TnAa transposase P47K loaded with 3'-phosphorylated arms (inactive transpososomes). Position 0 depicts the insertion site in the genome while negative and positive positions represent genomic areas 5' and 3' relative to the insertion site.

The addition of inactive transpososomes to the tagmentation reaction to create Illumina compatible libraries results in larger sequenced insert size (FIG. 11). Furthermore, an improved start site bias is also obtained with the addition of inactive transpososomes (FIG. 12). In FIG. 12A, the higher the cumulative variance in nucleotide base variance, the more specific (and biased) is the average insert site in the library. Libraries with low cumulative insertion site variance generally have higher complexity and more even coverage, factors that are beneficial to NGS library preparation. In FIG. 12B, it can be seen that the base frequency at each position is narrower and tends towards 25% (no bias) as the amount of inactive transpososome is added. Due to deep sampling (500,000 reads or more per library/treatment), in a completely unbiased system, the base frequency of each of the four nucleotide bases around the insertion site would equal the average base frequency in the E. coli genome.

It is clear from this work that mosaic end arms ("3PRC" as depicted above), in which the transferred strand is 3'-phosphorylated, can be combined with TnAa-Tpn P47K transposase to produce inactive transpososomes. When used in combination with active transpososomes in total saturating amounts to produce NGS libraries (including Illumina-compatible NGS libraries), the presence of inactive transpososomes results in an increase in insert size, accompanied by a decrease in insertional specificity (both desirable characteristics of a transposase-based NGS library prep system).

Example 14: Modulation of Sequencing Library Fragment Size and Insertion Site Bias by the Addition of Transpososome Loaded with Other Types of Modified Arms to Tagmentation Reactions The examples so far provided have demonstrated the efficacy and utility of the method of controlling fragment size and insertion bias. The examples provided have shown that inactive transpososomes may be created using arms with 3'-phosphate on the transferred strand. Other types of modified arms could be utilized in a similar role. The modified arms used permit the transposase from recognizing and loading the modified arms (and thus form an inactive transpososome) but prevent the inactive transpososome from inserting the arms into target DNA or even cause nicking of the target DNA template.

To demonstrate this, methods similar to, but not necessarily identical to, those described in Examples 5, 6, 7, 8, 9, 10, 11, and 12 are used. Briefly, oligonucleotides are used to create the modified arms and these are loaded to make an inactive transpososome. Tagmentation reactions are then conducted on a DNA target of choice, using different ratios of active and inactive transpososomes. The reactions are used to create sequencing libraries and these libraries are sequenced. Sequence data is then analyzed and the insertion bias and fragment length is determined.

The alternatively modified arms may also be used to create inactive transpososomes and that these have utility in determining fragment size and insertion bias.

Example 15: Modulation of Sequencing Library Fragment Size and Insertion Site Bias by the Addition of Transpososome Formed from Mutant Transposase to Tagmentation Reactions The examples so far provided have demonstrated the efficacy and utility of the method of controlling fragment size and insertion bias. The examples provided have shown that inactive transpososomes may be created using arms with 3'-phosphate on the transferred strand. Inactive transpososomes may also be created by using mutated transposase, and these mutant versions could be used to modulate the functioning of the active transpososomes as disclosed.

To demonstrate this, mutant versions of the transposase gene are created. Mutations include, but are not limited to, modifications of the catalytic triad. Both mutant and wild type transposase are cloned, expressed and purified. The mutant and wild type versions of the transposase are then used to make inactive and active transpososomes, respectively, and these are then incorporated in the disclosed invention.

For the tagmentation and library making, methods similar to, but not necessarily identical to, those described in Examples 5, 6, 7, 8, 9, 10, 11, and 12 are used. Briefly, arms are created and loaded onto the wild type and mutant tranposases to make either active or inactive transpososomes. Tagmentation reactions are then conducted on a DNA target of choice, using different ratios of active and inactive transpososome. The reactions are used to create sequencing libraries and these libraries are sequenced. Sequence data is then analyzed and the insertion bias and fragment length is determined.

Mutant transposases may also be used to create inactive transpososomes and that these have utility in determining fragment size and insertion bias.

Example 16: Modulation of Sequencing Library Fragment Size and Insertion Site Bias by Applying Active and Inactive Transpososomes at Different Times The examples so far provided have demonstrated the efficacy and utility of the method of controlling fragment size and insertion bias. The examples provided have utilized active and inactive transpososomes, which are applied to the target DNA as a mixture. The fragment size and insertion bias could also be manipulated by applying them separately. For example, specific amounts of inactive transpososome could be applied to the target to block preferred insertion sites prior to the application of the active transpososome.

To demonstrate this, methods similar to, but not necessarily identical to, those described in Examples 5, 6, 7, 8, 9, 10, 11, and 12 are used. Briefly, arms are made (from either modified or unmodified oligonucleotides) and are loaded onto the transposases (either wild type or mutant) to make either active or inactive transpososomes. Various amounts of active and inactive transpososome complex are then brought into contact with the DNA target of choice, at different times, for various times, in various orders. The reactions are used to create sequencing libraries and these libraries are sequenced. Sequence data is then analyzed and the insertion bias and fragment length is determined.

Applying the active and inactive transpososomes to the target DNA in ways other than as a mixture has utility in tagmentation reactions and this may be used to control fragment size and insertion bias.

Example 17: Modulation of Sequencing Library Fragment Size and Insertion Site Bias by Mixtures of Active and Inactive Transpososomes from Other Transposons and Insertion Elements The examples so far provided have demonstrated the efficacy and utility of the method of controlling fragment size and insertion bias. The examples provided have utilized a transposase derived from TnAa. Transpososomes (made to be active and inactive as disclosed) created from transposases from other sources could also be utilized for tagmentation and the control thereof by the method as disclosed here.

To demonstrate this, the active and inactive transpososomes (created using principles previously disclosed here) are created from Tn5 transposase, or other transposases from the IS4 family of insertion sequences, or other transposases that work by a "cut and paste" mechanism. These transposases are then incorporated in the disclosed invention.

For the tagmentation and library making, methods similar to, but not necessarily identical to, those described in Examples 5, 6, 7, 8, 9, 10, 11, and 12 are used. Briefly, arms are made (from either modified or unmodified oligonucleotides) and are loaded onto the transposases (either wild type or mutant) to make either active or inactive transpososomes. Tagmentation reactions are then conducted on a DNA target of choice, using different ratios of active and inactive transpososome. The reactions are used to create sequencing libraries and these libraries are sequenced. Sequence data is then analyzed and the insertion bias and fragment length is determined.

The different transposases (and mutant versions) may also be used to create active and inactive transpososomes and that these have utility in tagmentation reactions and that mixtures may be used to control fragment size and insertion bias.

Example 18: Use of Method for Making Sequencing Libraries from Various Target DNA Types The examples so far provided have demonstrated the efficacy and utility of the method of controlling fragment size and insertion bias. The examples provided have utilized E. coli DNA as a target. The methods described here may also be applied to more complex and commercially relevant targets. It may also be applied to DNA targets that vary in the degree of repeats present, or which are G/C-rich or A/T-rich, or which have other modifications.

To demonstrate this, the method is applied to a variety of genomic DNA or cDNA targets. These include, but are not limited to: human, mammalian, animal, plant, protist, fungal, archaebacterial and eubacterial DNA or cDNA samples.

For the tagmentation and library making, methods similar to, but not necessarily identical to, those described in Examples 5, 6, 7, 8, 9, 10, 11, and 12 are used. Briefly, arms are made and are loaded onto the transposases to make either active or inactive transpososomes. Tagmentation reactions are then conducted on a DNA comprising either human, mammalian, animal, plant, protist, fungal, archaebacterial or eubacterial DNA or cDNA, using different ratios of active and inactive transpososome. The reactions are used to create sequencing libraries and these libraries are sequenced. Sequence data is then analyzed and the insertion bias and fragment length is determined.

Methods of the disclosure may be used with different types of DNA targets.

Example 19: Utilizing Dissimilar Transposases and Other DNA-Binding Proteins

The examples so far provided have demonstrated the efficacy and utility of the method of controlling fragment size and insertion bias. The examples provided have utilized transposases derived from the same transposon to create both the active and inactive transpososomes. The transposases of the active and inactive transpososomes need not be derived from the same source, and, in fact, distantly related or dissimilar transposases may be used if they display some overlap in insertion bias. DNA-binding proteins that are not transposases, but which are able to compete with active transpososomes for binding, will affect the tagmentation by their presence, and so affect fragment size and insertion bias. As such these combinations may be used in sequencing library preparation.

To demonstrate this, methods similar to, but not necessarily identical to, those described in Examples 5, 6, 7, 8, 9, 10, 11, and 12 are used. Briefly, active transpososomes are made from a transposase derived from a particular transposon or IS. These are mixed with inactive transpososomes (created using principles previously disclosed here) made with a transposase derived from a different transposon or IS. Alternatively, active transpososomes are mixed with unrelated DNA-binding proteins, which fulfill the role of the inactive transpososomes. Tagmentation reactions are then conducted on a DNA target of choice, using different ratios of active transpososome and competitor. The reactions are used to create sequencing libraries and these libraries are sequenced. Sequence data is then analyzed and the insertion bias and fragment length is determined.

A DNA binding protein that is different to, or distantly related to, or unrelated to the transposase used for the active transpososome may also be to control fragment size and insertion bias.

Figure 13:
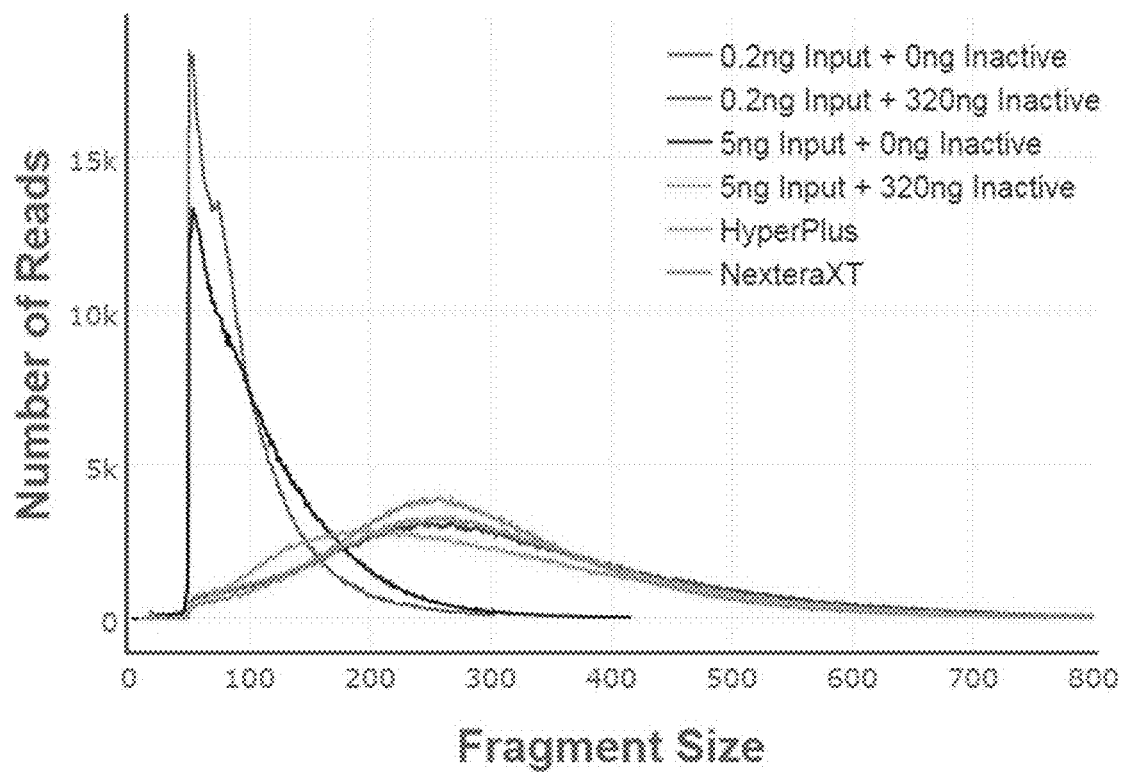
FIG. 13 is a graph demonstrating that tagmentation with a mixture of active and inactive transpososomes reduces the sensitivity of the system to variations in DNA input and quantity. Tagmentation of 200 pg (light grey line (0.2 ng Input+0 ng Inactive)) and 5 ng (dark grey line (5 ng Input+0 ng Inactive)) of genomic DNA with active transpososomes only, produced libraries that contained different insert sizes, with the 5 nanogram input library containing larger fragments, as expected. By contrast, tagmentation of 200 pg (dark blue line (0.2 ng Input+320 ng Inactive)) and 5 ng (light blue line (5 ng Input+320 ng Inactive)) of genomic DNA with a mixture of active and inactive transpososomes yielded libraries with identical insert sizes which were comparable to libraries produced with the Nextera (orange line) and Kapa HyperPlus (green line) kits.

Example 20. Tagmentation with a Mixture of Active and Inactive Transpososomes Confers Insensitivity to DNA Input Quantity Tagmentation reactions are known be sensitive to the DNA input amount, with small variations in DNA quantity resulting in variable library insert sizes and yields. To test the prediction that the combination of inactive transpososomes and active transpososomes in the tagmentation reaction confers insensitivity to DNA input amounts, different quantities of E. coli genomic DNA were tagmented with a mixture composed of either 80 nanograms of active transpososomes or a mixture composed of 80 nanograms of active transpososomes and 320 nanograms of inactive transpososomes. Libraries were amplified and sequenced on an Illumina MiSeq instrument using v3 2×150 chemistry. Library insert sizes were determined by alignment of paired reads to the reference genome and compared to typical insert sizes observed when using the Nextera XT kit (Illumina) and the Kapa HyperPlus kit. The results are shown in FIG. 13. Tagmentation of 200 pg (light grey line (0.2 ng Input+0 ng Inactive)) and 5 ng (dark grey line (5 ng Input+0 ng Inactive)) of genomic DNA with active transpososomes only, produced libraries that contained different insert sizes, with the 5 nanogram input library containing larger fragments, as expected. By contrast, tagmentation of 200 pg (dark blue line (0.2 ng Input+320 ng Inactive)) and 5 ng (light blue line (5 ng Input+320 ng Inactive)) of genomic DNA with a mixture of active and inactive transpososomes yielded libraries with identical insert sizes which were comparable to libraries produced with the Nextera (orange line) and Kapa HyperPlus (green line) kits. Collectively, these results indicate that tagmentation with a mixture of active and inactive transposomes reduces the sensitivity of the system to variations in DNA input quantity.

What is claimed is:

1. A method of fragmenting DNA comprising:
contacting input DNA and/or target DNA with a mixture of:
(a) an active transpososome, and
(b) an inactive transpososome,
under conditions suitable for transpososome activity,
wherein the active transpososome comprises a transposase derived from wild type *Alishewanella aestuarii* (TnAa), wherein the transposase is encoded by an amino acid sequence comprising SEQ ID NO:16,
wherein the inactive transpososome comprises a modified DNA arm, wherein the modified DNA arm comprises a phosphate at a 3' terminal nucleotide of the modified arm,
wherein the inactive transpososome comprises a modified transposase, wherein the modified transposase comprises an amino acid sequence of SEQ ID NO:16 comprising one or more mutations, wherein the one or more mutations is a P47K mutation,
wherein the inactive transpososome and the active transpososome bind to a consensus sequence within the input and/or target DNA with imperfect complementarity, and
wherein a ratio of an amount of the inactive transpososome to an amount of the active transpososome determines a mean fragment size and a level of insertion bias.

2. The method of claim 1, wherein the inactive transposase comprises an amino acid sequence of SEQ ID NO:32.

* * * * *